United States Patent
Wulff et al.

(10) Patent No.: US 10,344,110 B2
(45) Date of Patent: Jul. 9, 2019

(54) FUNCTIONALIZED POLYDICYCLOPENTADIENE POLYMER

(71) Applicant: UVic Industry Partnerships Inc., Victoria (CA)

(72) Inventors: Jeremy E. Wulff, Victoria (CA); Jun Chen, Victoria (CA); Matthew G. Moffitt, Victoria (CA); Fraser P. Burns, Victoria (CA); Tyler J. Cuthbert, Vancouver (CA); Chang Liu, Victoria (CA); Tong Li, Victoria (CA)

(73) Assignee: UVic Industry Partnerships Inc., Victoria, BC (CA)

( * ) Notice: Subject to any disclaimer, the term of this patent is extended or adjusted under 35 U.S.C. 154(b) by 0 days.

(21) Appl. No.: 15/999,209

(22) Filed: Aug. 17, 2018

(65) Prior Publication Data
US 2018/0371128 A1    Dec. 27, 2018

Related U.S. Application Data

(63) Continuation-in-part of application No. PCT/CA2017/050199, filed on Feb. 16, 2017.
(Continued)

(51) Int. Cl.
*C08F 32/08* (2006.01)
*C08F 132/08* (2006.01)
(Continued)

(52) U.S. Cl.
CPC ......... *C08F 132/08* (2013.01); *B01J 31/2278* (2013.01); *C08F 2/38* (2013.01);
(Continued)

(58) Field of Classification Search
CPC .............................. C08F 32/08; C08F 132/08
(Continued)

(56) References Cited

U.S. PATENT DOCUMENTS 3,287,395 A * 11/1966 Wen-Hsuan Chang ................ C08G 63/553
528/272
3,595,907 A * 7/1971 Patmore .................. C07C 51/15
558/406
(Continued)

FOREIGN PATENT DOCUMENTS

WO    WO 2015/084436    6/2015

OTHER PUBLICATIONS

Saha, S.; Ginzburg, Y.; Rozenberg, I.; Iliashevsky, O.; Ben-Asuly, A.; Lemcoff, N.G. Polym. Chem. 2016, 7, 3071-3075. (Year: 2016).*
(Continued)

*Primary Examiner* — Rip A Lee
(74) *Attorney, Agent, or Firm* — Klarquist Sparkman, LLP

(57) ABSTRACT

Disclosed herein are embodiments of methods for making and using functionalized forms of polydicyclopentadiene polymers. The disclosed polymers and methods enable a greater range of uses than the unmodified polydicyclopentadiene, which is currently used industrially. In addition, the presence of the functional groups contemplated by the disclosed compounds and formulae allow for the control of the polymer surface energy, and also enables the use of reversible chemical crosslinks, which permits recycling of the material.

21 Claims, 9 Drawing Sheets

Related U.S. Application Data

(60) Provisional application No. 62/347,446, filed on Jun. 8, 2016, provisional application No. 62/297,567, filed on Feb. 19, 2016.

(51) Int. Cl.

| | | |
|---|---|---|
| C09B 69/10 | (2006.01) |
| B01J 31/22 | (2006.01) |
| C08F 2/38 | (2006.01) |
| C08F 4/40 | (2006.01) |
| C08F 8/12 | (2006.01) |
| C08F 8/28 | (2006.01) |
| C08F 232/08 | (2006.01) |
| C08J 3/24 | (2006.01) |
| C08J 3/28 | (2006.01) |

(52) U.S. Cl.
CPC ............... *C08F 4/40* (2013.01); *C08F 8/12* (2013.01); *C08F 8/28* (2013.01); *C08F 232/08* (2013.01); *C08J 3/24* (2013.01); *C08J 3/28* (2013.01); *C09B 69/10* (2013.01); *B01J 2231/14* (2013.01)

(58) Field of Classification Search
USPC .................................................. 526/280, 281
See application file for complete search history.

(56) References Cited

U.S. PATENT DOCUMENTS

| | | | | |
|---|---|---|---|---|
| 3,725,468 A | * | 4/1973 | Patmore | .................. C07C 51/15 562/499 |
| 7,442,752 B2 | * | 10/2008 | Chun | .................. C08F 32/08 525/210 |
| 8,778,186 B2 | * | 7/2014 | Bowden | ................. B01D 71/44 210/490 |
| 2010/0010185 A1 | | 1/2010 | Bowden et al. | |
| 2014/0353254 A1 | * | 12/2014 | Bowden | ................. B01D 71/44 210/650 |

OTHER PUBLICATIONS

Chen, J.; Burns, F.P.; Moffitt, M.G.; Wulff, J.E. ACS Omega 2016, 1, 532-540. (Year: 2016).*

Chen, J,; Kilpatrick, B.; Oliver, A.G.; Wulff, J.E. J. Org. Chem. 2015, 80, 8979-8989. (Year: 2015).*

Gong et al., "ROMP of acetoxy-substituted dicyclopentadiene to a linear polymer with a high $T_g$," *RSC Advances*, vol. 5, pp. 26185-26188, 2015.

Sutthasupa et al., "Recent advances in ring-opening metathesis polymerization, and application to synthesis of functional materials," *Polymer Journal*, vol. 42, pp. 905-915, Oct. 13, 2010.

International Search Report and Written Opinion issued for International Application No. PCT/CA2017/050199 dated May 10, 2017.

Chen et al., "Expansion of Thiele's Acid Chemistry in Pursuit of a Suite of Conformationally Constrained Scaffolds," *J. Org. Chem.*, vol. 80, pp. 8979-8989, Aug. 28, 2015.

Goetz et al., "Metal-Free Preparation of Linear and Cross-Linked Polydicyclopentadiene," *J. Am. Chem. Soc.*, vol. 137, pp. 7572-7575, Jun. 8, 2015.

Panda et al., "An Improved Synthesis of Sodium and Potassium Cyclopentadienide," *Organometallics*, vol. 22, pp. 877-878, Jan. 14, 2003.

* cited by examiner

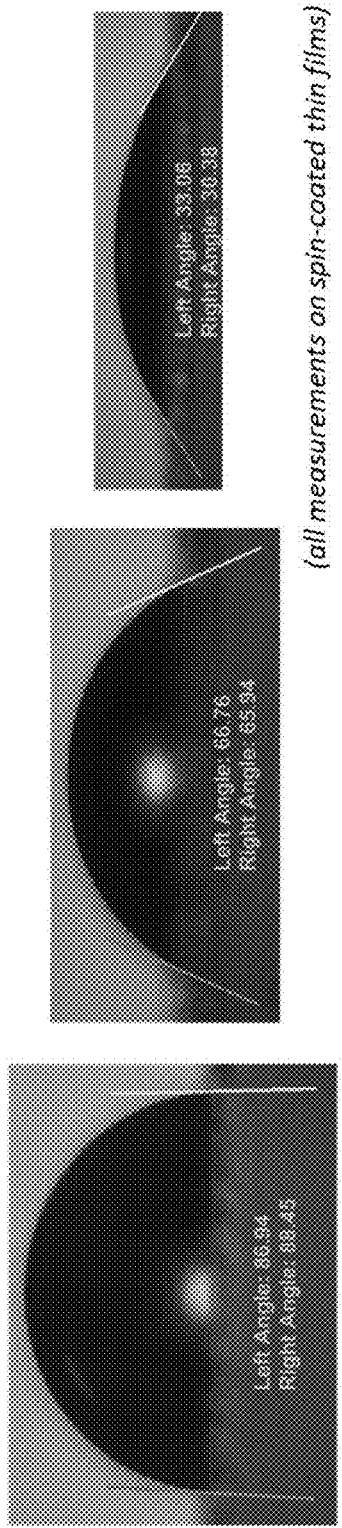
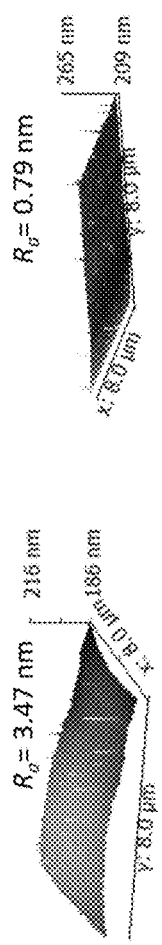
FIG. 7B
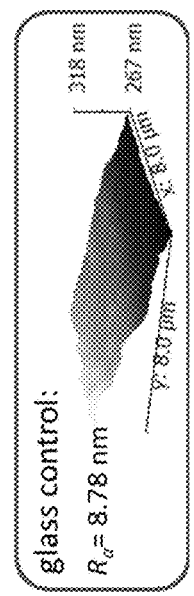
FIG. 7C
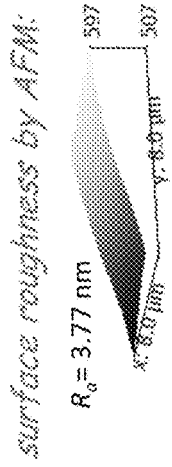

FUNCTIONALIZED POLYDICYCLOPENTADIENE POLYMER

CROSS REFERENCE TO RELATED APPLICATION

This application is a continuation-in-part of PCT Application No. PCT/CA2017/050199, filed on Feb. 16, 2017, which claims the benefit of and priority to earlier filed U.S. Provisional Patent Application No. 62/297,567, filed on Feb. 19, 2016, and U.S. Provisional Patent Application No. 62/347,446, filed on Jun. 8, 2016; each of these prior applications is incorporated herein by reference in its entirety.

FIELD

The present disclosure relates to a method for making and using functionalized forms of polydicyclopentadiene polymers.

BACKGROUND

Polydicyclopentadiene (PDCPD) is a heavily crosslinked organic polymer produced by ring-opening metathesis polymerization (ROMP) of dicyclopentadiene. Crosslinked PDCPD has a very high impact resistance (due to the extensive crosslinking), coupled with a large resistance to chemical corrosion (particularly if the alkenes in the final structure are hydrogenated), and a high heat deflection temperature. These properties make PDCPD attractive for use in the automotive industry. After initially being used to make cowlings for snowmobiles (due to its high impact resistance at low temperatures), PDCPD is now used to make body panels, bumpers and engine blocks or components for trucks, buses, tractors and construction equipment. In addition to these automotive applications, PDCPD components are used in the chlor-alkali industry, both as storage tanks for corrosive chemicals, and as cell covers for electrolyzers.

One significant limitation to polydicyclopentadiene, however, is a lack of chemical tunability, owing to the unfunctionalized homodimeric monomer feedstock. Thus, whereas polymers of functionalized ethylene (e.g. propylene, styrene, acrylic acid, methyl acrylate, acrylonitrile, methyl methacrylate, vinylidene chloride, etc.) exhibit a broad range of very distinct and very useful material properties, no such variability can be readily obtained for PDCPD-based polymers.

A second related limitation for polydicyclopentadiene concerns its lack of recyclability. As is the case with most thermoset polymers, the crosslinks in PDCPD are chemically irreversible. Due to this irreversibility, there exists no convenient way to recycle PDCPD products that have reached the end of their useful lifetimes back to a processable form, so that the material can be re-used for new products. This, combined with PDCPD's lack of malleability at high temperatures, makes the current generation of PDCPD products a material dead-end.

A third current limitation for polydicyclopentadiene (once again owing to its lack of chemical tunability) relates to the low surface energy of the polymer. This makes it difficult to robustly bond other parts to objects made from PDCPD, without resorting to separate air oxidation steps and/or lengthy adhesion protocols (often requiring specialized equipment).

Given increasing consumer and legislative demands for product recyclability, the continued growth of the PDCPD industry is unsustainable without a long-term solution to the problem of material recycling. This is true even as the automotive industry looks to replace increasing amounts of metal parts with lighter weight polymer materials; while PDCPD would be ideal for many of these applications, the current pressures from regulatory agencies like the US government to ensure that a larger percentage of automotive plastics can be recycled at the end of the vehicle's useful lifetime will make non-recyclable PDCPD an unsuitable choice. As such, there exists a need in the art for new forms of functionalized polydicyclopentadiene (also referred to as "fPDCPD"), the creation of a truly recyclable form of PDCPD, and the ability to modify the surface energy of the polymer in a consistent and controllable fashion.

SUMMARY

Disclosed herein are embodiments of polymers derived by an olefin metathesis reaction from monomeric species of the following formulae:

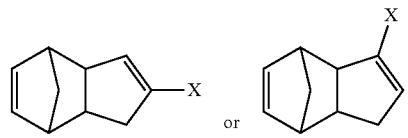

wherein X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure.

In some embodiments, the above-mentioned structures are present within mixtures of related regioisomers.

In some embodiments, polymerization of the above-referenced monomers is described, using catalysts described herein. In some embodiments, the polymerization methods can involve using metal-free olefin metathesis methods.

Also disclosed herein are embodiments of linear polymers and copolymers having structures meeting the following general formulae:

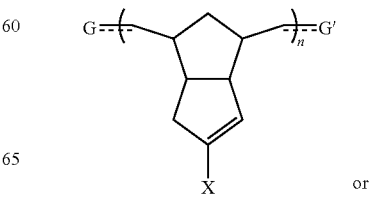

-continued

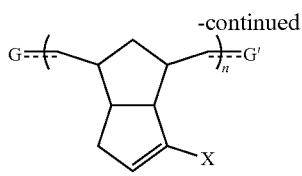

wherein G and G' are suitable polymer end-capping groups, such as —CH$_2$, —CH(aryl), —CH(aliphatic), —CH(heteroaliphatic), or —CH(heteroaryl); however, other suitable end-capping groups can be used; n is an integer ranging from at least two or greater, such as three or more, or four or more, or 10 or more; and X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure.

Also disclosed herein are embodiments of polymers (including copolymers) incorporating subunits of the following formulae:

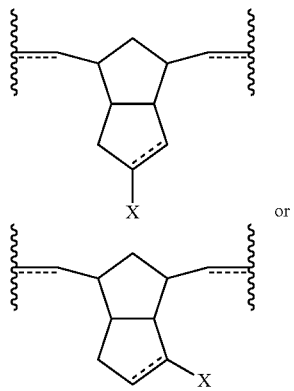

wherein X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure.

Also disclosed herein are embodiments of crosslinked polymers (including copolymers) derived from the linear polymers (including copolymers) described herein. Polymer and copolymer embodiments disclosed herein can comprise molecular crosslinks described by formulae provided herein. Also described are polymers (including copolymers) derived from pre-crosslinked monomers, described by the following formulae:

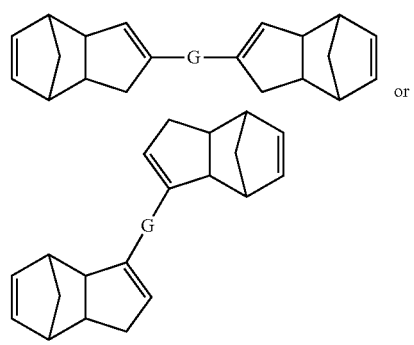

wherein G is a suitable linking group as described herein.

Additional embodiments described herein concern methods for reversing crosslinks described herein as well as using such reversible crosslinks as the basis for recycling polymers (including copolymers) derived from linear polymers incorporating subunits of formulae described herein.

A further aspect of this disclosure relates to the use of chemical or physical processes wherein the functional groups on the linear or crosslinked polymers are altered. These alterations may include hydrogenation reactions, esterification reactions, hydrolysis reactions, condensation reactions, metal-mediated coupling or decarboxylation reactions, photochemical reactions, additions of nucleophilic, electrophilic, or radical species, or other transformations that will be recognized by those skilled in the art, with the benefit of this disclosure, to be conceptually similar to those summarized here.

Yet another aspect of this disclosure relates to using the above monomers, linear polymers or crosslinked polymers (including copolymers) described herein for manufacturing processes, including injection molding, resin transfer molding, reaction injection molding (RIM), sheet molding compound (SMC) processes, bulk molding compound (BMC) processes, glass reinforced plastic (GRP) processes, and other processes used in polymer manufacturing. Another aspect of this disclosure relates to using the above mentioned monomers, linear polymers or crosslinked polymers (including copolymers) in foams, gels, aerogels, films or coatings.

BRIEF DESCRIPTION OF THE FIGURES

FIGS. 7A-7C include an exemplary surface functionalization reaction scheme (FIG. 7A) and the effects of surface functionalization on water contact angle (FIG. 7B) and surface roughness (FIG. 7C).

DETAILED DESCRIPTION

I. Explanation of Terms

Figure 1:
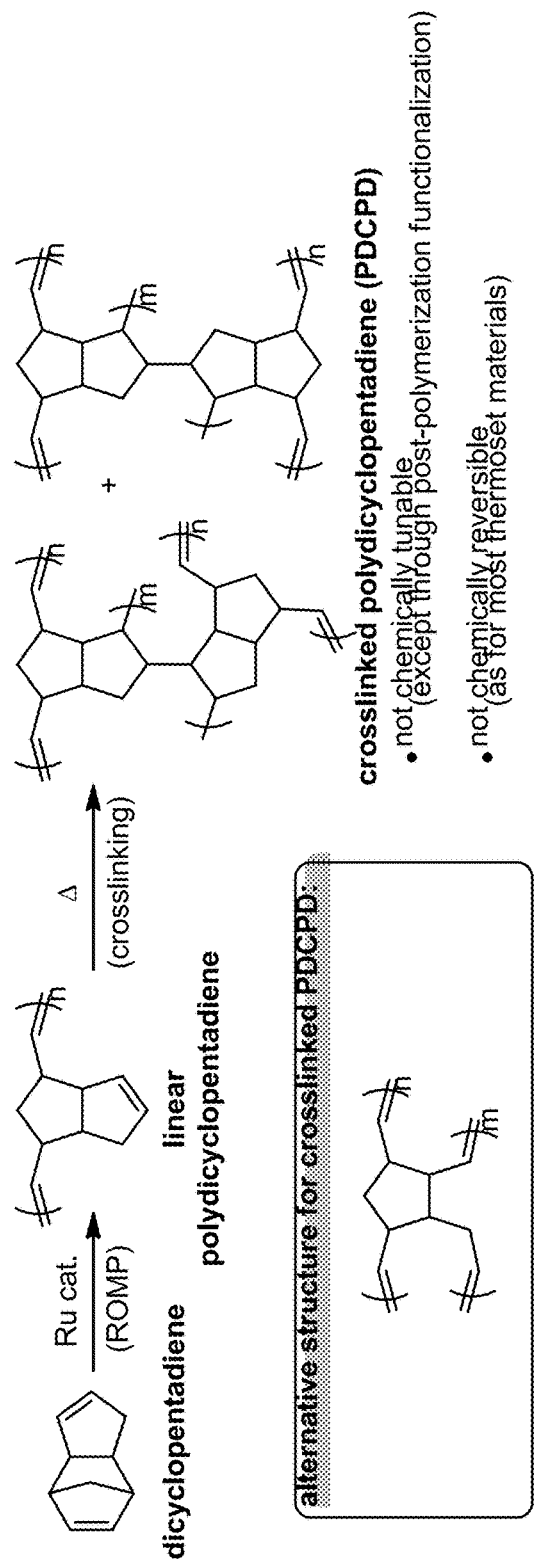
FIG. 1 illustrates a reaction scheme for making crosslinked polydicyclopentadiene.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising the compound" includes single or plural molecules and is considered equivalent to the phrase "comprising at least one compound." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. A wavy line ("〰"), is used to indicate a bond disconnection, and a dashed line ("- - -") is used to illustrate that a bond may optionally be present at a particular position. A hashed line ("⫽") indicates that either single or double bonds may be present between adjacent carbon atoms.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various examples of this disclosure, the following explanations of specific terms are provided:

Aldehyde: Is a carbonyl-bearing functional group having a formula

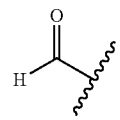

where the line drawn through the bond indicates that the functional group can be attached to any other moiety, but that such moiety simply is not indicated.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkoxy: A group (or substituent) having the structure —OR, where R is aliphatic. Methoxy (—OCH$_3$) is an exemplary alkoxy group. In a substituted alkoxy, R is aliphatic substituted with a non-interfering substituent.

Alkyl: A hydrocarbon group having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl.

Amide: Refers to a carbonyl-bearing functional group having a formula

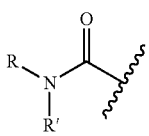

where R and R' are virtually any group, including H, aliphatic, substituted aliphatic, aryl, arylalkyl, heteroaryl, etc.

Amino: A chemical functional group —N(R)R' where R and R' independently are selected from hydrogen, aliphatic, heteroaliphatic, aryl, or heteroaryl.

Analog (or Derivative or Mimetic): A molecule that differs in chemical structure from a parent compound, for example a homolog (differing by an increment in the chemical structure, such as a difference in the length of an alkyl chain), a molecular fragment, a structure that differs by one or more functional groups, or a change in ionization.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc.

Arylalkyl: An acyclic aliphatic group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. Where specific alkyl moieties are intended, the nomenclature arylalkanyl, arylalkenyl and/or arylalkynyl may be used.

Bioactive Structure: A molecule or fragment of a molecule which elicits a desirable biological response. Exemplary bioactive structures can include, but are not limited to, antibacterial agents, antifungal agents, anticancer agents, peptides promoting cellular adhesion, signaling factors controlling cellular growth or motility, vitamins, cofactors, or anticancer agents.

Carboxylic Acid: Refers to a carbonyl-bearing functional group having a formula

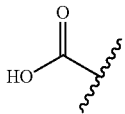

Copolymer: A polymeric material comprised of two or more different types of repeating subunits. These subunits may occur randomly throughout the polymer, or may be grouped together into blocks of similar subunits. Other monomers suitable for use in forming copolymers with the structures in the present disclosure include a variety of cyclic olefins, such as cyclobutene, cyclopentene, cycloheptene, cyclooctene, cyclononene, cyclodecene, cyclododecene, norbornene, cyclooctadiene, cyclononadiene, norbornadiene, and the like, as well as functionalized forms of the above-listed compounds. Acyclic dienes could also be used. Alternatively, two different substituted dicyclopentadienes (in which the substituent is different in each monomer) could be used for copolymerization. In yet another alternative, one or more functionalized dicyclopentadiene monomers could be used in combination with unfunctionalized dicyclopentadiene monomer to prepare a copolymer that contains a variable quantity of functional groups within its structure.

Cyclic: Designates a substantially hydrocarbon, closed-ring compound, or a radical thereof. Cyclic compounds or substituents also can include one or more sites of unsaturation. One example of such a cyclic compound is cyclopentadiene. In the usage herein, cyclic includes heterocyclic.

Dye: A compound that exhibits color and/or changes the color of substance, reaction mixture, or the like. Exemplary dyes can include, but are not limited to, acridine dyes (including any derivatives of acridine), anthraquinone dyes (including any derivatives of anthraquinone), arylmethane dyes (including diarylmethane dyes, triarylmethane dyes), azo dyes (including dyes having an azo group), diazonium dyes (including diazonium salt compounds), nitro dyes (including dyes having a nitro group), nitroso dyes (including dyes having a nitroso functional group), phthalocyanine dyes (including derivatives of phthalocyanine), quinone-imine dyes (including azin dyes, indamins, indophenols, oxazins, oxazones, thiazines, or derivatives of quinone), thiazole dyes (including thiazole derivatives), safranin dyes (including derivatives of safranin), xanthene dyes (including derivatives of xanthene, fluorine, and rhodamine), and the like.

Electron-Withdrawing Group: A functional group capable of accepting electron density from the structure to which it is directly attached, such as by inductive electron withdrawal. Exemplary electron-withdrawing groups can be selected from, but not limited to, one or more of the following: aldehyde, ketone, ester, carboxylic acid, acyl, acyl halide, cyano (or nitrile), sulfone, sulfoxide, sulfonic acid, sulfinic acid, sulfonate, nitro, nitroso, quaternary amine, pyridinyl, alkyl halide, and the like.

Ester: Refers to a carbonyl-bearing substituent having a formula

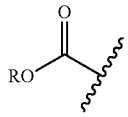

where R is virtually any group, including aliphatic, substituted aliphatic, aryl, arylalkyl, heteroaryl, etc.

Ether: A substituent having a general formula R—O—R', where R and R' independently can be selected from aliphatic, aryl, heteroaliphatic, or heteroaryl and typically at least one of R and/or R' are attached to a compound disclosed herein.

Fluorophore: A functional group or portion of a molecule that is capable of fluorescence. In some embodiments, a fluorophore can cause the molecule to fluoresce when exposed to an excitation source. Exemplary fluorophores include, but are not limited to, fluorescein, rhodamine, and BODIPY.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups can be substituted with one or more substituents.

Heterocyclic: Refers to a closed-ring compound, or radical thereof as a substituent bonded to another group, particularly other organic groups, where at least one atom in the ring structure is other than carbon, and typically is oxygen, sulfur and/or nitrogen.

Ketone: Refers to a carbonyl-bearing substituent having a formula

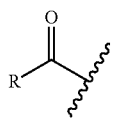

where R is virtually any group, including aliphatic, substituted aliphatic, aryl, arylalkyl, heteroaryl, etc.

Nitrile: Refers to a substituent having a formula

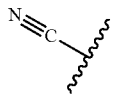

Molecular Sensor: A compound or functional group capable of sensing/detecting the presence of an analyte. Exemplary molecular sensors include, but are not limited to, boronic acids, which are useful sensors for determining the presence of sugar compounds, and fluorescent molecules (or fluorophores), which can gain or lose fluorescence upon metal binding, thereby making them useful for sensing the presence of metals.

Photoredox mediator: A photoredox catalyst that comprises an organic component, such as a dye molecule and may or may not comprise a metal component. An exemplary photoredox mediator comprising a metal component is Ru(bipy)$_3$ (known also as tris(bipyridine)ruthenium(II) chloride).

Polymer: An organic or mixed organic/inorganic molecule comprised of repeating subunits. In some embodiments, a polymer can comprise repeating subunits that are the same or different. In embodiments where the polymer comprises repeating subunits that are different, the polymer can be a copolymer.

Salt Form (or "salt thereof"): In some embodiments, salt forms of compounds are described herein, such as salt forms of substituted cyclopentadiene compounds. In some embodiments, these salt forms of the substituted cyclopentadiene compounds can be referred to as a salt of the substituted cyclopentadiene (or a "salt thereof"). Such salts can have a formula illustrated below, wherein M is an alkali metal, an alkaline earth metal, or a non-metallic counterion, with examples being described herein

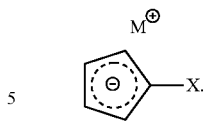

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as an aryl group, a cyclic group, a heteroaryl group or a heterocyclic group. All functional groups described herein can be substituted unless otherwise specified; however, the lack of the word "substituted" before a functional group and/or variable described herein does not mean that the functional group and/or variable is not substituted.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein.

II. Introduction

Polydicyclopentadiene (PDCPD) is a heavily crosslinked organic polymer produced by ring-opening metathesis polymerization (ROMP) of dicyclopentadiene, as illustrated in FIG. 1. While post-polymerization strategies to functionalize the residual double bonds in the PDCPD polymer matrix exist, such as epoxidation, bromination, inverse-demand Diels Alder, and radical-initiated thiol-ene addition of the residual double bonds, these methods depend on the ability of reagents to access the olefin in the polymer. As a result, these strategies are largely limited to the functionalization of PDCPD foams, or else to functionalization solely at the surface. Co-polymerization strategies have also been used to incorporate functionality into products, such as Quintone 1500 and Quintone 1700, which are copolymers of dicyclopentadiene and vinyl ester or allyl alcohol, respectively.

Two reports of polymerization of a 1-hydroxy-substituted dicyclopentadiene have occurred in the art. In these reports, the 1-hydroxy-substituted dicyclopentadiene compound was generated by known allylic oxidation protocols. Following an optional reaction of the alcohol to produce a corresponding acetate, benzoate, or —O(CH$_2$)$_n$CH$_3$ group (where n is 0, 2, or 7), polymerization delivered the corresponding functionalized materials. However, the placement of the functional group at the allylic position makes the final products much less thermally robust than the parent polymers (possibly due to the ready formation of allylic cations), and in many cases catastrophic mass loss occurs upon heating beyond ca. 220° C. Moreover, the degree of cross-linking appears to be greatly reduced for this class of polymers, as evidenced by the low T$_g$ values reported for the majority of products.

The disclosed polymers and methods enable a greater range of uses than the unmodified polydicyclopentadiene that is currently used industrially, while maintaining the high $T_g$ and good thermal stability of the parent polymer. In addition, the presence of the functional groups of the disclosed polymers allows for the control of the polymer surface energy, and also enables the use of reversible chemical crosslinks, which permits recycling of the material.

III. Compounds

Disclosed herein are embodiments of compounds, such as polymers, copolymers, and polymers comprising molecular crosslinks. These embodiments are described in more detail below.

In some embodiments, polymers derived by olefin metathesis reaction from monomeric species of the following formulae are described:

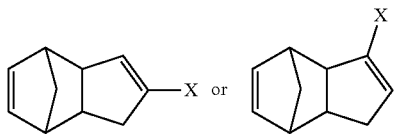

wherein X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure. In particular embodiments, X is an electron-withdrawing group or radical-stabilizing group. In some embodiments, X independently may be selected from heteroatom-containing functional groups, such as, but not limited to, esters (—$CO_2R$), acids (—$CO_2H$), amides (—CONRR'), ketones (—COR), aldehydes (—COH), nitriles (—CN), nitro groups (—$NO_2$), trifluoromethyl groups (—$CF_3$), alkoxy groups (—OR), phosphine oxides, sulfur-containing species (such as sulfones (—$SO_2R$), sulfoxides (—SOR), sulfonic acids (—$SO_2OH$), sulfonates (—$SO_2OR$), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —$(CH_2)_y$OH; —$(CH_2)_y$SH; or —$(CH_2)_y NR^a R^b$, where y is an integer between 0 and 10 and $R^a$ and $R^b$ independently are selected from H, aliphatic, aryl, heteroaliphatic, heteroaryl, or combinations thereof. In yet some additional embodiments, R, R', $R^a$, and/or $R^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

Also disclosed are polymers derived by an olefin metathesis reaction from a monomeric species that is present in the following mixture of related regioisomers:

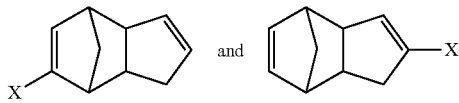

wherein X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure. In particular embodiments, X is an electron-withdrawing group or radical-stabilizing group. In some embodiments, X independently may be selected from heteroatom-containing functional groups, such as, but not limited to, esters (—$CO_2R$), acids (—$CO_2H$), amides (—CONRR'), ketones (—COR), aldehydes (—COH), nitriles (—CN), nitro groups (—$NO_2$), trifluoromethyl groups (—$CF_3$), alkoxy groups (—OR), phosphine oxides, sulfur-containing species (such as sulfones (—$SO_2R$), sulfoxides (—SOR), sulfonic acids (—$SO_2OH$), sulfonates (—$SO_2OR$), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —$(CH_2)_y$OH; —$(CH_2)_y$SH; or —$(CH_2)_y NR^a R^b$, where y is an integer between 0 and 10 and $R^a$ and $R^b$ independently are selected from H, aliphatic, aryl, heteroaliphatic, heteroaryl, or combinations thereof. In yet some additional embodiments, R, R', $R^a$, and/or $R^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like)phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

In some embodiments, the compound can be a linear polymer having a structure meeting any of the following general formulae:

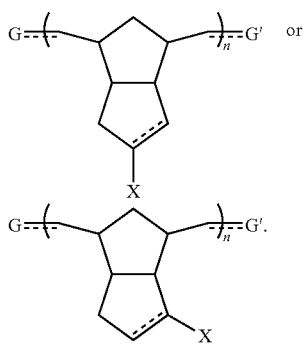

In some embodiments, the linear polymer can have a structure meeting any of the following general formulae:

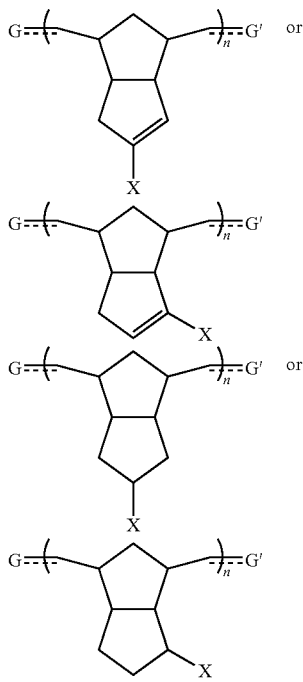

With reference to any of the above formulae, G and G' are suitable polymer end-capping groups. In some embodiments, an end-capping group can be obtained from the catalyst employed during polymerization and/or by quenching polymerization with an additional chemical reagent. In some embodiments, the end-capping group can be selected from —CH$_2$, —CH(aryl), —CH(aliphatic), —CH(heteroaliphatic), or —CH(heteroaryl), such as —CH(phenyl) or —CH(alkyl). In some embodiments, other suitable end-capping groups can be used. With respect to these formulae, n is an integer ranging from at least two or greater, such as three or more, or four or more, or 10 or more; and X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure. In particular embodiments, X is an electron-withdrawing group or radical-stabilizing group. In some embodiments, X independently may be selected from heteroatom-containing functional groups, such as, but not limited to, esters (—CO$_2$R), acids (—CO$_2$H), amides (—CONRR'), ketones (—COR), aldehydes (—COH), nitriles (—CN), nitro groups (—NO$_2$), trifluoromethyl groups (—CF$_3$), alkoxy groups (—OR), phosphine oxides, sulfur-containing species (such as sulfones (—SO$_2$R), sulfoxides (—SOR), sulfonic acids (—SO$_2$OH), sulfonates (—SO$_2$OR), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —(CH$_2$)$_y$OH; —(CH$_2$)$_y$SH; or —(CH$_2$)$_y$N-R$^a$R$^b$, where y is an integer between 0 and 10 and R$^a$ and R$^b$ independently are selected from H, aliphatic, aryl, heteroaliphatic, heteroaryl, or combinations thereof. In yet some additional embodiments, R, R', R$^a$, and/or R$^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

Also disclosed herein are polymers (including copolymers) incorporating at least one subunit having a structure meeting one or more of the following formulae:

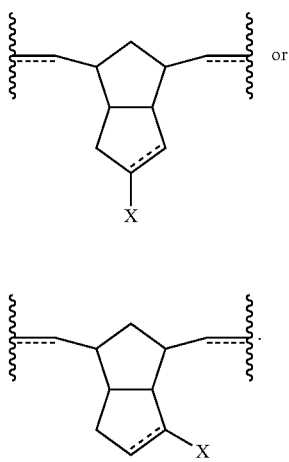

In some embodiments, the polymer or copolymer can have a structure meeting any of the following general formulae:

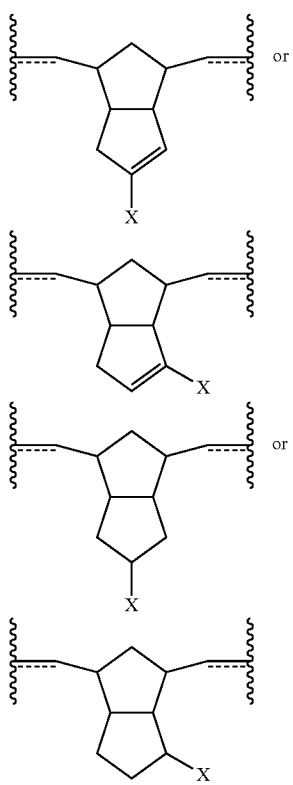

With reference to any of the above formulae, X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure. In particular embodiments, X is an electron-withdrawing group or radical-stabilizing group. In some embodiments, X independently may be selected from heteroatom-containing functional groups, such as, but not limited to, esters (—$CO_2R$), acids (—$CO_2H$), amides (—CONRR'), ketones (—COR), aldehydes (—COH), nitriles (—CN), nitro groups (—$NO_2$), trifluoromethyl groups (—$CF_3$), alkoxy groups (—OR), phosphine oxides, sulfur-containing species (such as sulfones (—$SO_2R$), sulfoxides (—SOR), sulfonic acids (—$SO_2OH$), sulfonates (—$SO_2OR$), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —$(CH_2)_yOH$; —$(CH_2)_ySH$; or —$(CH_2)_yN$-$R^aR^b$, where y is an integer between 0 and 10 and $R^a$ and $R^b$ independently are selected from H, aliphatic, aryl, heteroaliphatic, heteroaryl, or combinations thereof. In yet some additional embodiments, R, R', $R^a$, and/or $R^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

In some embodiments, crosslinked polymers (including copolymers) derived from the above-mentioned linear polymers (including copolymers) are contemplated by the present disclosure. In yet additional embodiments, crosslinked polymers containing molecular crosslinks as illustrated by the following formulae are disclosed:

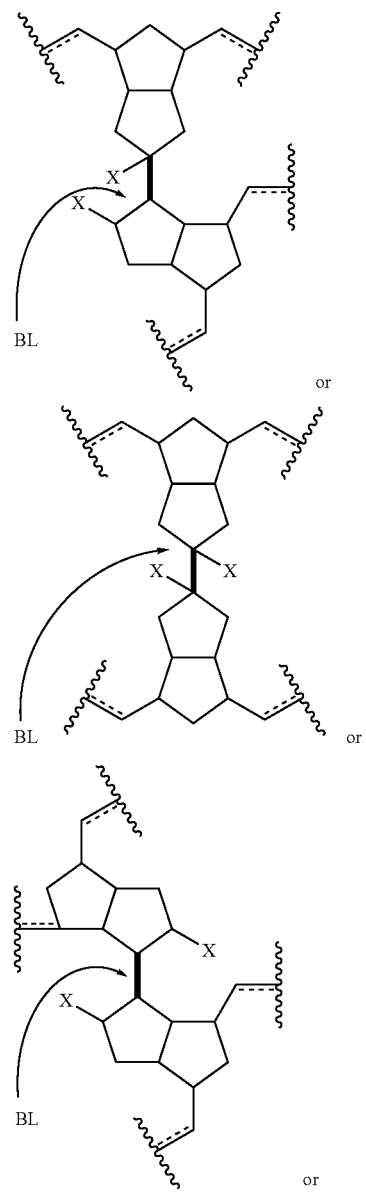

-continued

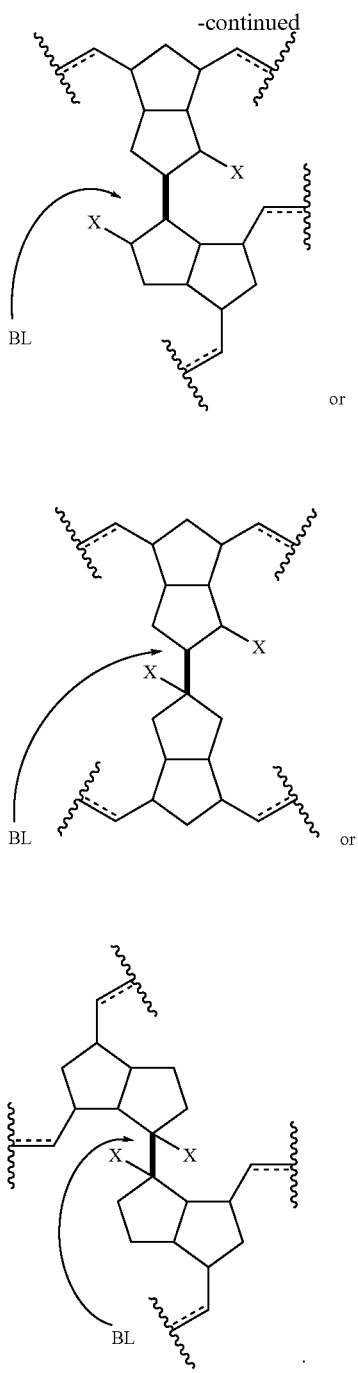

or

With respect to these formulae, the bold line (illustrated with arrows labeled "BL") constitutes a primary molecular crosslink, which may be accompanied by the addition of further functional groups or sub-units; and X is an electron-withdrawing group or radical-stabilizing group. In some embodiments, X independently may be selected from heteroatom-containing functional groups, such as, but not limited to, esters (—$CO_2R$), acids (—$CO_2H$), amides (—CONRR'), ketones (—COR), aldehydes (—COH), nitriles (—CN), nitro groups (—$NO_2$), trifluoromethyl groups (—$CF_3$), alkoxy groups (—OR), phosphine oxides, sulfur-containing species (such as sulfones (—$SO_2R$), sulfoxides (—SOR), sulfonic acids (—$SO_2OH$), sulfonates (—$SO_2OR$), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —$(CH_2)_yOH$; —$(CH_2)_ySH$; or —$(CH_2)_yNR^aR^b$, where y is an integer between 0 and 10 and $R^a$ and $R^b$ independently are selected from H, aliphatic, aryl, heteroaliphatic, heteroaryl, or combinations thereof. In yet some additional embodiments, R, R', $R^a$, and/or $R^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

A further aspect of the present disclosure relates to crosslinked polymers (including copolymers) containing molecular crosslinks illustrated by the following formulae:

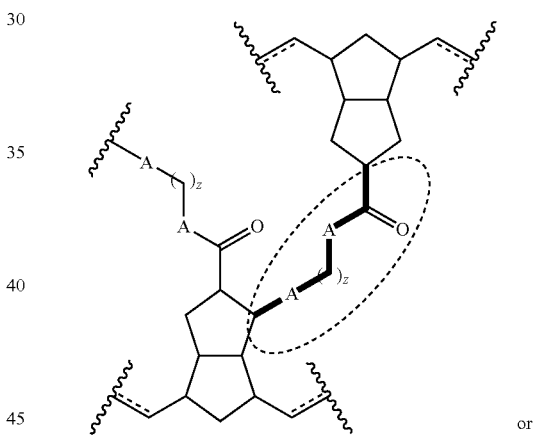

or

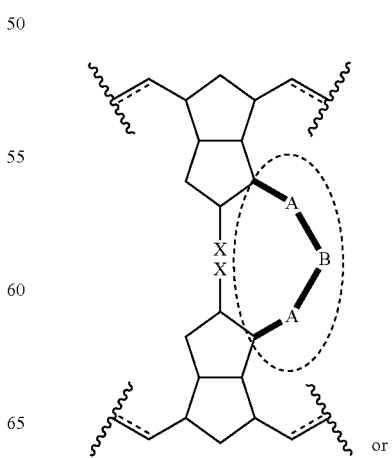

or

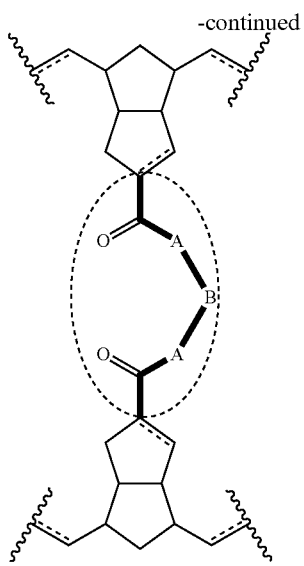

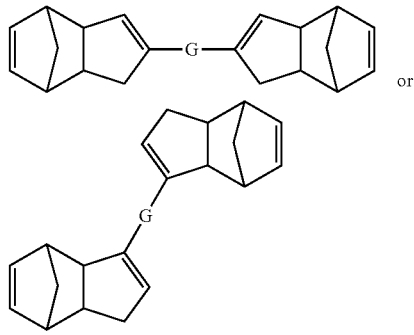

wherein the bold lines illustrated in the formulae (enclosed with the dashed-line circles illustrated above) constitute a primary molecular crosslink, which may be accompanied by the addition of further functional groups or sub-units; A is any heteroatom, such as O, S, N, or the like; or any heteroatom-containing group such as NH, NR, where R is aliphatic, aromatic, heteroaromatic, or a combination thereof; B is any suitable linking group including an aliphatic group, aromatic group, or heteroaromatic group, or a combination of these groups; Z is an integer between 0 and 10; and X is an electron-withdrawing group or radical-stabilizing group. In some embodiments, X independently may be selected from heteroatom-containing functional groups, such as, but not limited to, esters (—CO$_2$R), acids (—CO$_2$H), amides (—CONRR'), ketones (—COR), aldehydes (—COH), nitriles (—CN), nitro groups (—NO$_2$), trifluoromethyl groups (—CF$_3$), alkoxy groups (—OR), phosphine oxides, sulfur-containing species (such as sulfones (—SO$_2$R), sulfoxides (—SOR), sulfonic acids (—SO$_2$OH), sulfonates (—SO$_2$OR), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —(CH$_2$)$_y$OH; —(CH$_2$)$_y$SH; or —(CH$_2$)$_y$NR$^a$R$^b$, where y is an integer between 0 and 10 and R$^a$ and R$^b$ independently are selected from H, aliphatic, aryl, heteroaliphatic, heteroaryl, or combinations thereof. In yet some additional embodiments, R, R', R$^a$, and/or R$^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

Also disclosed herein are embodiments of polymers (including copolymers) derived from pre-crosslinked monomers having structures meeting any of the following formulae:

wherein G is a suitable linking group. In some embodiments, G can be selected from, but is not limited to, esters, amides, aliphatic groups, aryl groups, heteroaryl groups, olefins, alkynes, ethers, silyl ethers, aliphatic silanes, disulfides, ring structures (e.g., cyclic groups), or other groups recognized by those skilled in the art with the benefit of the present disclosure to be cleavable under specific conditions as described herein.

Also disclosed herein are embodiments of polymers containing molecular crosslinks having structures meeting the following formulae:

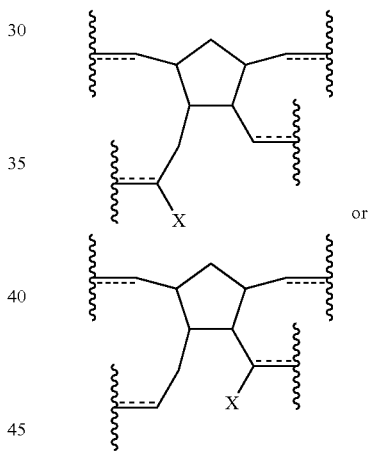

wherein X is a functional group other than hydrogen, such as an electron-withdrawing group, a radical-stabilizing group, or a functional group other than an electron-withdrawing group or a radical-stabilizing group. In some embodiments, the functional group other than an electron-withdrawing group or a radical-stabilizing group can be a functional group obtained from a chemical conversion of an electron-withdrawing group. In some embodiments, chemical conversions can include, but are not limited to, hydrogenation reactions, esterification reactions, hydrolysis reactions, condensation reactions, metal-mediated coupling reactions, decarboxylation reactions, photochemical reactions, additions of a nucleophilic, electrophilic, or radical species, any or all combinations thereof, or other transformations that will be recognized by those skilled in the art with the benefit of this disclosure. In some embodiments, X independently may be selected from heteroatom-containing functional groups, such as, but not limited to, esters (—CO$_2$R), acids (—CO$_2$H), amides (—CONRR'), ketones (—COR), aldehydes (—COH), nitriles (—CN), nitro groups (—NO₂), trifluoromethyl groups (—CF₃), alkoxy groups (—OR), phosphine oxides, sulfur-containing species (such as sulfones (—SO₂R), sulfoxides (—SOR), sulfonic acids (—SO₂OH), sulfonates (—SO₂OR), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —(CH₂)$_y$OH; —(CH₂)$_y$SH; or —(CH₂)$_y$NR$^a$R$^b$, where y is an integer between 0 and 10 and R$^a$ and R$^b$ independently are selected from H, aliphatic, aryl, heteroaliphatic, heteroaryl, or combinations thereof. In yet some additional embodiments, R, R', R$^a$, and/or R$^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

In some embodiments, the disclosed molecular crosslinked compounds comprise reversible crosslinks. Such reversible crosslinks allow for these compounds to serve as the basis for recycling polymers (including copolymers) derived from linear polymers incorporating subunits of the following formulae:

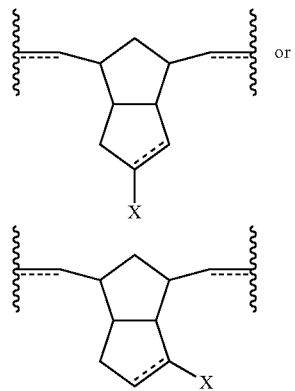

wherein X is an electron-withdrawing group or radical-stabilizing group. In some embodiments, X independently may be selected from heteroatom-containing functional groups, such as, but not limited to, esters (—CO₂R), acids (—CO₂H), amides (—CONRR'), ketones (—COR), aldehydes (—COH), nitriles (—CN), nitro groups (—NO₂), trifluoromethyl groups (—CF₃), alkoxy groups (—OR), phosphine oxides, sulfur-containing species (such as sulfones (—SO₂R), sulfoxides (—SOR), sulfonic acids (—SO₂OH), sulfonates (—SO₂OR), sulfinic acids (—S(O)OH), thiols, thioethers (—SR), and disulfides (—SSR)), or other groups capable of stabilizing adjacent anionic or radical species. In some embodiments, R and R' independently can be selected from H, aliphatic, aryl, heteroaliphatic, heteroaryl, or combinations thereof; —(CH₂)$_y$OH; —(CH₂)$_y$SH; or —(CH₂)$_y$NR$^a$R$^b$, where y is an integer between 0 and 10 and R$^a$ and R$^b$ independently are selected from H, aliphatic, aryl, heteroaliphatic, heteroaryl, or combinations thereof. In yet some additional embodiments, R, R', R$^a$, and/or R$^b$ independently can be selected from H, alkyl (e.g., lower alkyl, such as methyl, ethyl, propyl, butyl, and the like), branched alkyl (e.g., branched lower alkyl, such as iso-propyl, iso-butyl, sec-butyl, tert-butyl, and the like), cyclic alkyl (e.g., cyclopropyl, cyclobutyl, cyclopentyl, cyclohexyl, and the like), phenyl, naphthyl, ethers, thioethers, amines, esters, thioesters, amides, and combinations thereof. In yet additional embodiments, R and R' independently can comprise (e.g., be substituted with) a functional group such as a dye, fluorophore, bioactive structure, molecular sensor, or any and all combinations thereof.

Exemplary monomer compounds, polymers, copolymers, and crosslinked polymers are provided below:

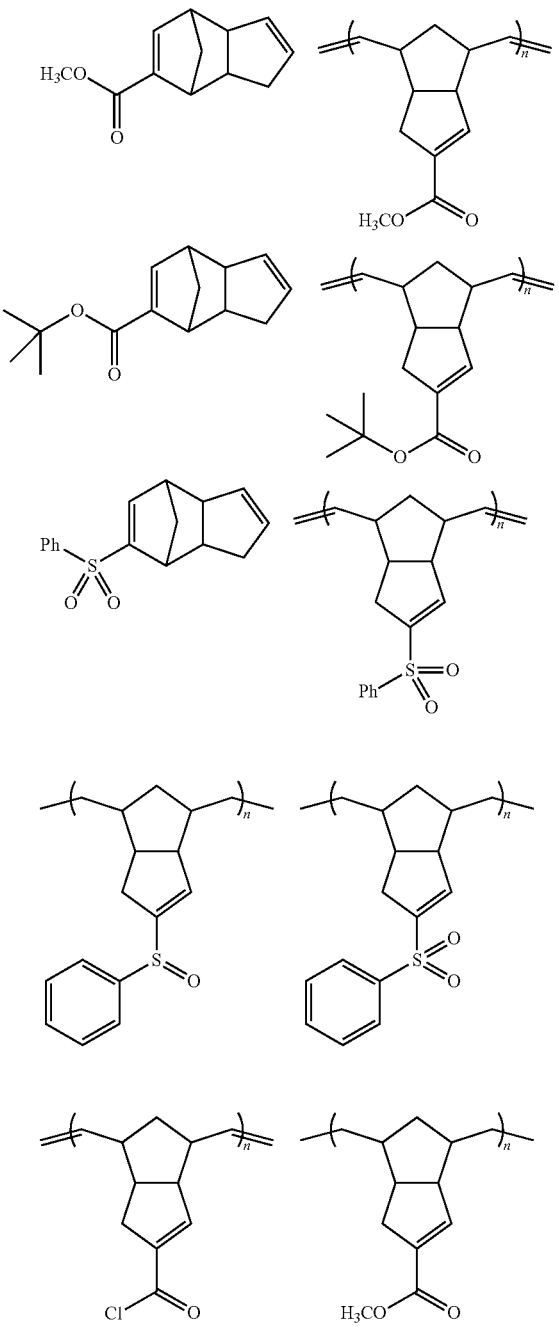

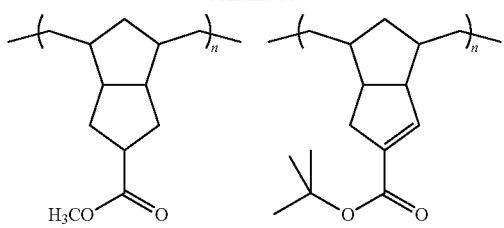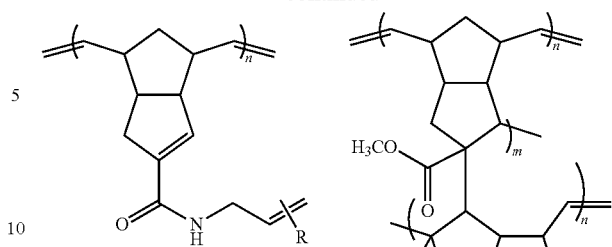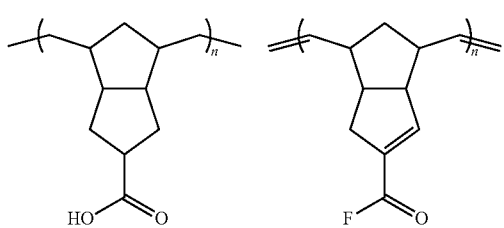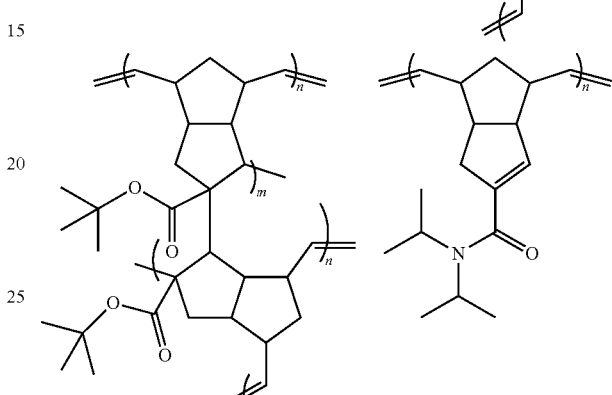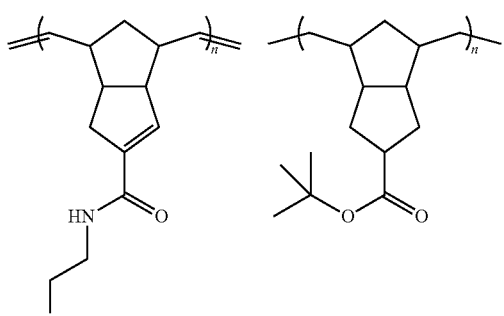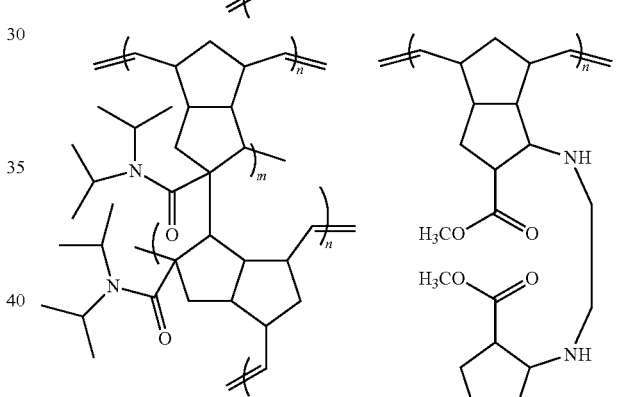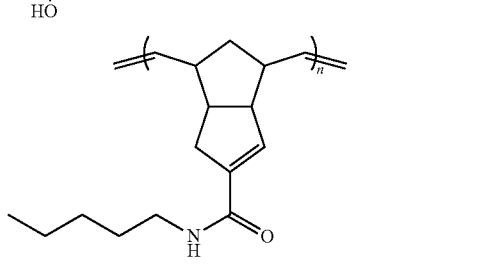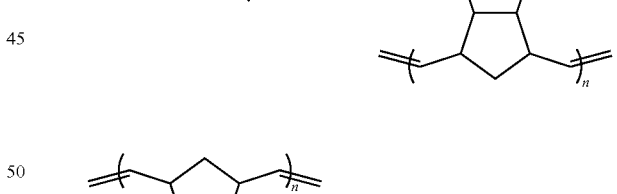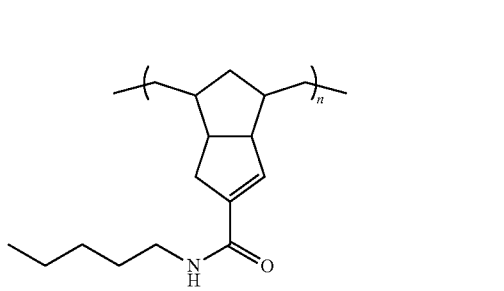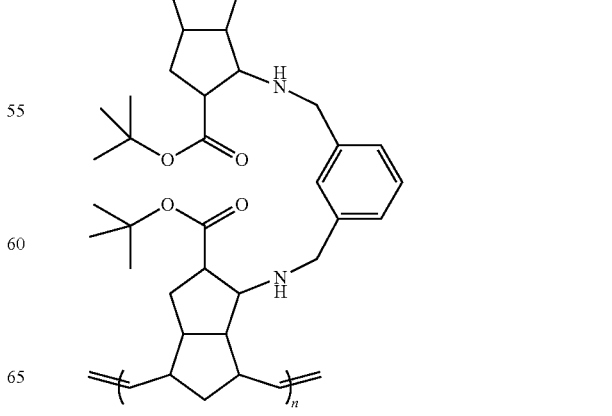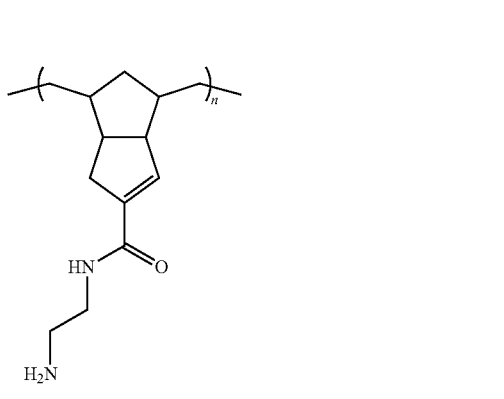

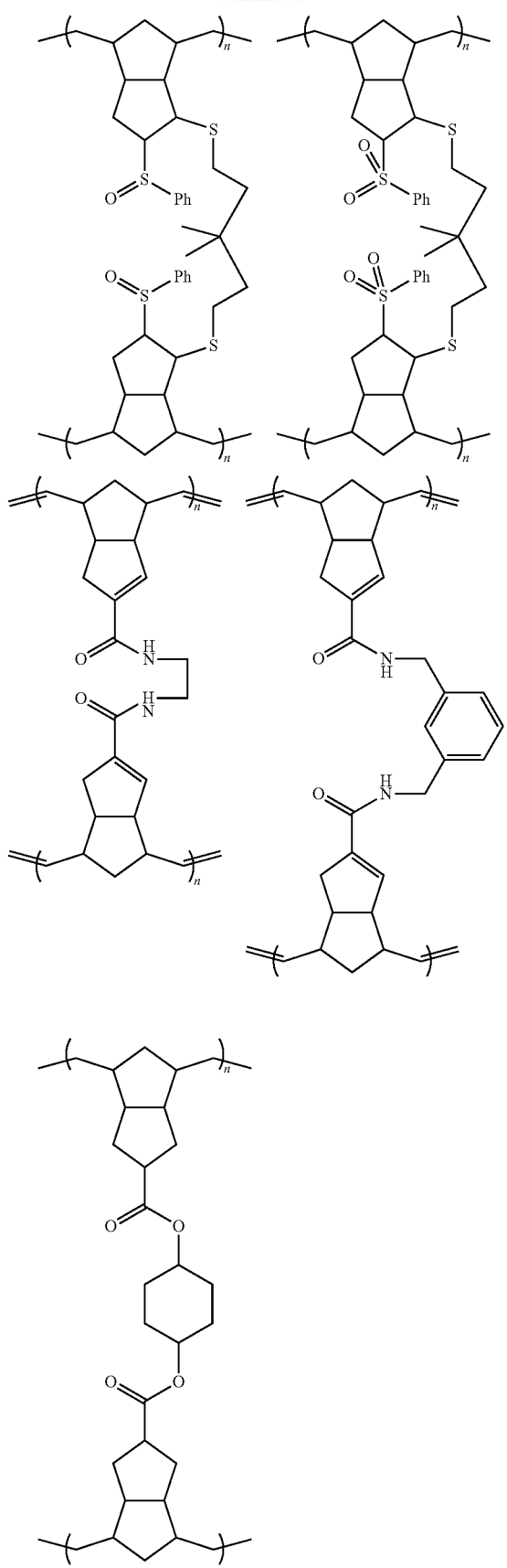

-continued

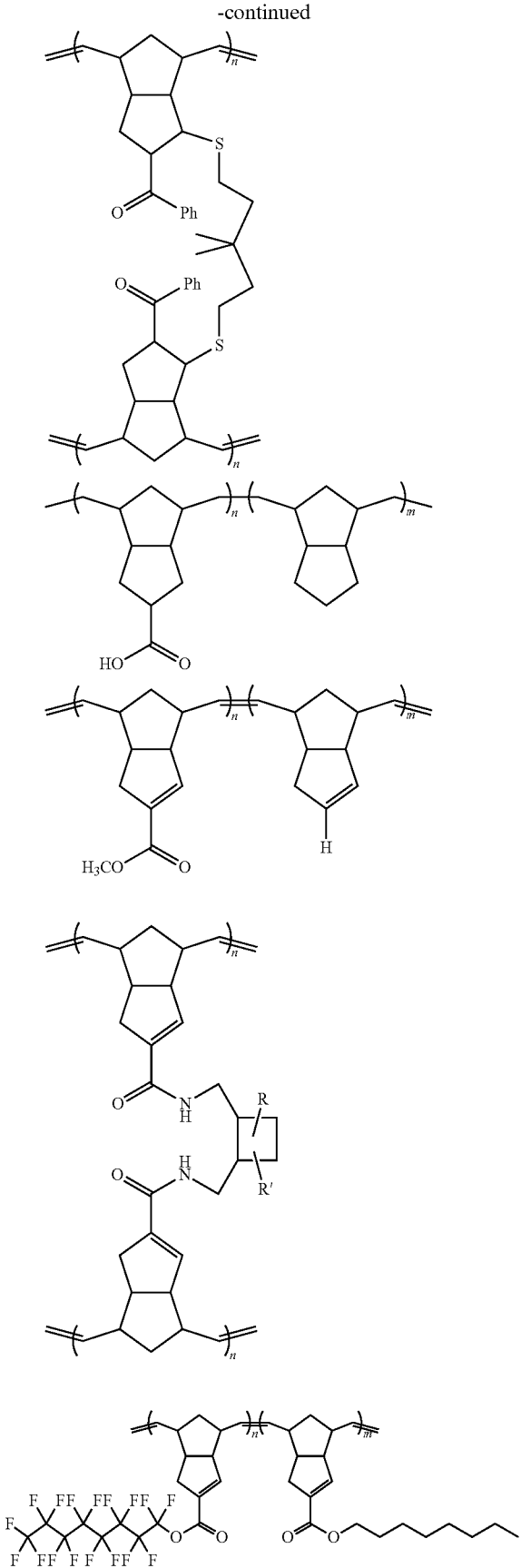

IV. Exemplary Methods for Making Disclosed Compounds

Disclosed embodiments of the present disclosure also concern making the disclosed compounds, and compositions comprising the compounds. The compositions are prepared by applicable variety of organic synthetic techniques, as will be understood by a person of ordinary skill in the art based on the following discussion. These include, but are not limited to, condensations, cycloadditions, rearrangements, or alkylations from any applicable acyclic, monocyclic or bicyclic precursors. These also include degradations from compounds of higher molecular weight.

One exemplary method for preparing disclosed materials is provided in Scheme 1 below.

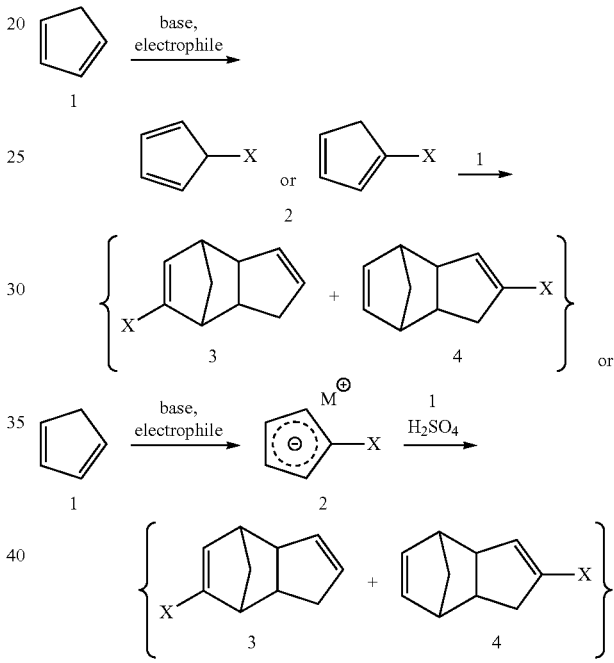

A method for making compounds having the general formula 3 and 4 is disclosed, wherein each X and M can be as described herein. As part of this method, a starting material 1 is deprotonated with a base, and an electrophile is added to deliver the functional group "X." It will be appreciated by those skilled in the art, with the benefit of the present disclosure, that the starting material may already be acquired in deprotonated form, for example as a cyclopentadienylide with a corresponding metal or non-metallic counterion. Suitable counterions can include, but are not limited to alkali or alkaline earth metals, or organic counterions. In some embodiments, alkali metal counterions can be selected from sodium, lithium, potassium, rubidium, cesium, and francium. In some embodiments, alkaline earth metal counterions can be selected from magnesium, calcium, strontium, barium, radium, or beryllium. In exemplary embodiments, sodium, lithium or potassium cyclopentadienylides can be used. Organic counterions can include, but are not limited to, tetra-substituted ammonium species, such as tetra-alkylated ammonium ions, tetra-aryl ammonium ions, or tetra-substituted ammonium ions comprising mixtures of alkyl and aryl groups. Exemplary tetra-substituted ammonium compounds can include, but are not limited to, tetra-methyl ammonium cations, tetra-ethyl ammonium cations, tetra-butyl ammonium cations, tetra-phenyl ammonium cations, and the like. Depending on the electrophile employed in the method, the building block 2 may be isolated as the neutral species or as the salt form. If the salt form is used, this material may be isolated for purification or handling purposes, or may be carried on crude to the next step of the reaction sequence. In some embodiments, the electrophile is dimethyl carbonate. In embodiments using dimethyl carbonate as an electrophile, the reaction can take place with a polar aprotic solvent, such as those described below, or it can be performed in neat dimethyl carbonate. In some embodiments, a mixture of regioisomers of building block 2 can be obtained, which can then provide a mixture of regioisomeric products 3 and 4. In yet additional embodiments, the method can produce a single regioisomer as building block 2 and this single regioisomer can be used to obtain a single regioisomer after reaction with compound 1. In some such embodiments, the product can be regioisomer 3 or regioisomer 4.

Intermediate 2 is then reacted with compound 1 to arrive at the desired products 3 and 4. In embodiments where a salt form of 2 is employed, an acid such as sulfuric acid may be used to generate the neutral form in situ. Compounds 3 and 4 may be separated, or may be left as a mixture.

A further exemplary method for preparing disclosed materials is provided in Scheme 2 below.

Scheme 2

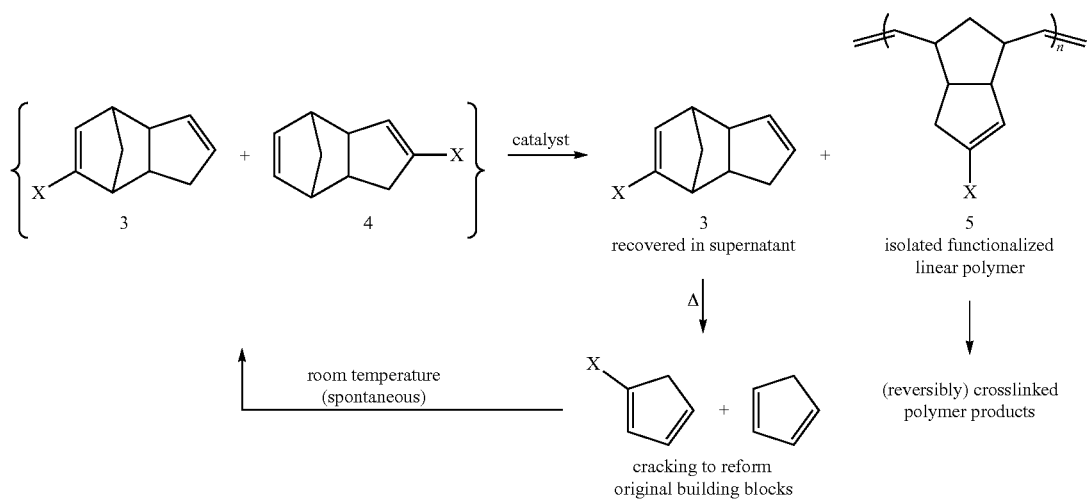

Exemplary embodiments of the method described by Scheme 2 are illustrated below.

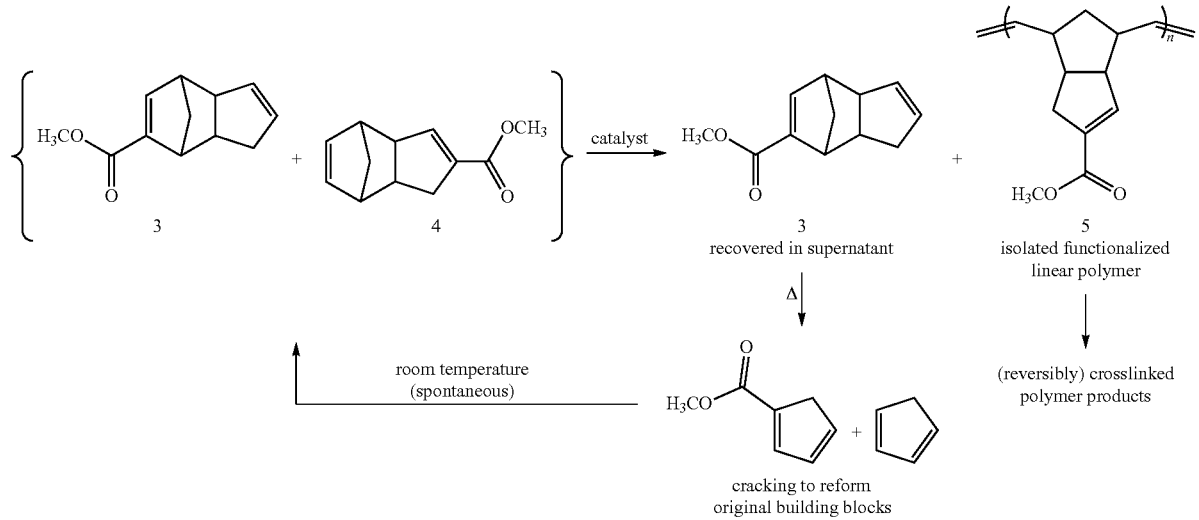

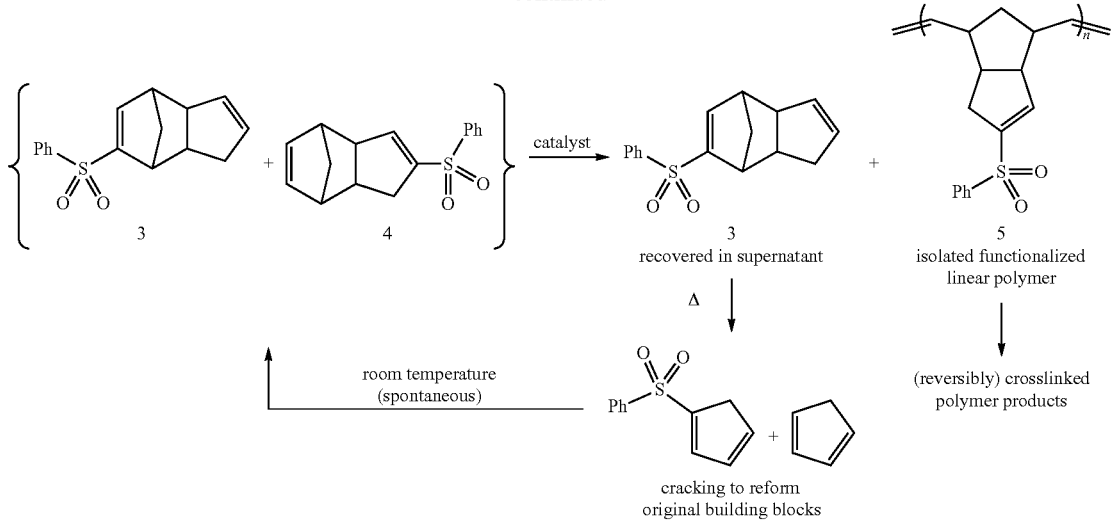

recovered in supernatant isolated functionalized linear polymer room temperature (spontaneous)

(reversibly) crosslinked polymer products cracking to reform original building blocks With respect to these embodiments, a method for making the functionalized linear polymer 5 is disclosed, wherein a mixture of compounds 3 and 4 (or else purified or partially purified compound 4) is subjected to a catalyst capable of promoting ring-opening/metathesis reactions. The catalyst may contain a ruthenium, molybdenum or tungsten metal, or may contain other metals. Exemplary catalysts include, but are not limited to, ruthenium-based metathesis catalysts, such as Grubbs catalysts (e.g., benzylidene-bis(tricyclohexylphosphino)-dichlororuthenium, CAS #172222-30-9; [1,3-bis-(2,4,6-trimethylphenyl)-2 imidazolidinylidene]dichloro (phenylmethylene)(tricyclohexylphosphino)ruthenium, CAS #246047-72-3, dichloro[1,3-bis(2,4,6-trimethylphenyl)-2-imidazolidinylidene](benzylidene)bis(3-bromopyridine)ruthenium, CAS #900169-53-1), Hoveyda-Grubbs catalysts (e.g., dichloro(o-isopropoxyphenylmethylene)(tricyclohexylphosphine)ruthenium(II), CAS #203714-71-0); dichloro(o-isopropoxyphenylmethylene)(tricyclohexylphosphine)ruthenium(II), CAS #203714-71-0; [1,3-Bis-(2,4,6-trimethylphenyl)-2-imidazolidinylidene]dichloro(o-isopropoxyphenylmethylene)ruthenium, CAS #301224-40-8), other Grubbs catalysts or similar catalysts (e.g., dichloro[1,3-bis(2-methylphenyl)-2-imidazolidinylidene](2-isopropoxyphenylmethylene)ruthenium(II), CAS #927429-61-6); dichloro[1,3-bis(2,6-isopropylphenyl)-2-imidazolidinylidene](2-isopropoxyphenylmethylene) ruthenium(II), CAS #635679-24-2); dichloro[1,3-bis(2,4,6-trimethylphenyl)-2-imidazolidinylidene](3-methyl-2-butenylidene) (tricyclohexylphosphine)ruthenium(II), CAS #253688-91-4; [2-(1-methylethoxy-0)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium, CAS #1352916-84-7, dichloro[1,3-bis(2,4,6-trimethylphenyl)-2-imidazolidinylidene][(5-isobutoxycarbonylamino)-(2-isopropoxy)benzylidene]ruthenium, CAS #1025728-57-7), Piers catalysts (e.g., dichloro(tricyclohexylphosphine)[(tricyclohexylphosphoranyl)methylidene]ruthenium(II) tetrafluoroborate, CAS #1020085-61-3); dichloro[1,3-bis(2,4,6-trimethylphenyl)-2-imidazolidinylidene][(tricyclohexylphosphoranyl)methylidene]ruthenium(II) tetrafluoroborate, CAS #832146-68-6); molybdenum carbine catalysts, such as catalysts having structures meeting the formula $Cp_2TiCl_2/RMgX$, wherein "Cp" is $\eta^5$-cyclopentadienyl, R is $CH_3$, $C_2H_5$, i-$C_3H_7$, n-$C_4H_9$, n-$C_6H_{13}$, or $C_6H_5$, and X is Cl, Br, or I; $ReCl_5/Me_4Sn$ catalyst systems; Tungsten(IV) or molybdenum(IV)-based catalysts, such as Schrock alkyldenes derived catalysts (e.g., W(C-t-Bu)(CH$_2$-t-Bu)$_3$, Mo(C-t-Bu)(CH$_2$-t-Bu)$_3$, W(CH-t-Bu)(O)(PR$_3$)$_2$Cl$_2$, W(CH-t-Bu)(O)(PR$_3$)Cl$_2$, Mo(NAr)(CH-t-Bu)(OHIPT) (Pyrrolide), and W(O)(CH-t-Bu)(OHMT)(Me$_2$Pyr)), Schrock-Hoveyda Catalyst (e.g., 2,6-Diisopropylphenylimidoneophylidene[(S)-(−)-BIPHEN]molybdenum(VI), CAS #205815-80-1); allyl silane/tungsten catalysts (e.g., catalysts consisting of WCl$_6$ and/or WOCl$_4$ and organosilicon compounds such as SiAllyl$_4$, SiMe$_2$Allyl$_2$, (iBu)$_2$Al—O—Al (iBu)$_2$), and the like. In some embodiments, the amount of catalyst is selected depending on the reaction rate desired. In some embodiments, 0.00001 to 0.10 mole of catalyst can be used per mole of monomer(s), such as 0.00005 to 0.001 mole of catalyst per mole of monomer(s).

Alternatively, metal-free conditions and/or catalysts may be used to promote the reaction. For example, the monomers can be polymerized in a suitable solvent, including polar solvents (such as THF, 2-MeTHF, DMSO, or other polar aprotic solvents known to those having ordinary skill in the art, with the benefit of the present disclosure) and non-polar solvents (such as CH$_2$Cl$_2$, toluene, or other hydrocarbon solvents like aliphatic-based solvents, such as hexane, pentane, heptane, hexanes, and the like) using an enol ether initiator (such as, ethyl propenyl ether, 1-methoxy-4-phenyl butane, or 2-cyclohexyl-1-methoxyethylene) and photoredox mediator (such as a pyrylium salt, an acridinium salt, a thiopyrylium salt, a persulfated salt, 2,4,6-tris(4-methoxyphenyl)pyrylium tetrafluoroborate or 2,3-dichloro-5,6-dicyano-1,4-benzoquinone) and further exposing the reaction mixture to blue LED light. In such embodiments, the conditions and reagents described by Goetz and Boydston, *J. Am. Chem. Soc.* 2015, 137, 7572-7575, which is incorporated herein by reference, can be adapted for use with the disclosed compounds to facilitate metal-free polymerization.

If a mixture of 3 and 4 was used, unreacted monomer 3 may be recovered and recycled, though cracking and subsequent Diels-Alder dimerization. Alternatively, isomer 3 may be removed from the mixture prior to polymerization. In exemplary embodiments, this may be achieved through conjugate addition with an amine (e.g., a water-soluble diamine, such as 1,3-diaminopropane) or other nucleophilic groups. An exemplary embodiment of this method is illustrated below in Scheme 3.

Scheme 3
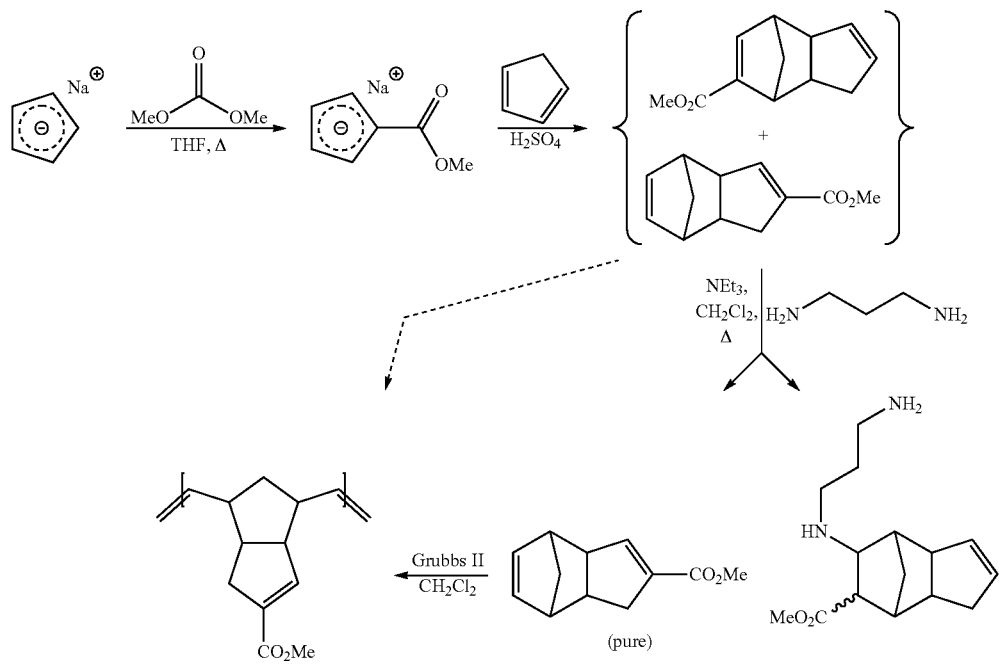
A further exemplary method for preparing disclosed materials is provided in Scheme 4 below.
Scheme 4
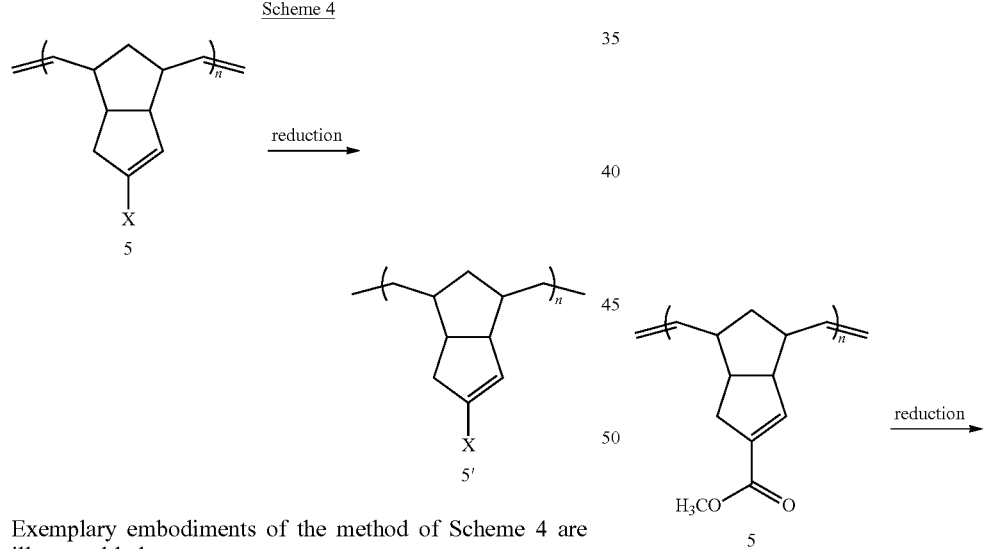
Exemplary embodiments of the method of Scheme 4 are illustrated below.
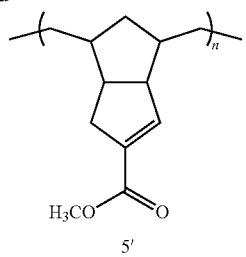
-continued
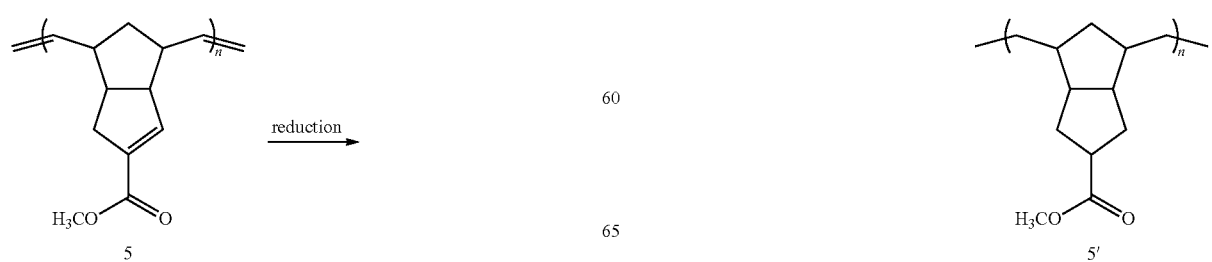

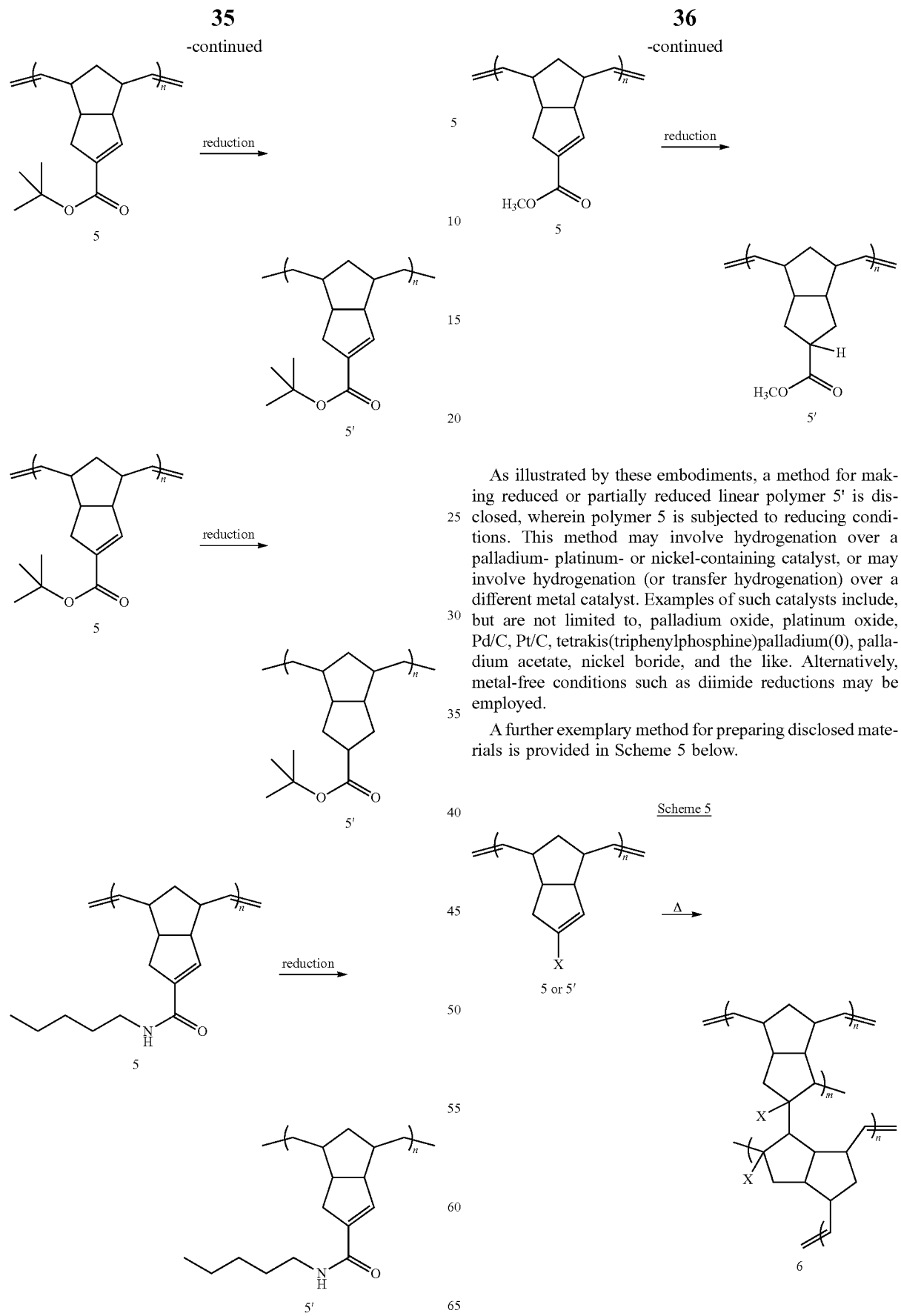

As illustrated by these embodiments, a method for making reduced or partially reduced linear polymer 5' is disclosed, wherein polymer 5 is subjected to reducing conditions. This method may involve hydrogenation over a palladium- platinum- or nickel-containing catalyst, or may involve hydrogenation (or transfer hydrogenation) over a different metal catalyst. Examples of such catalysts include, but are not limited to, palladium oxide, platinum oxide, Pd/C, Pt/C, tetrakis(triphenylphosphine)palladium(0), palladium acetate, nickel boride, and the like. Alternatively, metal-free conditions such as diimide reductions may be employed.

A further exemplary method for preparing disclosed materials is provided in Scheme 5 below.

Exemplary embodiments of the method of Scheme 5 are illustrated below.

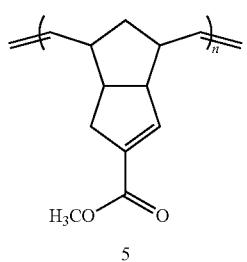

5

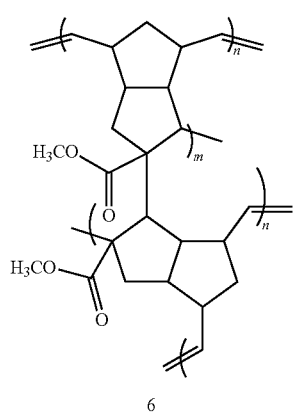

6

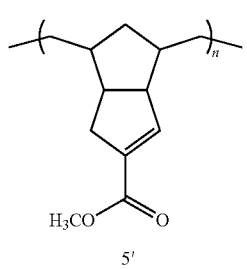

5'

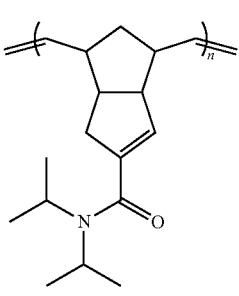

5

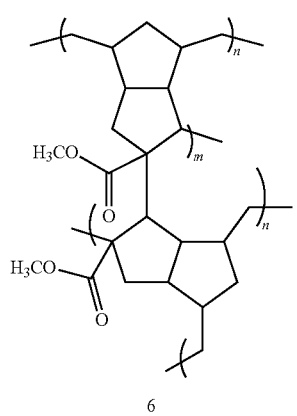

6

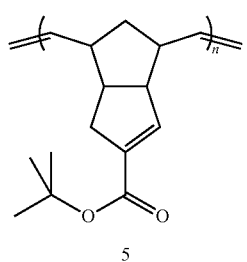

5

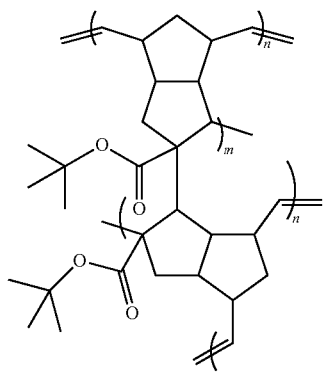

6

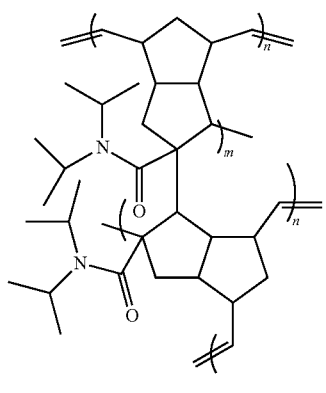

6

As illustrated by these embodiments, a method for thermally curing linear polymer 5 or 5' is disclosed, wherein the linear polymer is heated to induce chemical crosslinks. Alternative methods for curing may involve treatment with ultraviolet or other wavelengths of light, in the presence or absence of radical initiators or sensitizers. The crosslinked polymer may be described by structure 6, or may be described by other chemical formulae.

A further exemplary method for preparing disclosed materials is provided in Scheme 6 below.

Scheme 6
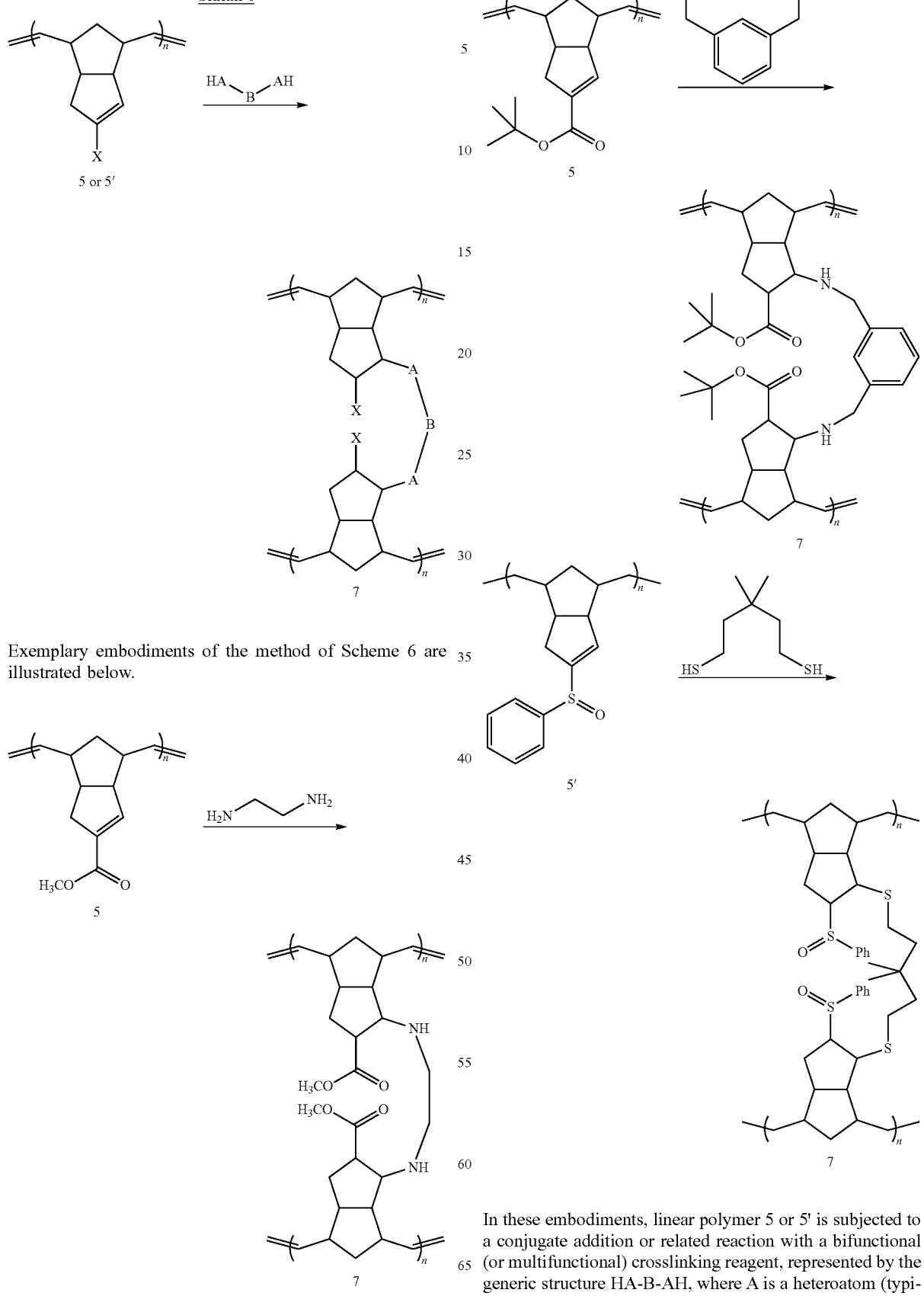
Exemplary embodiments of the method of Scheme 6 are illustrated below.
In these embodiments, linear polymer 5 or 5' is subjected to a conjugate addition or related reaction with a bifunctional (or multifunctional) crosslinking reagent, represented by the generic structure HA-B-AH, where A is a heteroatom (typically O, S or NH) and B is any suitable linking group.

A further exemplary method for preparing disclosed materials is provided in Scheme 7 below.
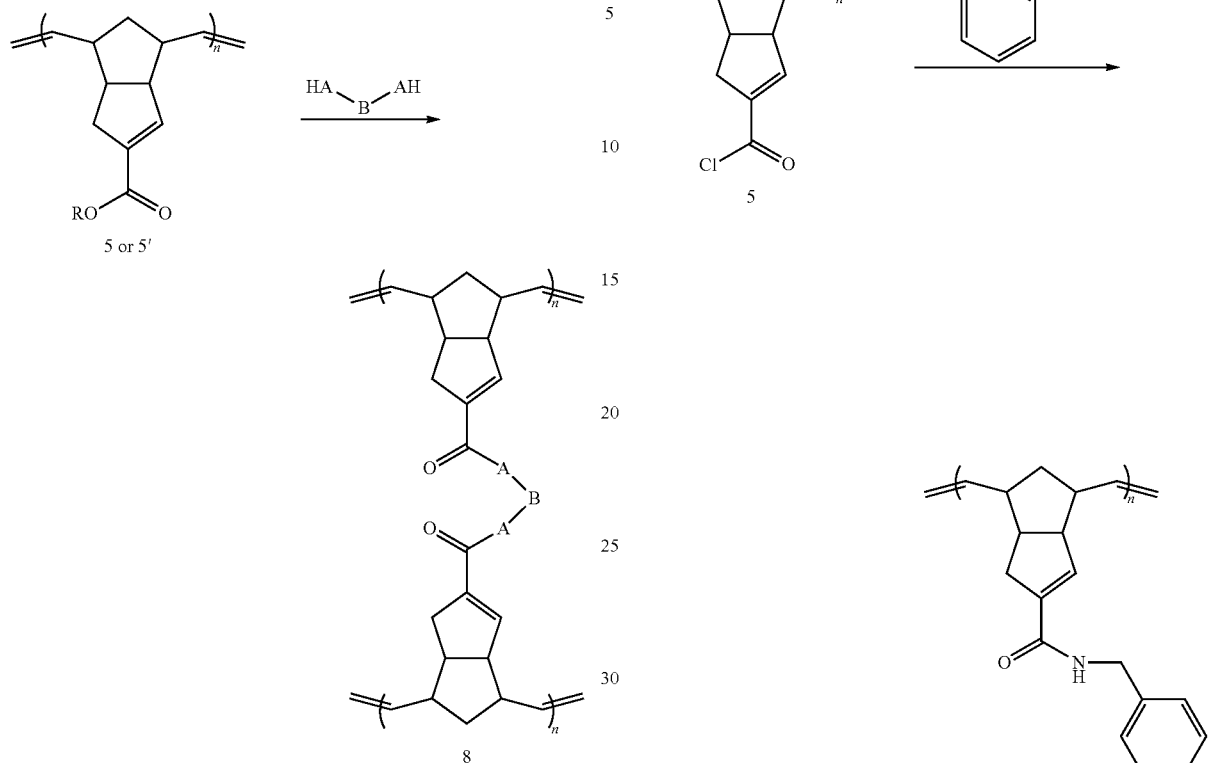
Exemplary embodiments of the method of Scheme 7 are illustrated below.
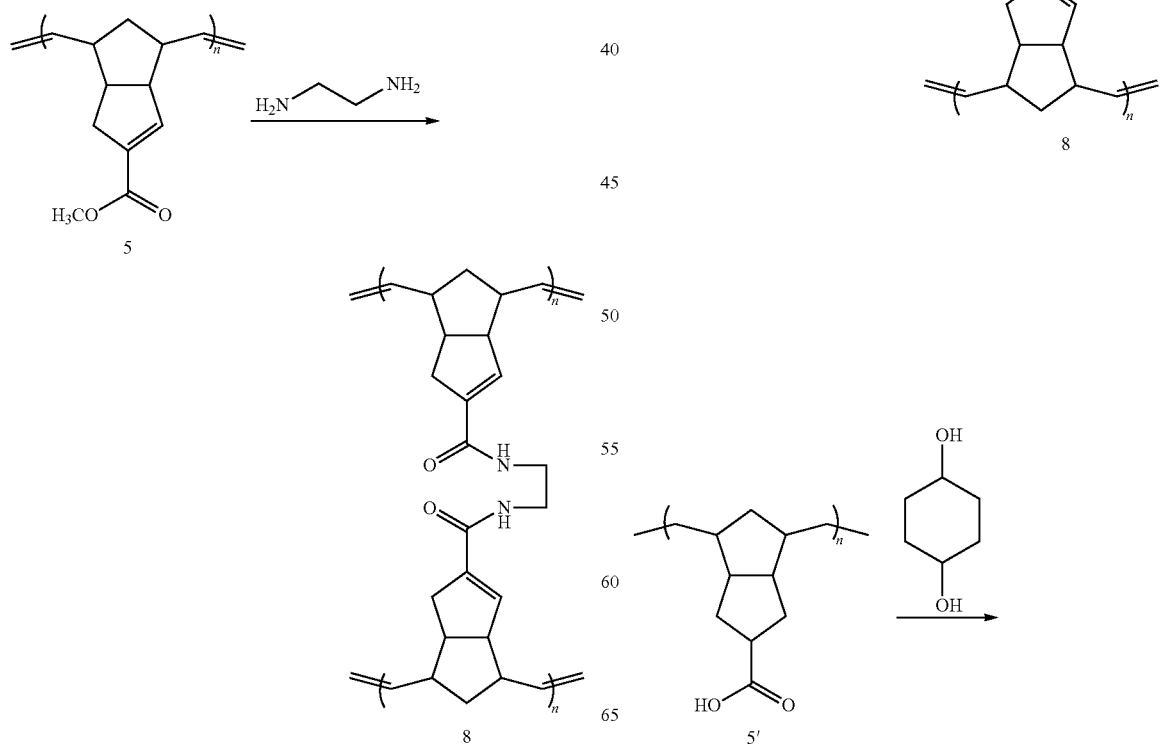

represented by the generic structure HA-B-AH, where A is a heteroatom (typically O, S or NH) and B is any suitable linking group.

A further exemplary method for preparing disclosed materials is provided in Scheme 8 below.

Scheme 8

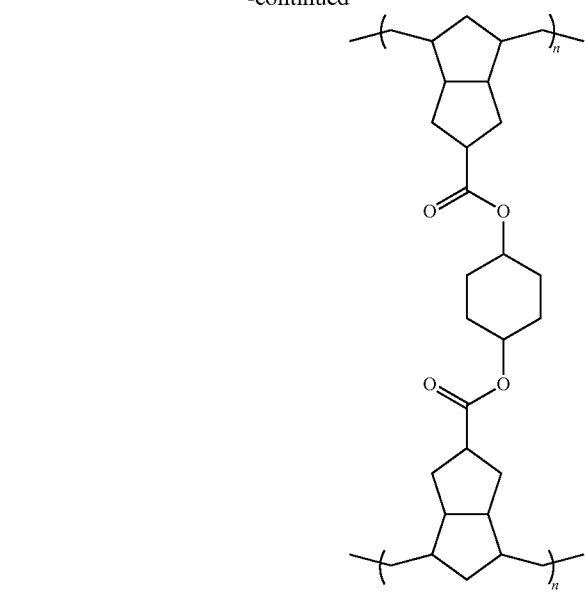

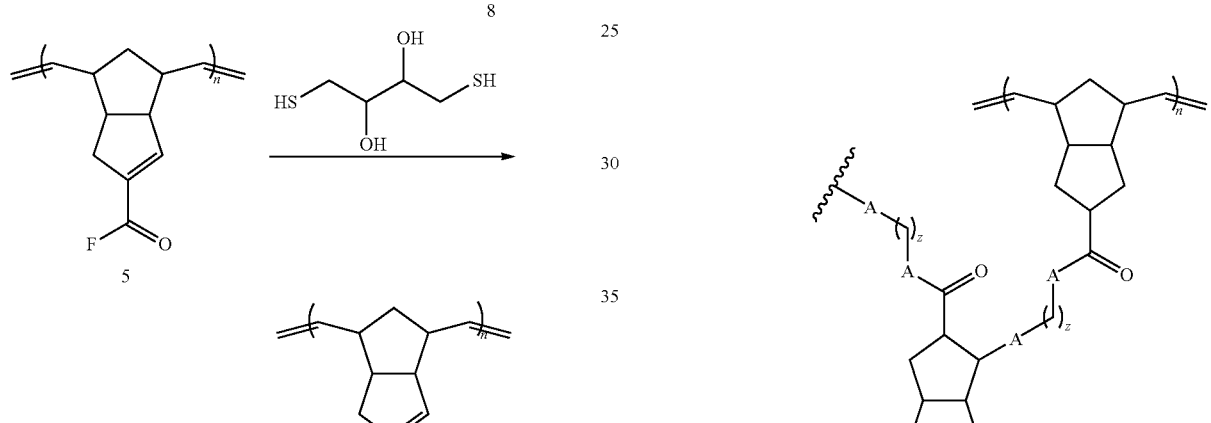

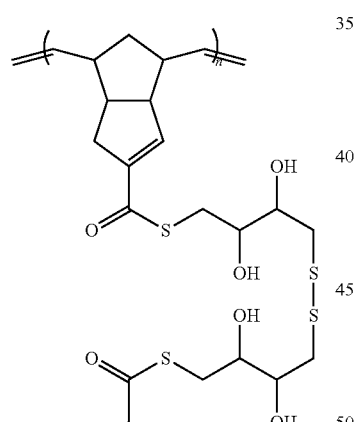

Exemplary embodiments of the method of Scheme 8 are illustrated below.

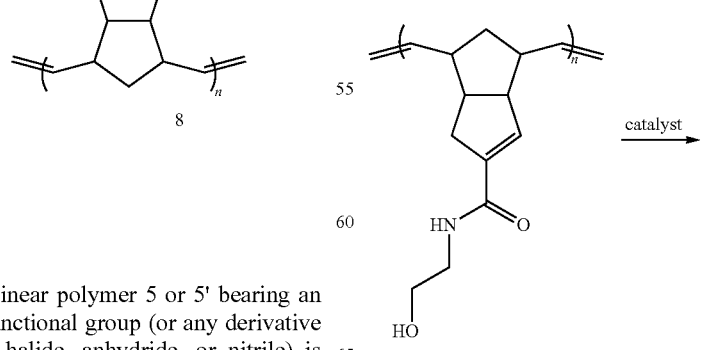

In these embodiments, a linear polymer 5 or 5' bearing an ester or carboxylic acid functional group (or any derivative thereof, such as an acyl halide, anhydride, or nitrile) is cross-coupled through the carbonyl functional group, using a bifunctional (or multifunctional) crosslinking reagent,

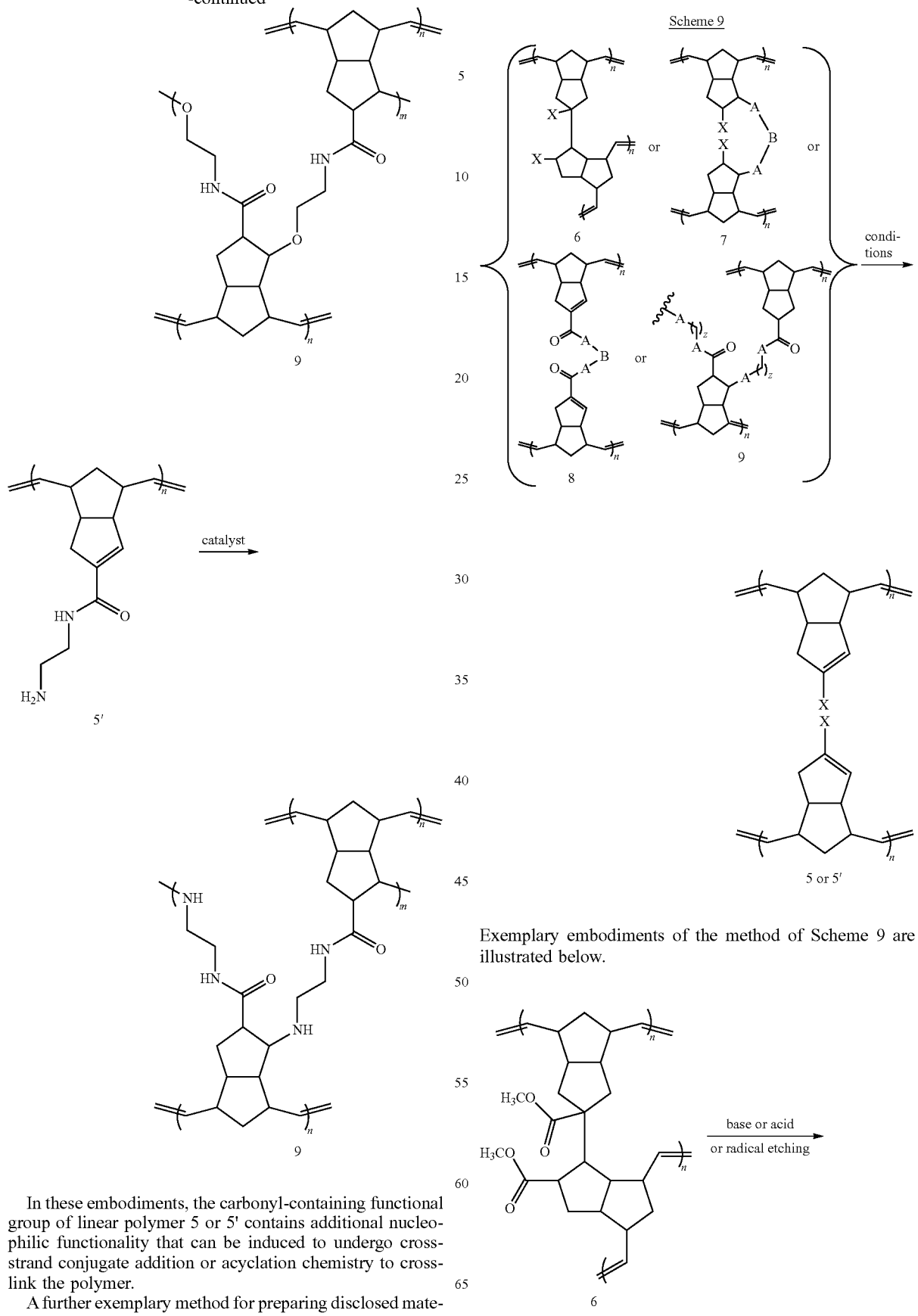

In these embodiments, the carbonyl-containing functional group of linear polymer 5 or 5' contains additional nucleophilic functionality that can be induced to undergo cross-strand conjugate addition or acylation chemistry to crosslink the polymer.

A further exemplary method for preparing disclosed materials is provided in Scheme 9 below.

Exemplary embodiments of the method of Scheme 9 are illustrated below.

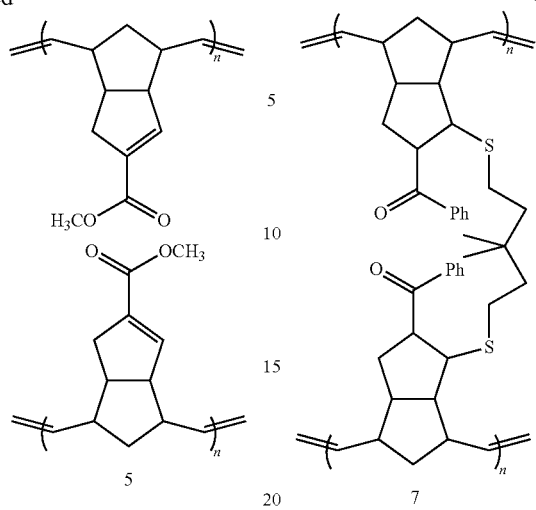
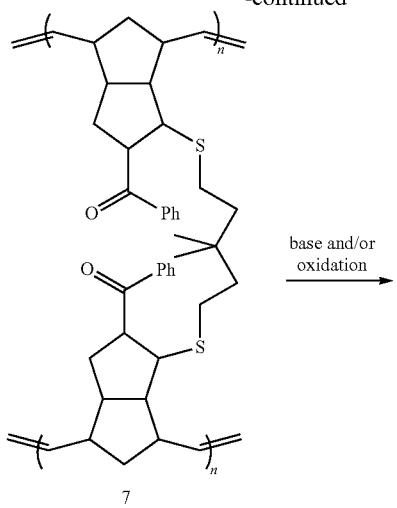
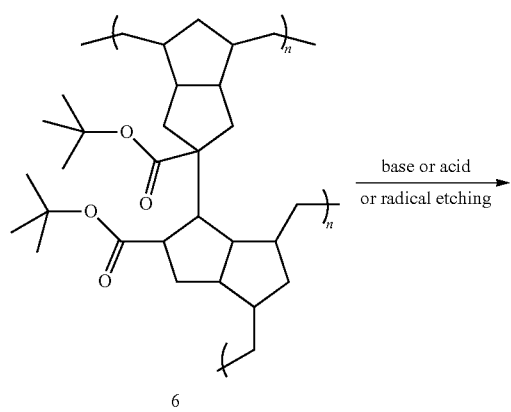
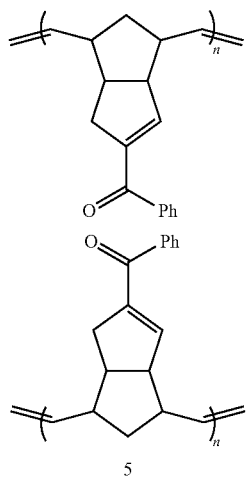
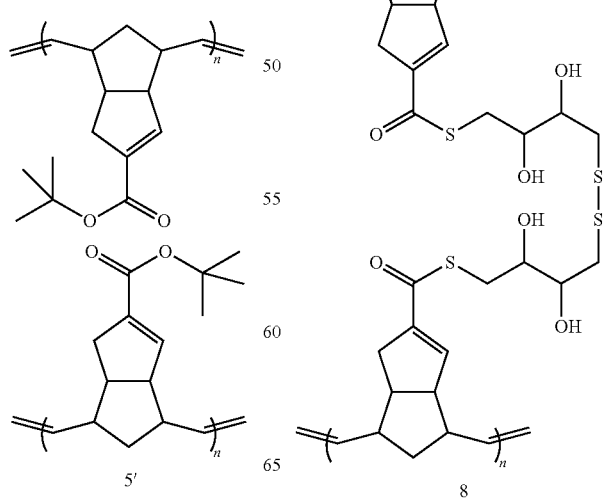

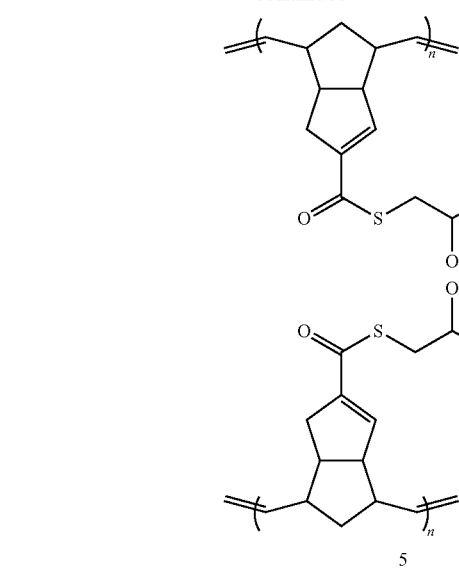

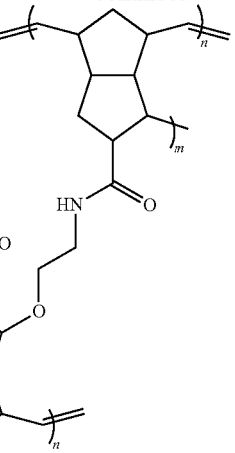

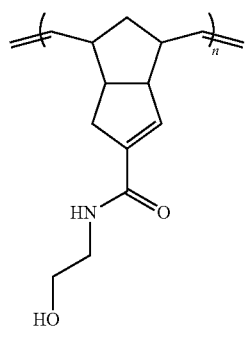

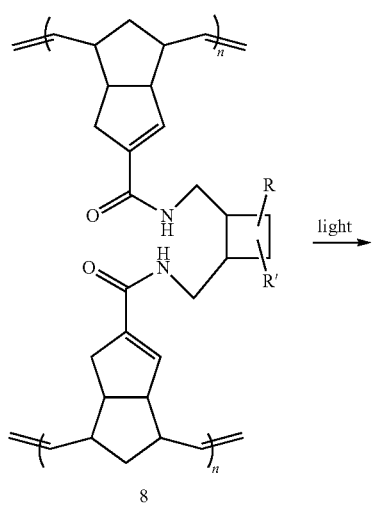

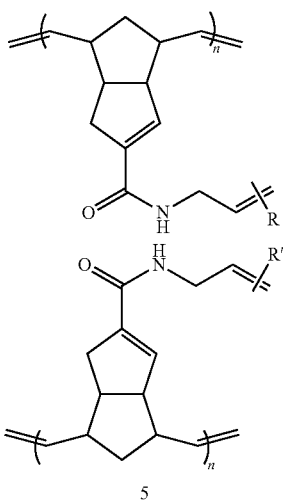

In these embodiments, interstrand (or intrastrand) cross-links such as those illustrated by structures 6, 7, 8, and 9, can be reversed by treatment under specific radical conditions, oxidative conditions, enzymatic conditions, electromagnetic radiation conditions, reductive conditions, acidic conditions, basic conditions, or metal-catalyzed conditions to regenerate some form of the uncrosslinked (or less crosslinked) linear polymer 5 or 5'. In some embodiments, reductive conditions (e.g. sodium borohydride or similar reagents, or phosphines, or thiols, or electrochemical reduction) can be used to cleave possible disulfide linkers for certain polymers (e.g., compounds 7 or 8). In some embodiments, basic conditions (e.g. NaOH, KOH, $K_2CO_3$, amines, etc.) can be used to trigger β-elimination from the polymers (e.g., compounds 7-9), or to trigger retro-Michael addition from the polymers (e.g., compound 6). In some embodiments, acidic aqueous solutions (e.g., water containing HCl or $H_2SO_4$ or any other acid) can be used to trigger hydrolysis of amide or ester groups in the polymers (e.g., compounds 8 or 9). In yet additional embodiments, light can be used to trigger pericyclic reactions (e.g., retro-[2+2] additions) that lead to the fragmentation of the polymers (e.g., compounds 7 or 8). In yet additional embodiments, free radicals (e.g., free radicals produced from exposure of $Et_3B$ to air, or generated through photoredox catalysis, etc.) can be used to trigger β-fragmentation pathways in the polymers (e.g., compounds 6-9).

A further exemplary method for preparing disclosed materials is provided in Scheme 10 below.

Scheme 10

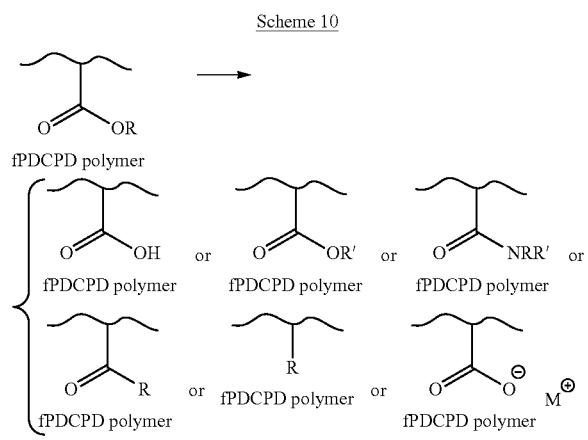

In this embodiment, linear or crosslinked polymer, prepared by any of the methods described above, or by similar strategies, is chemically treated to convert a functional group present on the polymer into another type of functional group. Such chemical alterations may include hydrogenation reactions, esterification reactions (e.g., reaction of an ester with an excess of an alcohol solvent to generate a different ester, with different properties), hydrolysis reactions (e.g., treatment of esters or amides with aqueous base or acid to produce the corresponding carboxylic acids or carboxylate salts), condensation reactions (e.g., reaction of a carboxylic acid-containing polymer with an amine in the presence of a peptide-coupling reagent, such as EDC or DCC, to produce the corresponding amide), metal-mediated coupling or decarboxylation reactions, photochemical reactions, additions of nucleophilic species (e.g., addition of a Grignard or organolithium reagent to an ester-containing polymer to provide the corresponding ketone or tertiary alcohol), radical species, or electrophilic species, or other transformations that will be recognized by those skilled in the art, with the benefit of the present disclosure, to be conceptually similar to those summarized here.

Another aspect of the present disclosure relates to the disclosed molecules and methods wherein the surface area of the polymer is modified to enhance stability of the polymer (such as against atmospheric oxygen) and/or to control the surface energy of the polymer to improve adhesion or other properties. Yet another aspect of the present disclosure relates to modifying the material after polymerization. For example, a disclosed polymer, copolymer, or a crosslinked polymer can be modified after polymerization such that the polymer is exposed to a chemical process or physical process capable of converting a functional group of the polymer to enhance stability (such as against atmospheric oxygen) and/or to control the surface energy of the polymer to improve adhesion or other properties. In yet additional embodiments, the surface energy of the polymer can be modified to improve adhesion or other properties without having to expose the polymer to additional chemical treatments, such as those described herein.

The monomers, linear polymers or crosslinked polymers (including copolymers) described herein can be used for manufacturing processes, including injection molding, resin transfer molding, reaction injection molding (RIM), sheet molding compound (SMC) processes, bulk molding compound (BMC) processes, glass reinforced plastic (GRP) processes, and other processes used in polymer manufacturing. In some embodiments, a premade polymer embodiment can be added to a mold under pressure, such as in an injection molding method. The polymer within the mold can then be cured (e.g., thermally cured) to provide the molded polymer. In other particular disclosed embodiments, one or more monomer embodiments described herein can be used in a reaction injection molding process to provide a molded object. The monomer embodiment can be polymerized during the reaction injection molding process to provide a polymer as described herein and wherein the polymer is formed into a desired shape. In some embodiments, the reaction injection molding method can comprise combining a monomer embodiment and a catalyst in a mold and allowing sufficient time for a desired level of polymerization to occur. The method can further comprise curing (e.g., thermal curing, such as curing at 120° C. to 200° C., such as 135° C. to 180° C., or 150° C. to 180° C., with representative temperatures being 135° C., 150° C., or 180° C.) the polymer, either within the mold or outside the mold. The curing step also can be used to control the color of the polymer. In other embodiments, a pre-formed linear polymer (or copolymer) or a crosslinked-polymer (or copolymer) can be used in a reaction injection molding process to provide a molded object comprising the polymer.

Another aspect of this disclosure relates to using the above mentioned monomers, linear polymers or crosslinked polymers (including copolymers) in foams, gels, aerogels, films or coatings. In some embodiments, a particular monomer embodiment (such as a monomer having a structure satisfying the formula illustrated below) can be combined with another monomer embodiment, such as cyclopentadiene, and/or other polymerizable moiety (as described in definitions provided herein) and then reacted to form a copolymer.

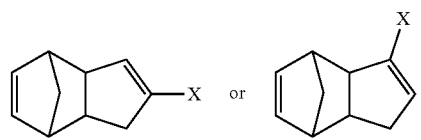

The resulting copolymer can exhibit material properties (e.g., physical and/or mechanical properties) that are different from that of a polymer made from each of the single monomeric species used to make the copolymer. In some embodiments, combining different monomers to provide a copolymer can be used to provide a copolymer material that has a desired hardness, flexibility, elongation modulus, and other such material properties. In particular disclosed embodiments, the copolymer can be evaluated in terms of its Vickers hardness, Rockwell hardness, or other hardness measurements that are applied to polymeric materials used in industrial applications. Solely by way of example, a first monomer and a second monomer can be combined at a particular ratio of first monomer:second monomer sufficient to obtain a copolymer having a desired material property. In some embodiments, a mole fraction of 10:1 to 1:10 (first monomer:second monomer) can be used, such as 10:1 (first monomer:second monomer), 5:1 (first monomer:second monomer), 1:1 (first monomer:second monomer), or 1:2 (first monomer:second monomer). In a representative embodiment, a functionalized dicyclopentadiene monomer (e.g., an ester-functionalized monomer) is combined with a dicyclopentadiene monomer to provide a copolymer as illustrated below.

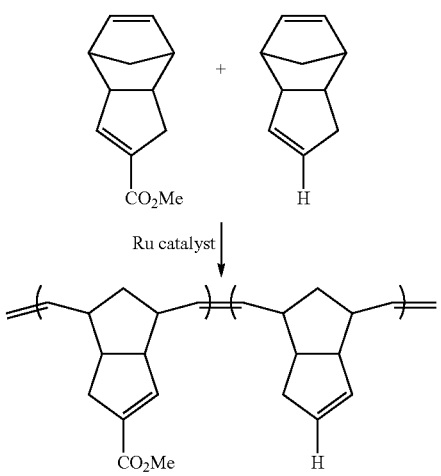

A further aspect of the present disclosure relates to the disclosed molecules and methods wherein chemical derivatizations of the functional groups within the polymer are used to attach other chemical entities, such as pharmaceutical agents (e.g., antimicrobial agents or antifungal agents), stimuli-responsive agents, dyes, sensors, or the like, to the polymer material. In yet additional embodiments, such functionalized polymers may be used as drug-delivery agents or sensing materials. For example, an anti-cancer agent (e.g., paclitaxel, SN38, or the like) can be attached to a polymer embodiment disclosed herein through a functional group of the polymer (e.g., an X group of the polymer or an alkene moiety of the polymer). In additional embodiments, a stress-reporting molecule, such as a spiropyran, can be attached as a sensor motif to detect and report structural changes to the polymer. Such molecules can be attached through a functional group of the polymer (e.g., an X group of the polymer or an alkene moiety of the polymer).

V. Examples

The following examples are provided to illustrate certain features of working embodiments of the present disclosure. A person of ordinary skill in the art will appreciate that the disclosure is not limited to such features.

Example 1

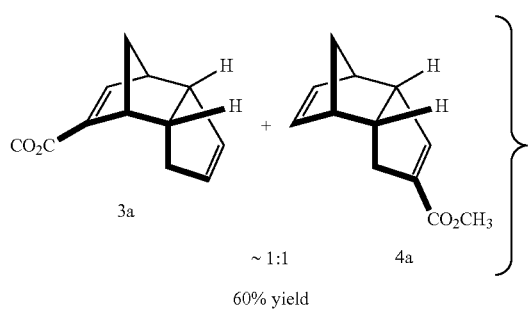

Sample Protocol:

A flame-dried round bottom flask fitted with an oven-dried condenser was charged with 7 mL sodium cyclopentadienylide solution (2 M in THF, 14 mmol). To this solution was added 5.9 mL dimethylcarbonate (70 mmol), at room temperature with stirring. The reaction mixture was heated to reflux for six h, then cooled to room temperature. The mixture was concentrated in vacuo. To the resulting solid was added iPrOH (to 0.33 M), 0.41 mL sulfuric acid (0.55 equiv, 7.7 mmol) and 2.35 mL of freshly cracked cyclopentadiene (28 mmol) at room temperature with stirring. Acidification was marked by a brown to orange color change. The solution was heated to 50° C. overnight. The reaction mixture was concentrated in vacuo and the resulting oil was dissolved in toluene, and loaded onto a silica gel column. Elution with hexanes-ethyl acetate provided 1.60 g of a mixture of 3a and 4a (60%). $^1$H NMR for 3a (300 MHz, CDCl$_3$) δ 6.84 (d, J=3.5 Hz, 1H), 5.45-5.50 (m, 2H), 3.72 (s, 3H), 3.35-3.40 (m, 1H), 3.28-3.31 (m, 1H), 3.01-3.04 (m, 1H), 2.23 (ddq, J=18.3, 10.3, 1.9 Hz, 1H), 1.70-1.77 (m, 1H), 1.64 (dt, J=8.2, 1.8 Hz, 1H), 1.30 (d, J=8.2 Hz, 1H). $^{13}$C NMR (75 MHz, CDCl$_3$) δ 166.9, 148.5, 133.1, 133.1, 130.8, 54.2, 51.4, 50.6, 47.1, 46.4, 40.8, 34.2; $^1$H NMR for 4a (300 MHz, CDCl$_3$) δ 6.54 (d, J=2.3 Hz, 1H), 6.03 (dd, J=5.7, 3.0 Hz, 1H), 5.93 (dd, J=5.7, 3.0 Hz, 1H), 3.68 (s, 3H), 2.92-2.96 (m, 1H), 2.89-2.92 (m, 1H), 2.80-2.88 (m, 2H), 2.42 (ddt, J=17.3, 10.3, 2.0 Hz, 1H), 1.91 (dtd, J=17.3, 4.0, 2.0 Hz, 1H), 1.49 (dt, J=8.2, 1.7 Hz, 1H), 1.30 (d, J=8.2 Hz, 1H). $^{13}$C NMR (75 MHz, CDCl$_3$) δ 166.7, 144.5, 137.1, 135.7, 133.0, 55.0, 51.3, 50.3, 46.3, 45.6, 41.3, 33.6; IR (cm$^{-1}$, film) 2955, 1732, 1717, 1634, 1439, 1268, 1096, 735. GCMS 190, 125, 93, 66 m/z observed for four isomeric species in a ratio of 1:0.6:0.17:0.015. HRMS (ESI) calcd for [M+Na]$^+$ C$_{12}$H$_{14}$O$_2$Na, 213.08861, found 213.08864.

Additional Information:

In some examples, sodium cyclopentadienylide was prepared in house from cyclopentadiene and sodium hydride (NaH) or from cyclopentadiene and sodium metal. Neither of these alterations to the above procedure resulted in a substantive difference to the outcome of the reaction.

The direct preparation of sodium cyclopentadienylide from uncracked dicyclopentadiene and sodium metal is also known to proceed efficiently, and may represent an efficiency for large scale production. The appropriate protocol, incorporated here by reference, can be found in Panda et al., *Organometallics* 2003, 22, 877-878. For example, in some embodiments, freshly cut sodium (e.g., 0.43 mol) or potassium (e.g., 33.8 mol) is added to dicyclopentadiene (e.g., 400 mL or 50 mL) at room temperature. On heating, the solution turns blue (around 35° C.). Before the sodium is completely molten, the solution may slowly discolor. The mixture is heated for 6 hour to 160° C. On heating, a white solid precipitates. When the alkali metal is quantitatively consumed, the dihydrogen evolution stops. To ensure a quantitative conversation, the heating can be continued for another 30 min after the dihydrogen evolution end. The reaction mixture is filtered, and the white residue is washed with three 50 mL portions of n-pentane and dried in vacuo. The unreacted dicyclopentadiene can be used again for the same reaction.

In some examples, the intermediate salt 2a was isolated by precipitation and was partially purified by washing with nonpolar solvents. The appropriate protocol, incorporated here by reference, can be found in Chen et al., *J. Org. Chem.* 2015, 80, 8979-8989.

In some examples, the preparation of 3a and 4a was accomplished on 45 gram scale, with no loss of yield or product purity.

In some examples, the preparation of 3a and 4a was accomplished on 468 gram scale, with no loss of yield or product purity.

In some examples, 3a and 4a were isolated by distillation rather than column chromatography. This may represent an efficiency for large scale production. In some embodiments, a mixture of monomers can be treated with an aqueous work-up protocol and/or vacuum-facilitated removal of unreacted dicyclopentadiene and then subsequently converted to the desired polymer without additional purification steps (such as column chromatography). In a particular example, 3a and 4a were not fully purified prior to use in subsequent steps. Instead, gentle distillation (50° C. at 0.1 mm Hg) was used to remove residual dicyclopentadiene. The remaining material—containing predominantly 3a and 4a together with other unreactive isomers and impurities—could be used directly for polymerization or for other transformations. The absence of purification steps represents a further efficiency for large scale production.

In some examples, 3a and 4a (together with two very minor isomers) were found to have separate boiling points as determined by GC-MS. This indicates that the separation of 3a and 4a by fractional distillation is also achievable, and the use of such methods also is disclosed herein.

In some examples, 3a was selectively degraded by conjugate addition of an amine. This method likewise allows for the isolation of purified 4a. This method was used to unambiguously assign the spectra for the two species. In some embodiments, the amine can be a diamine. In particular embodiments, the amine is a water-soluble diamine, such as 1,3-diaminopropane.

Example 2

Sample Protocol:

To a mixture of 3a and 4a (190 mg, 1 mmol) in 3 mL of DCM was added 8 mg Grubbs second generation catalyst (monomer:catalyst=40:1). See FIG. 2 for an exemplary reaction scheme. The mixture was allowed to stir at room temperature for 40 min. To this solution was added 1 mL ethyl vinyl ether. The reaction was stirred for an additional 1 h, after which 10 mL of diethyl ether was added. White precipitate indicated formation of the polymer. While diethyl ether was used in this example to precipitate the polymer, other solvents can be used to perform the precipitation step, including, but not limited to, an aliphatic-based solvent, such as heptane, hexane, pentane, or the like. The resulting mixture was centrifuged at 3000 rpm and 4° C. for 5 min. The polymer 5a was isolated as a precipitate (64 mg, 90% based upon the amount of 4a in the starting mixture) and unreacted 3a was obtained in the ether supernatant. $^1$H NMR (500 MHz, CDCl$_3$) δ 6.52-6.65 (br, 1H), 5.22-5.55 (br, 2H), 3.69-3.75 (br, 3H), 3.33-3.42 (br, 1H), 2.85-3.02 (br, 2H), 2.47-2.73 (br, 2H), 1.59-1.76 (br, 1H), 1.20-1.34 (br, 1H). $^{13}$C NMR (75 MHz, CDCl$_3$) δ 165.3, 143.9, 136.6, 131.5, 130.7, 56.0, 51.4 (the remaining carbon resonances appeared as overlapping signals from 47.3 to 34.2 ppm).

Additional Information:

In some examples, a 100:1 monomer:catalyst loading was employed. In other examples, a 400:1 monomer:catalyst loading was employed. In still other examples, a 1000:1 monomer:catalyst loading was employed. Lower catalyst loadings require longer times for the polymerization reaction to proceed to completion, and result in higher molecular weight polymers.

In some examples, Grubbs third generation catalyst was employed in place of the catalyst described above. In other examples, the Umicore-M73 SIMes catalyst was employed in place of the catalyst described above.

In some examples, hexanes were used in place of the diethyl ether described above, to precipitate the polymer product. In other examples, heptane was used in place of the diethyl ether described above, to precipitate the product.

In some examples, the product polymer was filtered rather than centrifuged.

Figure 2:
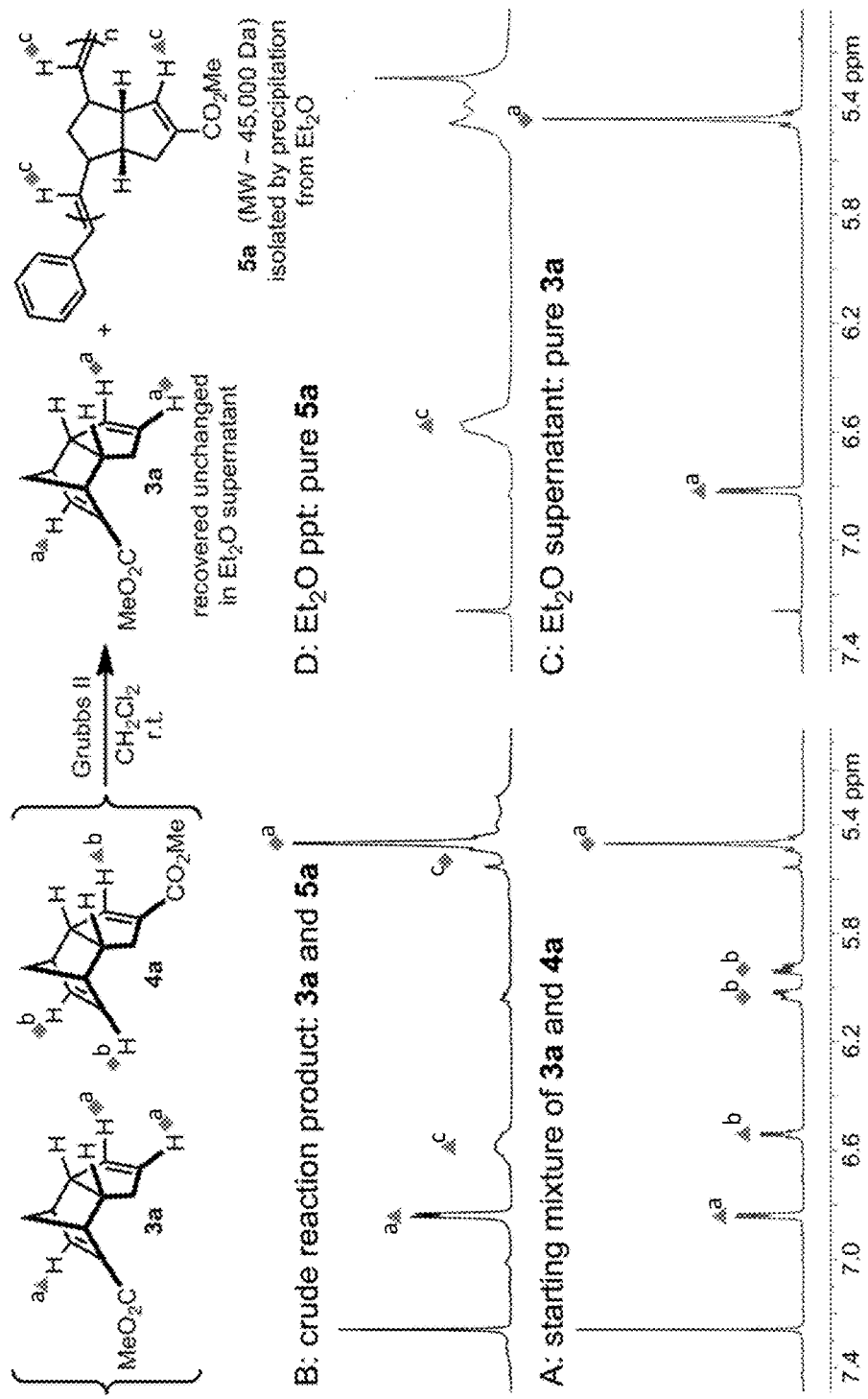
FIG. 2 illustrates proton NMR spectra for a representative method of making a polymer described herein.

In reference to FIG. 2, polymer formation was indicated by broadening of the NMR signals (particularly for the downfield signal in 4a corresponding to the electron-deficient alkene C—H) and an upfield shift for the protons on the unfunctionalized olefin (corresponding to the formation of a less strained alkene). As anticipated, compound 3a was completely unreactive under the conditions employed. Indeed, even when the reaction was repeated at higher temperatures (refluxing benzene or toluene) no polymer arising from compound 3a was observed.

Removal of the solvent and washing of the product residue with diethyl ether (or other solvents, as described herein) allowed for near-complete extraction of unreacted 3a from the less soluble polymer. Although evidently insoluble in ethereal solvent, polymer 5a proved to be completely soluble in both chlorinated solvents and THF, which facilitated product characterization.

Recycling of carboxylated cyclopentadienes like recovered 3a back to the building blocks 1 and 2a can be utilized if desired.

The molecular weight of the polymer (estimated by comparative NMR integration of the phenyl end-group to the downfield vinylic C—H of the polymer repeating unit) was ~45,000 Da when prepared as described above, and this value could be tuned somewhat by alteration of the reaction conditions. No evidence whatsoever for the existence of any crosslinks in freshly prepared polymer was observed.

Product 5a is somewhat air-sensitive (see Example 4, below) and the resulting oxidative crosslinks complicate its characterization by GPC methods. Nonetheless GPC experiments with a freshly-prepared (~4-hour-old) sample of 5a revealed Mw and Mn values that were consistent with the molecular weight determined by NMR. The following data were obtained from samples at 1 and 2 mg/mL:

1 mg/mL sample: Mw=94445 Da, Mn=39824 Da, PDI=2.37, dn/dc=0.103;

2 mg/mL Sample: Mw=93290 Da, Mn=47684 Da, PDI=1.96, dn/dc=0.108.

Figure 3A:
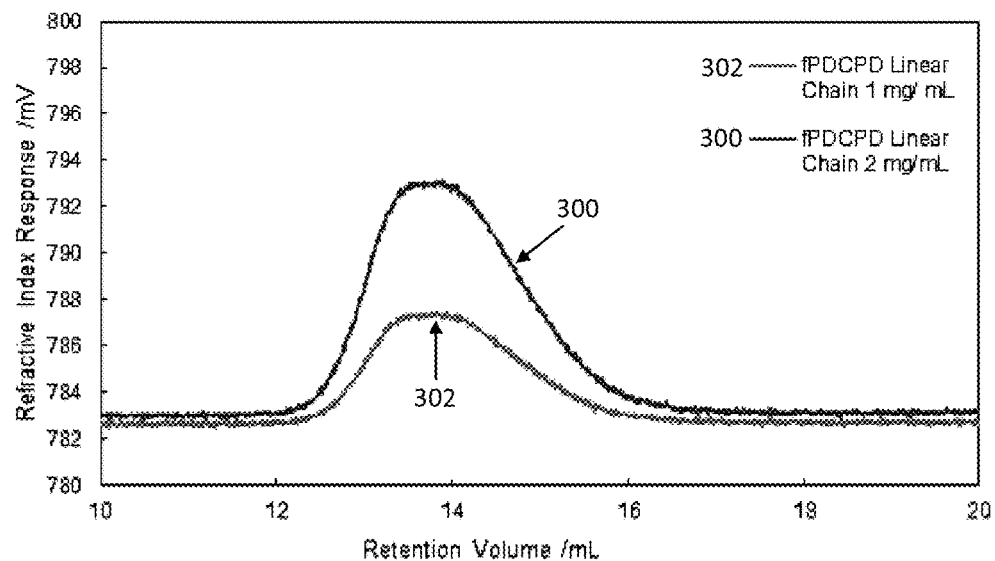
FIGS. 3A-3B are gel permeation chromatography (GPC) traces obtained using refractive index detection methods (FIG. 3A) and low angle light scattering ("LALS") detection methods (FIG. 3B) to analyze linear polymers described herein at different concentrations (300=2 mg/mL and 302=1 mg/mL).
Figure 3B:
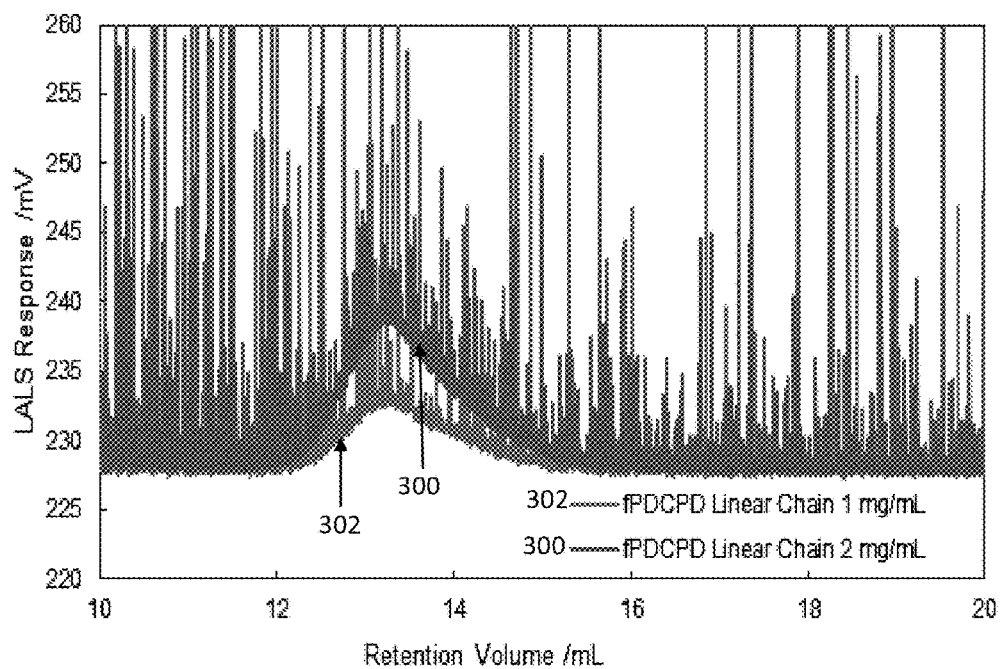

The original GPC traces are shown in FIGS. 3A and 3B (FIG. 3A=refractive index detection; FIG. 3B=low angle light scattering detection).

Example 3

Figure 4:
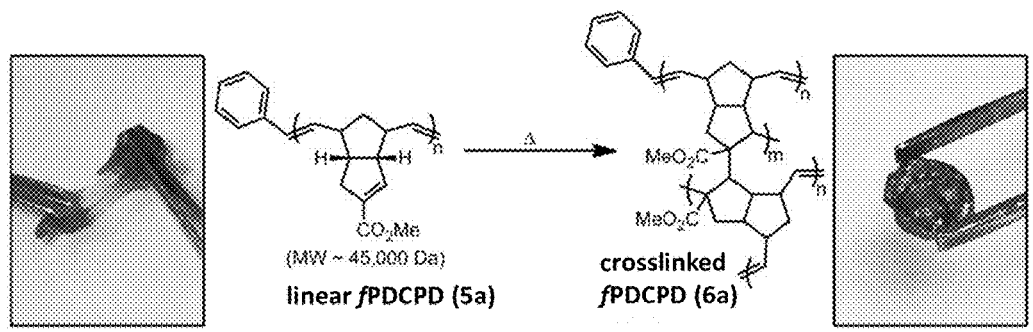
FIG. 4 provides a photographic image of a polymer embodiment and a corresponding crosslinked polymer, along with a corresponding reaction scheme.
Figure 5:
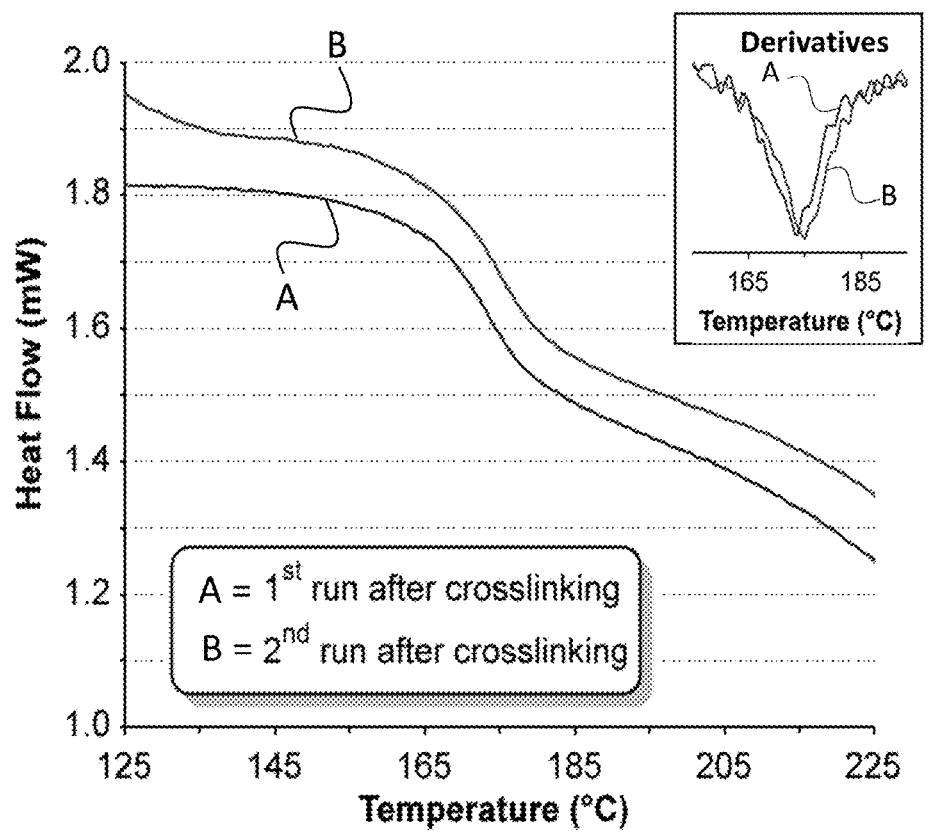
FIG. 5 is a graph of heat flow as a function of temperature illustrating results obtained from analyzing a polymer embodiment using differential scanning calorimetry thermal analysis.

Sample Protocol:

To demonstrate that polymer 5 could be crosslinked under identical conditions to its unfunctionalized congener, an oven dried vial was charged with 5a under an argon atmosphere. The sample was heated to 180° C. overnight. A hard, tough, and insoluble material 6a was obtained, as illustrated in FIG. 4. DSC data for 6a revealed a $T_g$ value of 172±3° C. This is the highest $T_g$ reported for any unaged polydicyclopentadiene, and is consistent with the structure shown above, where crosslinking results in the formation of quaternary centers. These increase the $T_g$ due to increased steric crowding and therefore reduced rotational freedom within the polymer. DSC data leading to the assignment of $T_g$ (asterisk) is illustrated in FIG. 5.

Additional Information:

The color in the samples shown in FIG. 4 is due to trapped ruthenium catalyst; for the preparation of colorless polymer films, see below.

In some examples, the thermal curing time was systematically varied from 30 minutes up to 5 days. In other examples, the crosslinking temperature was systematically varied from 100° C. up to 200° C. The curing temperature and times can be used to control the crosslinking density. For example, in one embodiment, a curing temperature of 200° C. did not provide a completely crosslinked product, whereas using a lower temperature for one day and up to five days provided a product with much higher crosslinking. The extent of crosslinking was determined by evaluating the effect of temperature and/or time on a singlet peak at 165 ppm in the $^{13}$C-NMR of the product, which corresponds to the carbonyl carbon of the product; at higher crosslinking levels, this peak was nearly completely absent and a new broad peak was observed at 175 ppm (which currently is believed to correspond to a carbon atom of a pivalate-type carbonyl group). In an additional example, FT-IR and Raman spectroscopy analysis were used to monitor olefin reactivity and conversion. For example, in one embodiment trends were observed in the carbonyl/alkene region of the FT-IR spectra, specifically, a C(H) stretch at 1635 cm$^{-1}$ clearly diminished upon crosslinking, as did the corresponding methacrylate C=O stretch. At the same time, a new carbonyl stretch at higher wavenumbers was observed, which was consistent with the formation of the pivalate-type carbonyl function that would be expected as a result of olefin addition processes. A more pronounced (and broad) olefin stretch at lower wavenumbers that would be most consistent with the introduction of greater strain into the backbone alkenes as the pendant methacrylate groups undergo crosslinking also was observed. As such, supportive data that can be used to confirm crosslinking for this particular embodiment (and which can be extrapolated to other embodiments based on general knowledge in the art with the benefit of the present disclosure) includes, but is not limited to, the appearance of pivalate-type signals in both the $^{13}$C{$^1$H} NMR and IR data as well as the very high glass transition temperature for the cross-linked ester-containing polymer, relative to unmodified polydicyclopentadiene (as discussed below).

Crosslinking of the linear polymer 5a inside the DSC apparatus allowed for the direct observation of the cross-linking step as an endothermic event at ca. 145° C. Rerunning of the now-crosslinked polymer by DSC confirmed that this step was not reversible under thermal conditions. Details are available in Chen et al., *ACS Omega*, 2016, 1, 532-540, which is incorporated here by reference. For example, freshly prepared linear polymer can be dried under vacuum and transferred directly to the DSC device under a nitrogen atmosphere. DSC and TGA measurements can be conducted on a TA Instruments Q600 SDT simultaneous thermal analyzer with samples being placed in an aluminum oxide crucible, and referenced against an empty aluminum oxide crucible. In some embodiments, data is collected with a ramp rate of 5° C./min following temperature equalization at 50° C. under a nitrogen atmosphere flowing at 100 mL/min.

Figure 12:
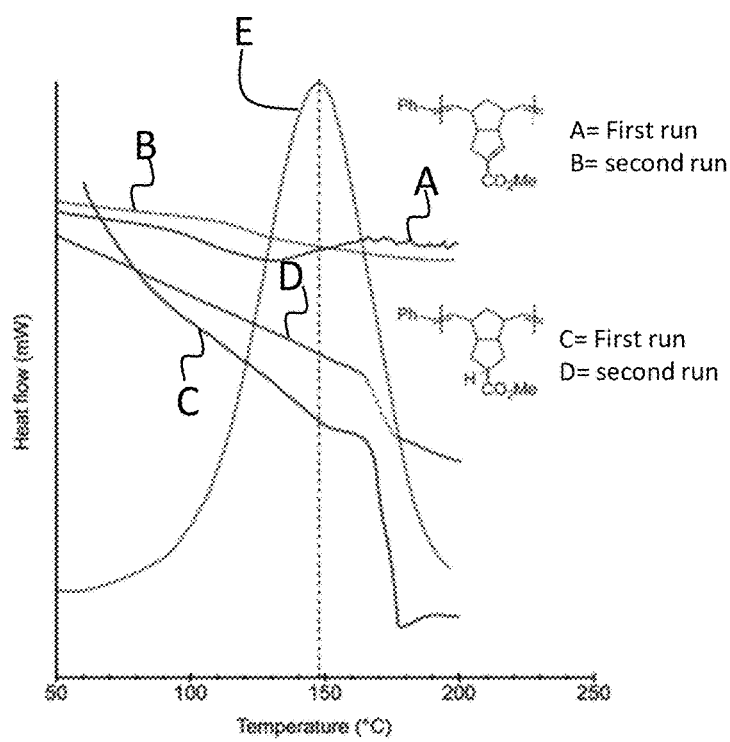
FIG. 12 is a graph of heat flow (mW) as a function of temperature (° C.) showing DSC thermograms for first and second heating cycles of a non-conjugated ester-containing polymer (lines A and B, respectively) and a conjugated ester-containing polymer (lines C and D, respectively), line E represents data for the conjugated ester-containing polymer run on a second instrument that is more sensitive to the appearance of the cross-linking exotherm.
Figure 13:
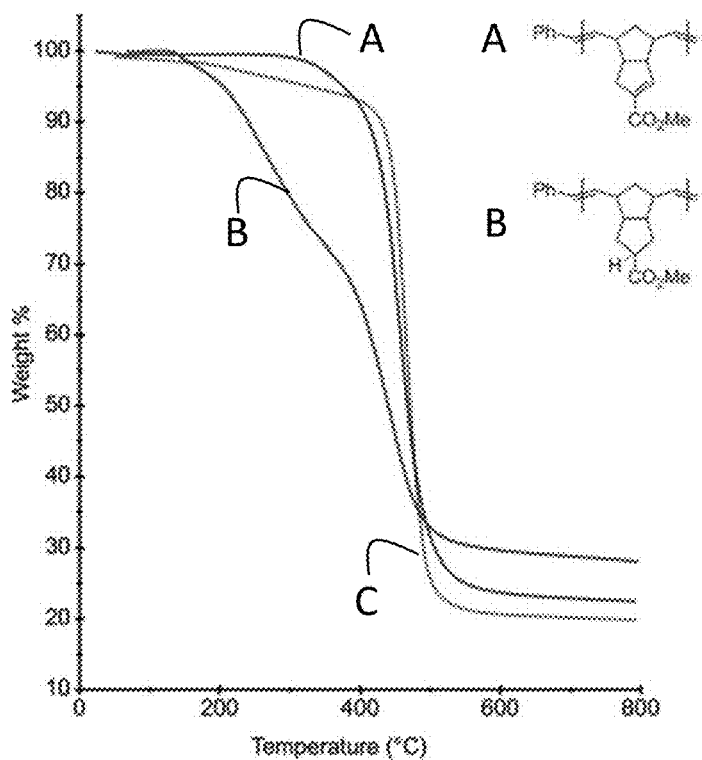
FIG. 13 is a graph of weight percent as a function of temperature (° C.) showing TGA thermograms for a non-conjugated ester-containing polymer (line B) and a conjugated ester-containing polymer (line A) and wherein line C represents results for a commercial sample of unmodified polydicyclopentadiene polymer.

Measurement of the thermal stability of 6a by TGA revealed that the polymer was stable (i.e. experienced no significant mass loss) up to ca. 300° C. In a particular example, polymer 5a and its non-conjugated form were examined by themogravimetric analysis and differential scanning calorimetry (DSC) in order to directly observe any cross-linking events and decomposition processes and to measure any changes in the glass transition temperatures. Polymer 5a exhibited an irreversible exothermic transition at about 145° C., which corresponds to the onset of crosslinking during the DSC experiment. A steep glass transition was then observed at 173° C. (refer to line C in FIG. 12). Heating was stopped at 200° C., and the now-cross-linked sample was allowed to cool to 50° C. before being rerun. No significant change in the Tg was observed for this second run (line D in FIG. 12), nor was any further evidence of cross-linking observed. In thermogravimetric analysis experiments (FIG. 13), the functionalized PDCPD behaved similarly to unmodified PDCPD, exhibiting thermal stability to well over 300° C. Moreover, when the material does eventually decompose, it does so through an apparent single-step process (again, analogous to unmodified PDCPD), suggesting that thermal decomposition is not initiated by loss of a labile functional group (as is the case for other functionalized variants of polydicyclopentadiene), but through the backbone olefin linkages. The non-conjugated polymer behaved quite differently. This material exhibited a much lower Tg (~114° C.; consistent with a mostly linear polydicyclopentadiene), followed by an exotherm at ~130° C. (refer to line A in FIG. 12). This event corresponded to the onset of a decomposition process observed in the TGA experiment (FIG. 13) and likely indicates loss of the more-labile ester (i.e., the methyl isobutyrate function in the polymer, relative to the methyl methacrylate function in the conjugated polymer) though a decarboxylative process. As support for this interpretation, it is noted that the TGA data shows an ~30% mass loss during this first transition, which agrees very closely to the 30% of the total mass of the non-conjugated polymer that resides within the methyl ester group. After again stopping the DSC experiment at 200° C. and allowing the polymer to cool to 50° C., the material was reran two additional times. The presumed decarboxylation described above did result in a modest increase in Tg for these subsequent runs (line B in FIG. 12; Tg=128° C.), but the glass transitions never approached the temperatures expected for an extensively cross-linked polydicyclopentadiene material (>150° C.). In some embodiments, TGA can be conducted using the parameters and device discussed above for DSC analysis.

Much like the increased $T_g$ noted above, the increased thermal robustness shown here is hypothesized to be a result of positioning the functional group at C2 of the dicyclopentadiene monomer. In contrast to the allylically functionalized materials prepared by other groups, products derived from C2-functionalization cannot easily fragment upon thermal activation.

The structure of the crosslinked polymer 6a was studied extensively by solid state NMR, together with infrared and Raman spectroscopy and other analytical methods, as discussed above.

Example 4

Protocol and Discussion:

Uncrosslinked or partially crosslinked PDCPD is oxidatively sensitive due to the density of double bonds in the molecular structure. For example, up to 35% oxygen incorporation following exposure to air has been reported in the art. Without being limited to a particular operating theory, it is currently believed that that this autoxidation process proceeds via radical intermediates and therefore such aerobic oxidation would also constitute a slow crosslinking process, which could be more easily followed spectroscopically or by light scattering than the rapid crosslinking described in Example 3.

Figure 6:
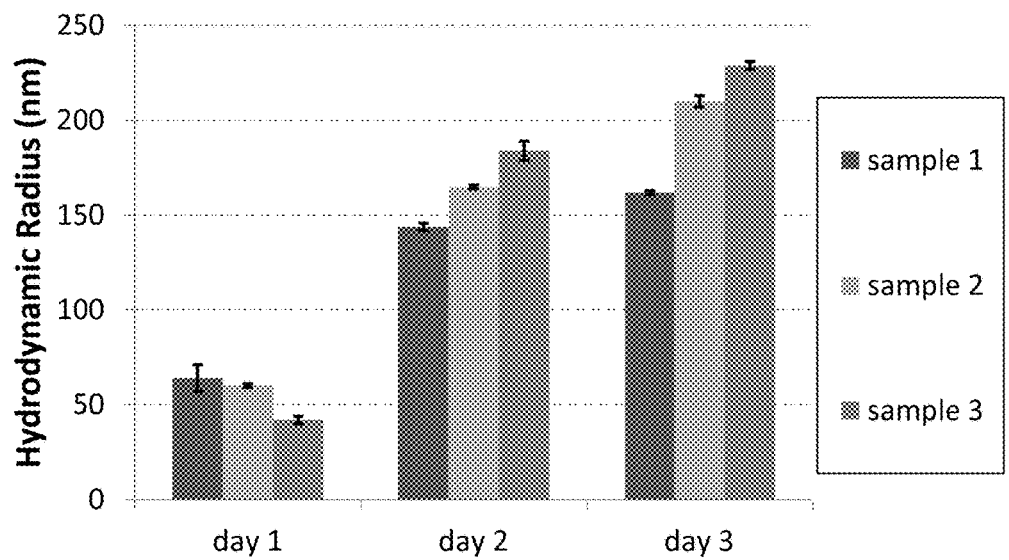
FIG. 6 is a graph illustrating the effects of air on the hydrodynamic radius of different polymer embodiments over three days.

Samples of 5a were exposed to air, and their hydrodynamic radius was monitored by dynamic light scattering (DLS). As shown in the graph of FIG. 6, an increase in hydrodynamic radius was clearly observed. Similar trends were observed for three separate preparations of polymer. This is consistent with the molecular weight range that was obtained following GPC analysis on a 2-day-old sample (~30,000,000 Da). After this time, the sample starts to become distinctly less soluble. Since both GPC and light-scattering data depend on having soluble samples, the numbers obtained from these assays underestimate the actual degree of crosslinking in the samples (i.e. only the less-crosslinked portions of the sample are sufficiently soluble to be analyzed; the remaining material is lost to filtration).

Example 5

Figure 7A:
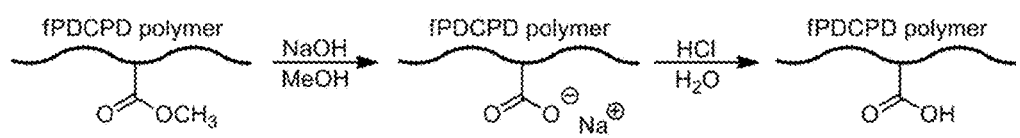

Protocol and Discussion:

To demonstrate that polymer 6 could be chemically modified to control surface energy, a spin-coated film of ester-functionalized polymer on a glass slide was incubated in a solution of sodium hydroxide in methanol to produce an intermediate polymer containing sodium carboxylate groups. This was further incubated in a solution of aqueous hydrochloric acid to produce a polymer containing carboxylic acid groups. See FIG. 7A for a schematic representation. AFM characterization of each polymer surface showed that the samples were no rougher than the glass control. Water-droplet contact angle measurements (FIG. 7B) confirmed that the surface became substantially more hydrophilic as a result of this surface treatment. Since no surface defects on the scale of the drop-size were observed by AFM (FIG. 7C), this property is attributed to changes in the surface chemistry of the polymer.

Exemplary Protocol:

Spin Casting and Functionalization of Polymers—

Spin casting was performed on freshly cleaned, 18×18 mm glass coverslips. Cleaning was performed as follows: 10 min of sonication in chloroform and 10 min in methanol followed by overnight drying under vacuum. Polymer samples were dissolved to 4 wt % in $CH_2Cl_2$ and a 50 µL droplet was dropped onto a coverslip spinning at 2000 rpm. Following deposition, the film was allowed to spin for 60 s to ensure the majority of solvent had been removed.

Linear polymer 5a was spin coated on pre-cleaned glass slides. These coated glass slides were kept in a 180° C. oven under vacuum overnight to give crosslinked polymer 6a. These polymer 6a coated slides were immersed in solution of methanolic NaOH (1:1 MeOH/10% aqueous NaOH) under vacuum. After 8 h, the slides were washed with water and MeOH, then dried in a 70° C. oven under vacuum overnight. The resulting slides (now coated with polymer containing carboxylate residues) were acidified with 10% HCl solution under vacuum for 30 min. All the slides were then washed with water and MeOH, and dried in a 70° C. oven under vacuum overnight to give slides that were coated with carboxylic acid residues.

(2) Atomic Force Microscopy (AFM) Measurements.

AFM measurements of the coated glass coverslips were performed on an Agilent Technologies 5500 Scanning Probe Microscope equipped with a Ted Pella TAP190-G AFM probe operating in tapping mode. In order to minimize vibrations, the microscope was covered in a vibration resistant case on a vibration isolation platform maintained at 80 psi. Each sample was imaged at 3 separate locations on the slide, surface roughness measurements being collected over a 10×10 µm area. Data was analyzed with the use of the Gwyddion data analysis software package. All images underwent slight modification to remove experimental artifacts such as sloped background, contrast alteration for ease of viewing (this was performed after measurements) and in some cases performing Fourier filtering of an unknown 10 Hz noise.

Contact Angle Measurements—A drop of liquid (2 µL) was deposited on the freshly prepared substrate using a Hamilton microsyringe with a mechanical dispenser. Side view images of the drop on the substrate were taken by a high performance aberration corrected imaging lens with precise manual focus adjustment (CMOS sensor). Advancing contact angles were measured on these images. Two glass chips were prepared for each substrate. Three drops of liquid were deposited at three different regions of each film. A mean contact angle and standard deviation were thus determined from the resulting measurements. A sample of conventional PDCPD was obtained from Product Rescue BVBA, Waarschoot, Belgium. Prior to analysis, the sample was polished with 400 grit sandpaper, then washed with water and MeOH, and dried at 70° C. in a vacuum oven overnight.

Surface tensions were calculated by the combination of the OWRK equation (1) and equation (2).

$$0.5\gamma_{lv}(1+\cos\theta)=\sqrt{\gamma_{sv}^d\gamma_{lv}^d}+\sqrt{\gamma_{sv}^p\gamma_{lv}^p} \tag{1}$$

$$\gamma_{sv}=\gamma_{sv}^d+\gamma_{sv}^p \tag{2}$$

$H_2O\gamma_{lv}=72.8$ mN/m, $H_2O\gamma_{lv}^d=21.8$ mN/m, $H_2O\gamma_{lv}^p=50.0$ mN/m $CH_2I_2\gamma_{lv}=50.8$ mN/m, $CH_2I_2\gamma_{lv}^d=50.8$ mN/m, $CH_2I_2\gamma_{lv}^p=0.0$ mN/m θ=contact angle Example 6

Figure 8:
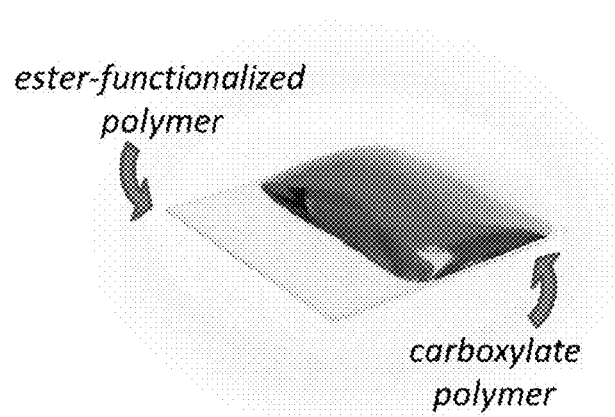
FIG. 8 is an image of a glass coverslip comprising two different sections coated with an ester-functionalized polymer and a carboxylate polymer, wherein water has migrated to the portion of the coverslip coated with the carboxylate-functionalized polymer, thereby illustrating the ability to control hydrophilicity of polymers disclosed herein.

Protocol and Discussion:

To demonstrate the change in hydrophilicity on the macroscale, a glass coverslip spin-coated with ester-functionalized polymer 6 was half-submerged in a solution of methanolic NaOH (1:1 MeOH/10% aqueous NaOH) for 8 h under argon. The resulting slides were washed with water and MeOH, and then dried at 70° C. oven under vacuum overnight. Water (containing green food coloring for imaging purposes) was applied to the surface of the coated slide, using a Pasteur pipette. Drops of water were found to migrate spontaneously to the side of the slide containing the treated (carboxylate-containing) polymer, and away from the untreated (ester-containing) polymer (FIG. 8).

Example 7

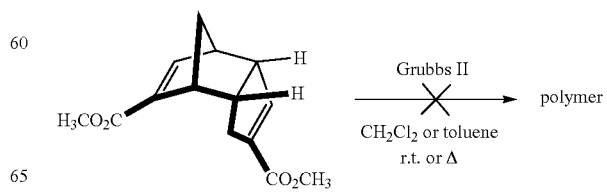

Protocol and Discussion:

A dicyclopentadiene functionalized on both olefins with an ester group (Thiele's ester, pictured above) was also tested as a substrate in the polymerization reaction. This reaction does not proceed under the conditions described for 4a ($CH_2Cl_2$, r.t.) because the strained double bond now contains an additional substituent that impedes the initiation and progress of the olefin metathesis reaction. Even using more vigorous reaction conditions (toluene, 110° C.) returned mostly just dimers or oligomers. No evidence of polymer formation was observed.

Although Thiele ester derivatives are readily available, these data help to illustrate that unsymmetrical monomers such as those disclosed and used herein (e.g., monomer 4) can exhibit superior reactivity.

Exemplary Protocol:

To a solution of Thiele's ester (100 mg, 0.4 mmol) in 10 mL of dry toluene was added Grubbs' second-generation catalyst (17 mg, 0.02 mmol, monomer/catalyst=20:1). The reaction mixture was allowed to stir at 110° C. under an argon atmosphere overnight. The resulting solution was concentrated in vacuo to yield a crude black oil. Analysis of the crude $^1$H-NMR spectrum revealed no polymer arising from Thiele's ester.

Example 8

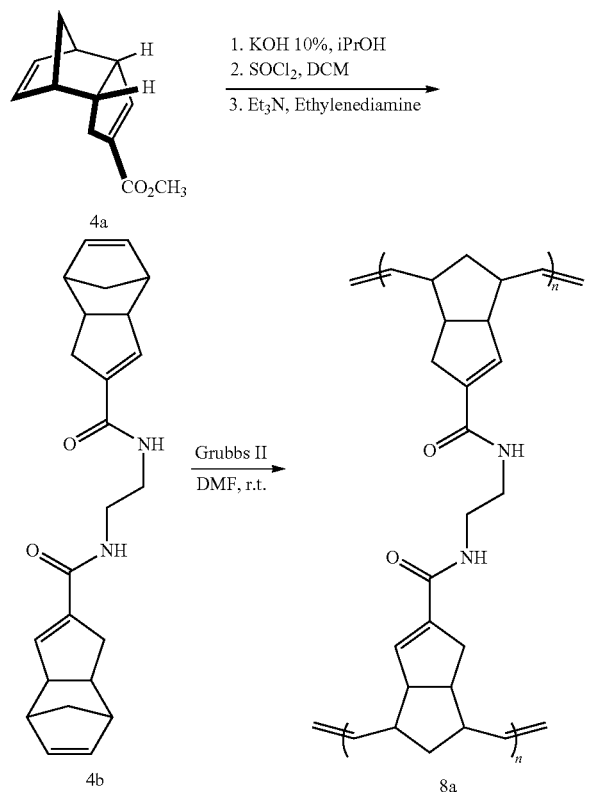

To a solution of 4a (1.1 g, 5.8 mmol) in iPrOH (20 mL) was added KOH (10% solution, 5 mL) dropwise. After 5 hours, iPrOH was removed in vacuo. The mixture was acidified to pH=1 by addition of HCl (2 M) and extracted twice with ethyl acetate. The combined organic layers were dried over $MgSO_4$ and concentrated in vacuo to afford 0.9 g of the corresponding acid as a white powder without further purification. This was dissolved in DCM (20 mL) and $SOCl_2$ (3.6 ml, 50 mmol) was added slowly at 0° C. The mixture was allowed to stir at 40° C. for 2 hours. Then the excess $SOCl_2$ was removed in vacuo. To the resulting residue was added DCM (20 ml), triethylamine (2.1 mL, 15 mmol) and ethylenediamine (0.17 mL, 2.6 mmol). The reaction was stirred overnight. The mixture was quenched by the addition of saturated $NH_4Cl$ and extracted twice with ethyl acetate. The combined organic layers were dried over $MgSO_4$, and concentrated in vacuo. Chromatography (DCM-methanol, 95:5) afforded 4b as a tan solid (798 mg, 73% over 3 steps). $^1$H NMR (300 MHz, $CDCl_3$) δ 6.33 (q, J=2.1 Hz, 2H), 6.00 (dd, J=5.6, 3.0 Hz, 2H), 5.93 (dd, J=5.6, 3.0 Hz, 2H), 3.36-3.44 (m, 4H), 3.28-3.37 (m, 2H), 2.79-2.97 (m, 6H), 2.39 (ddt, J=16.6, 10.3, 2.0 Hz, 2H), 1.90 (dtd, J=16.6, 3.6, 2.0 Hz, 2H), 1.49 (dt, J=8.2, 1.6 Hz, 2H), 1.29 (d, J=8.2 Hz, 2H). $^{13}$C NMR (75 MHz, $CDCl_3$) δ 166.7, 139.8, 139.6, 136.1, 132.9, 55.0, 50.4, 46.5, 45.7, 41.7, 40.3, 33.7.

To a solution of 4b (94 mg, 0.25 mmol) in DMF (3 mL) was added Grubbs second-generation catalyst (5.3 mg, 0.0063 mmol). The mixture was allowed to stir at room temperature for an hour. To this solution was added 7 mL ether. Black precipitate indicated formation of the polymer. The resulting mixture was centrifuged at 3000 rpm and 4° C. for 5 min. The precipitate was isolated and dried in vacuo to give polymer 5 (70 mg, 74%).

Example 9

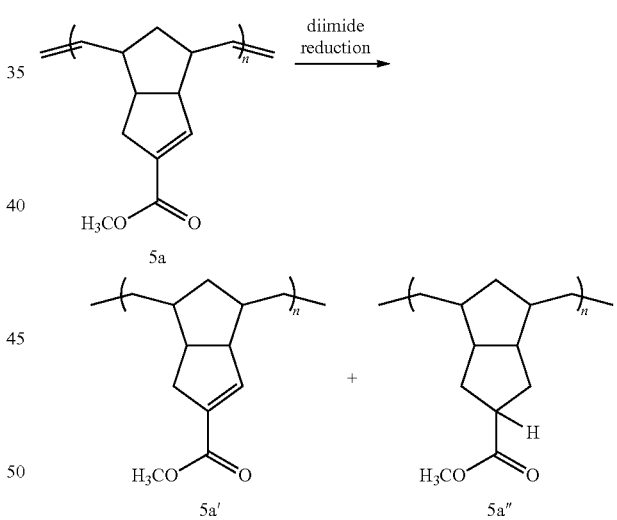

After polymerization in toluene/o-xylene (50 mg, 0.26 mmol, 0.52 M, 1% catalyst), the polymer solution (containing 5a) was diluted to 2% g/mL for hydrogenation without further purification. To the solution, p-toluenesulfonyl hydrazide (TSH; 5-12 equiv.) was added and the mixture was heated to 80-140° C. under nitrogen atmosphere for 2-21 hours. The solvent was removed in vacuo. The hydrogenated polymer was dissolved in dichloromethane and precipitated from methanol three times to remove toluenesulfinic acid. After centrifugation, the polymer was dried in vacuo and collected as white solid. The yield was approximately 90%, and the degree of hydrogenation of the methacrylate and backbone olefins was determined by $^1$H NMR. Data for several exemplary experiments are indicated below.

| entry | solvent | T (° C.) | T (h) | TSH (equiv) | unreacted methacrylate C=C | unreacted backbone C=C |
|---|---|---|---|---|---|---|
| 1 | Toluene | 80 | 11 +10 | 3 +3 | 0.95 0.73 | 0.60 0.32 |
| 2 | Toluene | 110 | 4 | 10 | 0.25 | 0.02 |
| 3 | Toluene | 110 | 10 | 5 | 0.19 | 0 |
| 4 | o-Xylene | 140 | 4 | 12 | 0 | 0 |
| 5 | o-Xylene | 140 | 8 | 12 | 0 | 0 |
| 6 | o-Xylene | 120 | 2 13 +2 | 8 +4 | ~0.28 0.16 0 | ~0 0 0 |
| 7 | Toluene G II 5% pressure vessel | 120 | 6 | 12 | 0.24 | 0 |

Example 11

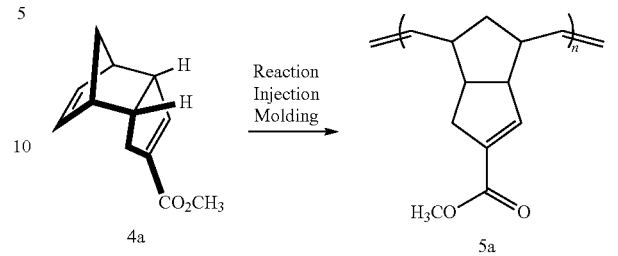

and crosslinked polymers thereof

Example 10

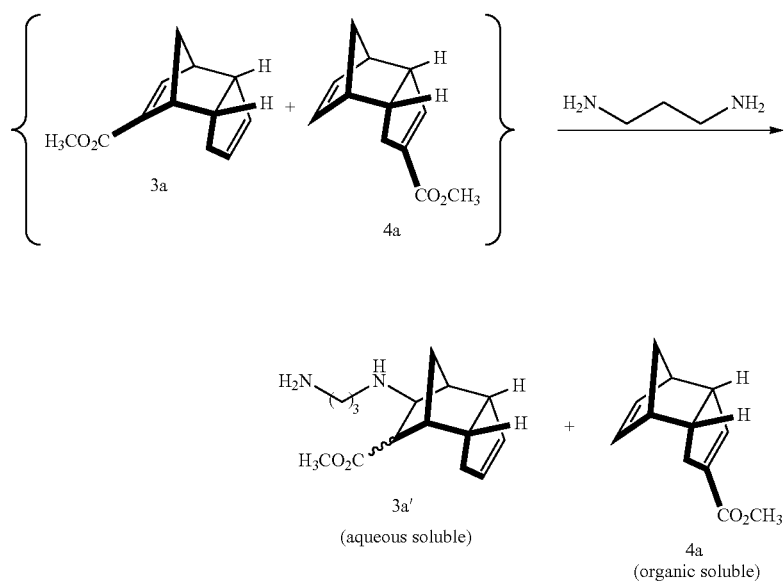

The unpurified mixture of monomers 3a and 4a was (from which residual dicyclopentadiene was removed by evaporation at 50° C. and 0.1 mm Hg, as described above) was stirred in a round-bottom flask. The non-polymerizable regioisomer (27 g, 0.14 mol) was reacted by adding triethylamine (5 equiv., 92.4 mL); DBU (0.5 equiv., 9.8 mL) and 1,3-diaminopropane (5 equiv., 58.1 mL) to the monomer mixture (40 g total) at 0° C. with stirring for 24 hrs under argon. The resulting mixture was dissolved in diethyl ether and washed by HCl, followed by NaHCO$_3$ and NaCl. Volatiles were removed in vacuo, resulting in the isolation of a dark brown oil. The oil was dried under high vacuum to remove solvent residue. Total yield: 60%, conversion 100%.

The crude product was dissolved in hexanes and loaded onto a silica gel column. Elution with 20:1 hexanes: ethyl acetate followed by concentration in vacuo provided the expected polymerizable monomer (4a) as a light yellow oil with an estimated purity (by NMR) of 90%.

Functionalized dicyclopentadiene 4a (purified as indicated in Example 11) was mixed in a glove box with Grubbs second generation catalyst (1 mol %) in a glass vial and stirred with a spatula for 30 seconds. The mixture was taken up in a plastic syringe, and immediately transferred through sprue holes (~2 mm) cut into a ¼" aluminum top plate, into an aluminum mold with a depth of ¼". Test samples prepared in this way had a height of approximately 1" and a variable width and shape, as indicated in FIG. 9.

The samples were allowed to polymerize for 24 h in the glove box, after which the mold (still containing the polymer samples) was removed from the glove box and placed in an oven at 135° C. to effect thermal curing. Different curing times (30 minutes to 24 hours) provided samples with different degrees of coloring. The mold was then disassembled by removing the top and bottom plates, and the samples were removed. In some examples, pre-coating the aluminum mold (as well as the associated top and bottom plates) with a Teflon spray facilitated easier sample removal. In other examples, the top plate was not used, and material was added directly to the open mold.

Figure 9:
FIG. 9 is an image of an aluminum mold suitable for reaction injection molding, together with objects prepared using embodiments of the monomer embodiments described herein in an RIM method.

Exemplary embodiments of molds and polymer samples are shown in FIG. 9.

Example 12

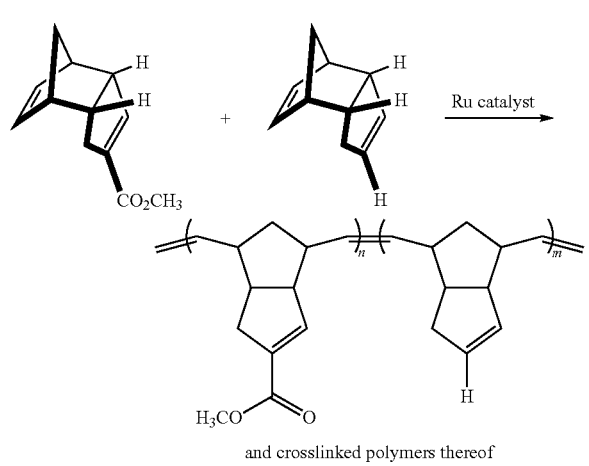

and crosslinked polymers thereof

Figure 10:
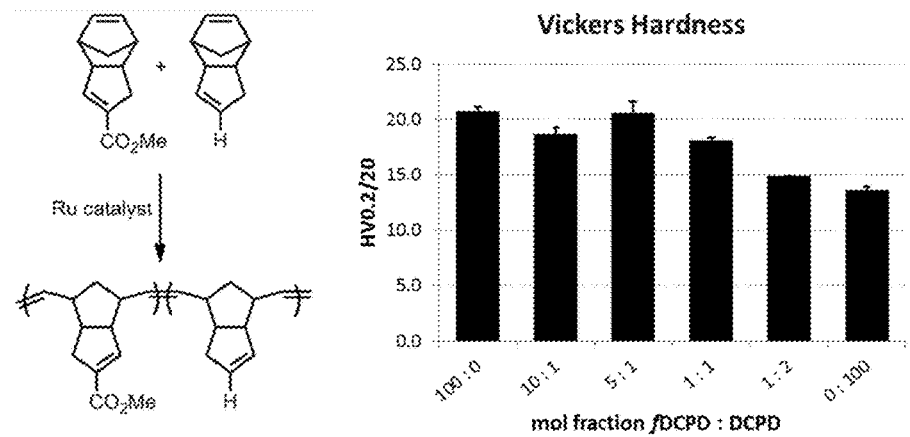
FIG. 10 illustrates differences in material hardness for copolymers made from ester-functionalized dicyclopentadiene and unfunctionalized dicyclopentadiene monomers, combined together in different ratios.

Solid dicyclopentadiene was preheated by a blow dryer for 5 min to effect melting, prior to mixing with various mole fractions of methyl-ester functionalized dicyclopentadiene in a glove box (fDCPD:DCPD 1:0; 10:1; 5:1; 1:1; 1:2; 0:1). The samples were mixed with a spatula for 30 seconds in a silicone mold, after which Grubbs second generation catalyst (1 mol %) was added to the mixture, and stirring was continued for 60 seconds. Polymerization was allowed to take place over 24 hrs. The samples (still in the silicone molds) were taken from the glove box and thermally cured in oven at 135° C. for 10 mins. Neat polymer samples were then removed from the molds and analyzed. Subsequent thermal crosslinking was undertaken in oven at 135° C. for another 20 min to 5 days. Exemplary Vickers hardness measurements for fully crosslinked samples are shown in FIG. 10.

Example 13

Samples of pure functionalized or nonfunctionalized polydicyclopentadiene were prepared as described above, and tested by dynamic mechanical thermal analysis (DMTA) on an Anton Paar MCR 302 rheometer with SRF 12 geometry and CTD 600 oven. Temperature-sweep measurements were performed with a strain of 0.1% and a frequency of 1 Hz. Tested samples were solid rectangular bars of dimensions 12 mm×4 mm×25 mm.

Complementary hardness tests were completed on a Buehler Wilson VH 3100 instrument with a Vickers diamond shaped indenter. Tested samples were solid cylinders with a height of 14.5 mm and diameter of 14.5 mm.

Figure 11:
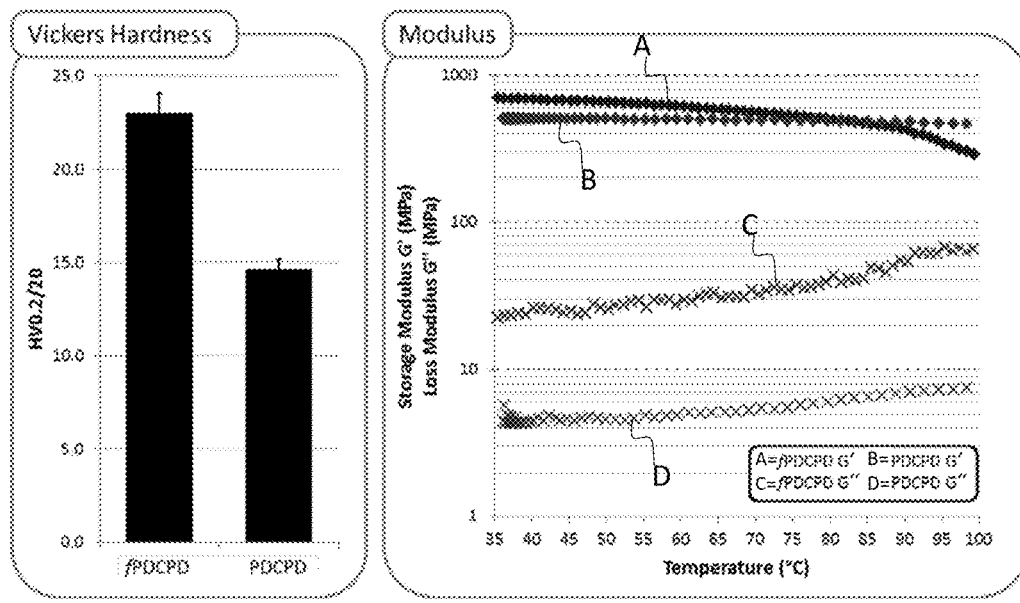
FIG. 11 shows exemplary hardness and DMTA data for crosslinked homopolymer samples prepared from functionalized or unfunctionalized dicyclopentadiene monomers.

Exemplary hardness and DMTA data are shown in FIG. 11.

Example 14

In this example, a non-conjugated ester-containing monomer was polymerized to provide a non-conjugated ester-containing polymer as illustrated in Scheme 11 below. With reference to this scheme, selective reduction of the conjugated ester-containing polymer to the desired saturated monomer was effected using a pinacol-borane/diazaphospholene catalyst system. The saturated monomer was then polymerized to the corresponding linear polymer under standard ring-opening metathesis conditions.

Scheme 11

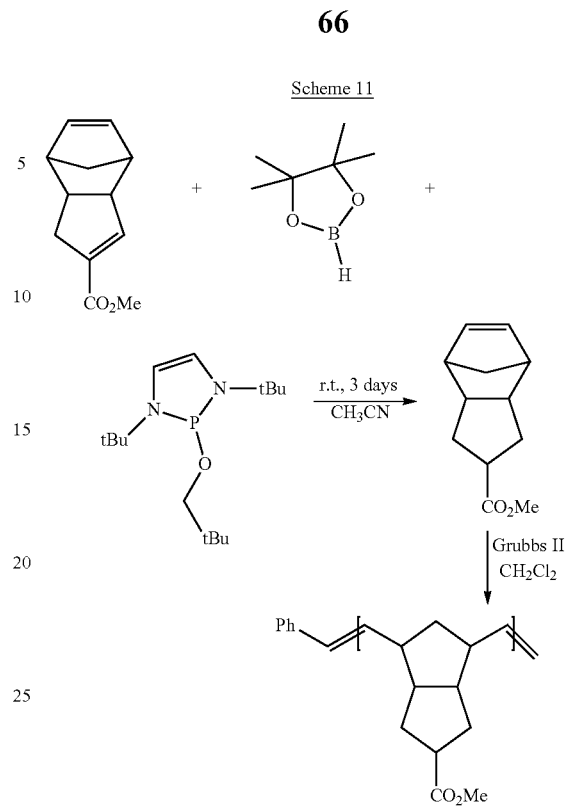

VI. Overview of Several Embodiments

Described herein are embodiments of a method, comprising reacting cyclopentadiene with a substituted cyclopentadiene compound, or a salt thereof, to form a multicyclic compound having a structure satisfying Formula A and/or Formula B

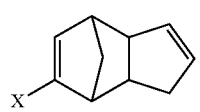

Formula A

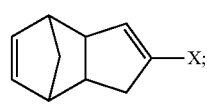

Formula B wherein the substituted cyclopentadiene compound has a structure satisfying a formula

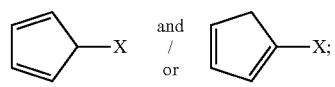

and wherein X is an electron-withdrawing group radical-stabilizing group, or other non-hydrogen functional group. In some embodiments, the salt of the substituted cyclopentadiene has a structure satisfying a formula

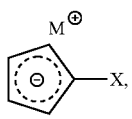

wherein M is a metal counterion or non-metal counterion and in such embodiments, the reaction can occur under acidic conditions.

In any or all of the above embodiments, M is an alkali metal, an alkaline earth metal, or a tetra-substituted ammonium species.

In any or all of the above embodiments, the method can further comprise performing an olefin metathesis reaction on the multicyclic compound.

In some embodiments, polymers made from polymerizing a multicyclic compound having a structure satisfying a formula

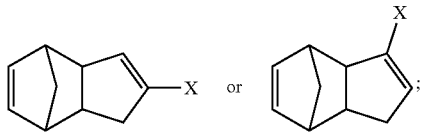

wherein X is functional group other than hydrogen, such as an electron-withdrawing group or radical-stabilizing group are described.

In any or all of the above embodiments, the polymer is a reaction product of an olefin metathesis reaction product made from the multicyclic compound.

In some embodiments, a polymer made from polymerizing a mixture of multicyclic compounds, wherein the mixture of multicyclic compounds comprises a mixture of regioisomeric compounds having structures satisfying formulas

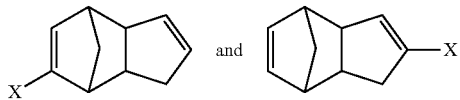

wherein X is an electron-withdrawing group or radical-stabilizing group is described.

In any or all of the above embodiments, the polymer is a reaction product of an olefin metathesis reaction between at least one multicyclic compound having a formula

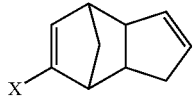

and at least one multicyclic compound having a formula

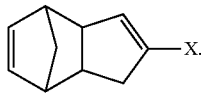

In some embodiments, methods are described wherein the methods comprise combining (i) an photoredox mediator compound or (ii) a catalyst comprising ruthenium (Ru), molybdenum (Mo), tungsten (W), titanium (Ti), tantalum (Ta), or a combination thereof; and a compound having a structure satisfying a formula

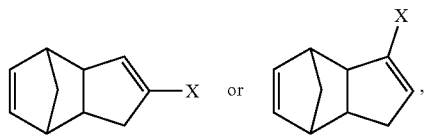

or a combination thereof, to form a polymer; wherein X is an electron-withdrawing group or radical-stabilizing group.

In some embodiments a linear polymer is described having a structure satisfying a formula

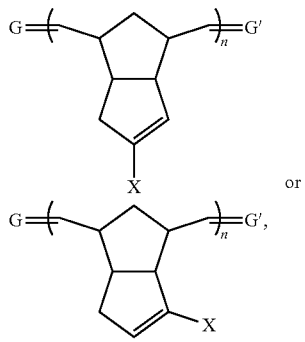

wherein each of G and G' independently is selected from an end-capping group; n is any integer value greater than 10; and X is a functional group other than hydrogen, such as an electron-withdrawing group or radical-stabilizing group.

In any or all of the above embodiments, the end-capping group is selected from —CH$_2$, —CH(aryl), —CH(aliphatic), —CH(heteroaliphatic), or —CH(heteroaryl).

In some embodiments, a polymer or copolymer comprising at least one subunit having a structure satisfying a formula

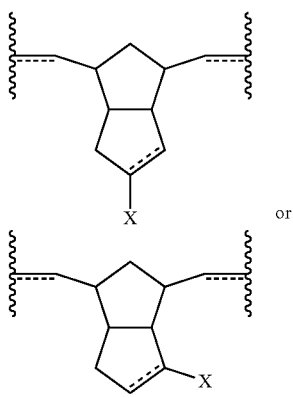

wherein X is functional group other than hydrogen, such as an electron-withdrawing group or radical-stabilizing group is described.

In some embodiments, a crosslinked polymer made from a polymer and/or copolymer as described by any or all of the above embodiments.

In any or all of the above embodiments, the crosslinked polymer can have a structure satisfying a formula selected from:

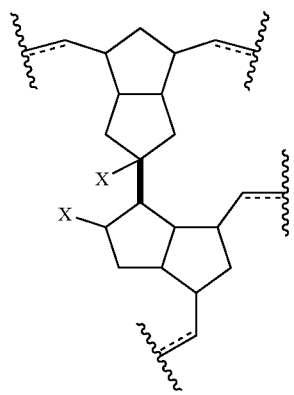

or

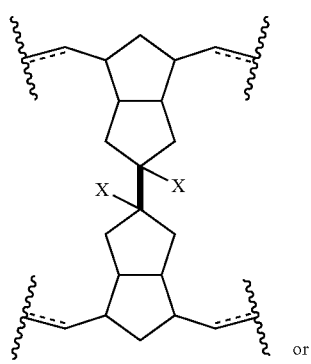

or

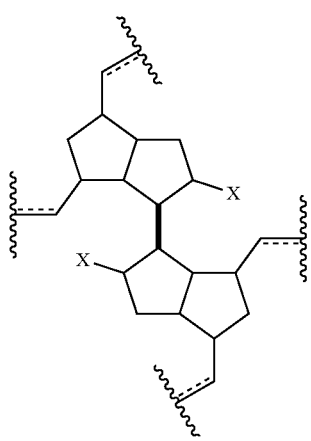

or

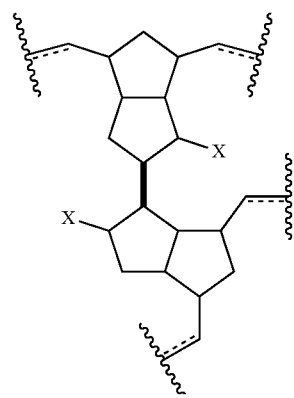

or

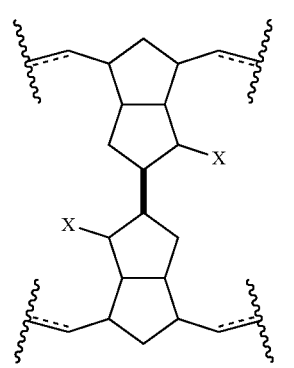

or

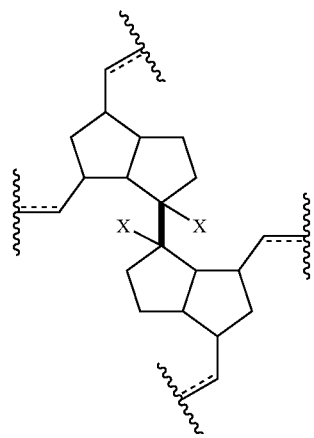

wherein a bold line of the formula comprises a primary molecular crosslink, which can further comprise one or more functional groups or polymer subunits; and X is an electron-withdrawing group or radical-stabilizing group.

Also described herein are polymers comprising one or more molecular crosslinks and having a structure satisfying a formula selected from:

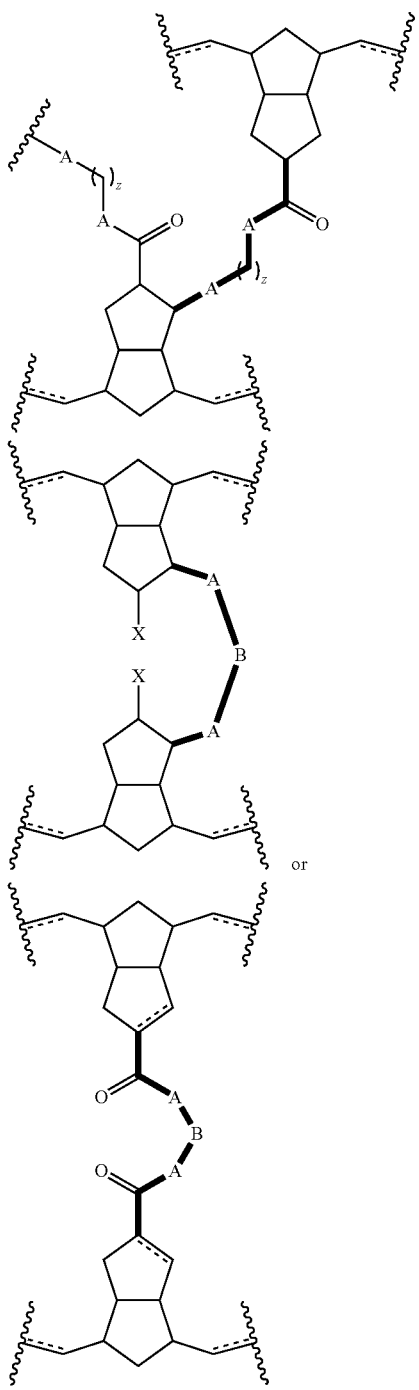

or

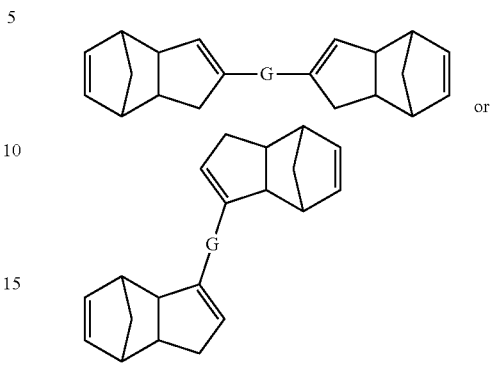

or a combination thereof; wherein G is a linking group or a cleavable linking group are described.

In any or all of the above embodiments, the linking group is selected from an ester, an amide, an alkyl group, an aromatic group, a heteroaromatic group, an olefin, an alkyne, an ether, a silyl ether, an alkyl silane, a disulfide, a cyclic group, or a combination thereof; and the cleavable linking group is selected from a linking group capable of being cleaved under radical conditions, oxidative conditions, enzymatic conditions, electromagnetic radiation conditions, reductive conditions, acidic conditions, basic conditions, or metal-catalyzed conditions.

In some embodiments, a polymer comprising at least one molecular crosslink is disclosed, wherein the polymer has a structure satisfying a formula:

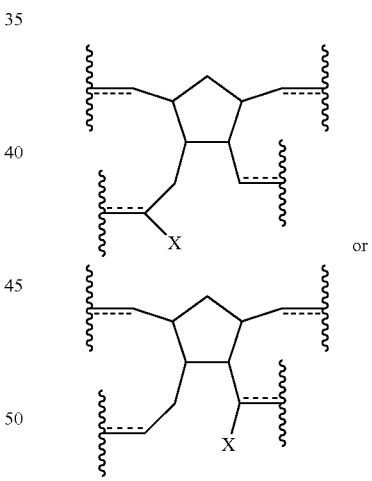

wherein one or more bold lines of the formula independently comprises a primary molecular crosslink, which can further comprise one or more functional groups or polymer subunits; A is a heteroatom or heteroatom-containing group; B is a linking group; Z is an integer between 0 and 10; and X is an electron-withdrawing group or radical-stabilizing group.

In any or all of the above embodiments, the heteroatom is O or S and the heteroatom group is NH or NR, wherein R is alkyl, aromatic, heteroaromatic, or a combination thereof.

In any or all of the above embodiments, the linking group is selected from an alkyl group, aromatic group, a heteroaromatic group, or a combination thereof wherein X is a functional group other than hydrogen, such as an electron-withdrawing group or radical-stabilizing group.

Also disclosed herein are methods for reversing the molecular crosslinks any or all of the above embodiments, comprising exposing the polymer to radical conditions, oxidative conditions, enzymatic conditions, electromagnetic radiation conditions, reductive conditions, acidic conditions, basic conditions, or metal-catalyzed conditions.

In any or all of the above embodiments, reversing comprises cleaving all molecular crosslinks of the polymer.

In any or all of the above embodiments, reversing comprises cleaving fewer than all molecular crosslinks of the polymer.

In any or all of the above embodiments, reversing comprises cleaving interstrand and/or intrastrand bonds of the polymer.

In any or all of the above embodiments, the method is used to recycle polymer (including copolymers) derived from linear polymers having a subunit having a structure satisfying a formula:

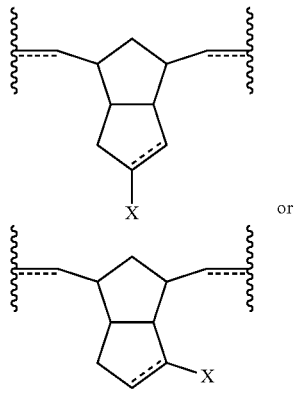

wherein X is an electron-withdrawing group or radical-stabilizing group.

In some embodiments, methods of modifying a polymer, copolymer, and/or crosslinked polymer of any or all of the above embodiments are described wherein the method comprises exposing the polymer, copolymer, and/or crosslinked polymer to a chemical process or physical process capable of converting a functional group of the polymer, copolymer, and/or crosslinked polymer.

In any or all of the above embodiments, the chemical process is selected from a hydrogenation reaction, an esterification reaction, a hydrolysis reaction, a condensation reaction, a metal-mediated coupling, a decarboxylation reaction, a photochemical reaction, an addition of a radical, a nucleophilic species, electrophilic species, or combinations thereof.

In any or all of the above embodiments, the method is used to enhance stability of the polymer (e.g., enhancing stability to atmospheric oxygen), control the surface energy of the polymer, to improve adhesion or other properties, or combinations thereof.

In any or all of the above embodiments, X is selected from an ester (—CO$_2$R), an acid (—CO$_2$H), an amide (—CONRR'), a ketone (—COR), an aldehyde (—COH), a nitrile (—CN), a nitro group (—NO$_2$), a trifluoromethyl group (—CF$_3$), an alkoxy group (—OR), a phosphine oxide, or a sulfur-containing species; wherein R and R' independently are selected from H, aliphatic, aryl, heteroaliphatic, heteroaryl, or combinations thereof; —(CH$_2$)$_y$OH; —(CH$_2$)$_y$SH; or —(CH$_2$)$_y$NR$^a$R$^b$, where y is an integer between 0 and 10 and R$^a$ and R$^b$ independently are selected from H, aliphatic, aryl, heteroaliphatic, heteroaryl, or combinations thereof.

In any or all of the above embodiments, wherein one or both of R and R' is substituted with a functional group selected from a dye, fluorophore, bioactive structure, molecular sensor, or any and all combinations thereof.

In view of the many possible embodiments to which the principles of the disclosed technology may be applied, it should be recognized that the illustrated embodiments are only preferred examples of the present disclosure and should not be taken as limiting the scope of the present disclosure. Rather, the scope is defined by the following claims. We therefore claim as our invention all that comes within the scope and spirit of these claims.

We claim:

1. A method, comprising:
reacting cyclopentadiene with a substituted cyclopentadiene compound, or a salt thereof, to form a multicyclic compound having a structure satisfying Formula A and/or Formula B

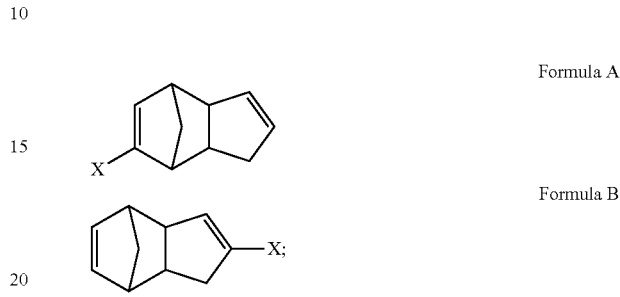

wherein the substituted cyclopentadiene compound has a structure satisfying a formula

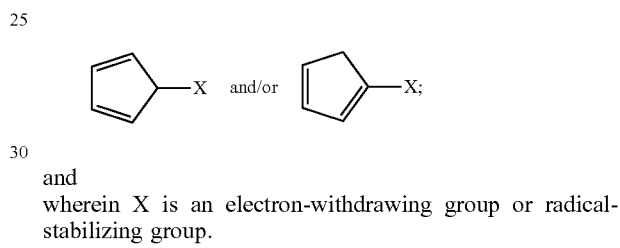

and
wherein X is an electron-withdrawing group or radical-stabilizing group.

2. The method of claim 1, wherein the salt of the substituted cyclopentadiene compound has a structure satisfying a formula

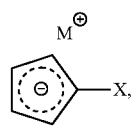

wherein M is a metal counterion or non-metal counterion, and wherein reacting occurs under acidic conditions.

3. The method of claim 2, wherein M is an alkali metal, an alkaline earth metal, or a tetra-substituted ammonium species and X is selected from an ester (CO$_2$R), an acid (CO$_2$H), an amide (—CONRR'), a ketone (—COR), an aldehyde (—COH), a nitrile (—CN), a nitro group (—NO$_2$), a trifluoromethyl group (—CF$_3$), an alkoxy group (—OR), a phosphine oxide, or a sulfur-containing species; wherein R and R' independently are selected from H, aliphatic, aryl, heteroaliphatic, heteroaryl, or combinations thereof; —(CH$_2$)$_y$OH; —(CH$_2$)$_y$SH; or —(CH$_2$)$_y$NR$^a$R$^b$, where y is an integer between 0 and 10 and R$^a$ and R$^b$ independently are selected from H, aliphatic, aryl, heteroaliphatic, heteroaryl, or combinations thereof.

4. The method of claim 1, further comprising performing an olefin metathesis reaction on the multicyclic compound.

5. The method of claim 1, wherein a conjugate addition is used to remove isomers of Formula A from isomers of Formula B.

6. A polymer made from:
(i) polymerizing the multicyclic compound having a structure satisfying Formula A and/or Formula B Formula A

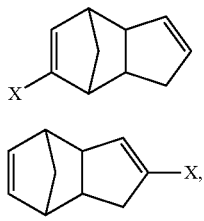

Formula B wherein X is an electron-withdrawing group or radical-stabilizing group; or
(ii) polymerizing a mixture of multicyclic compounds, wherein the mixture of multicyclic compounds comprises a mixture of regioisomeric compounds having structures satisfying formulas

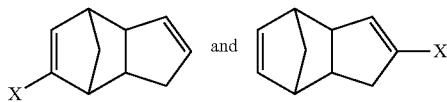

wherein X is an electron-withdrawing group or radical-stabilizing group; or
(iii) polymerizing a pre-crosslinked monomer having a structure satisfying a formula

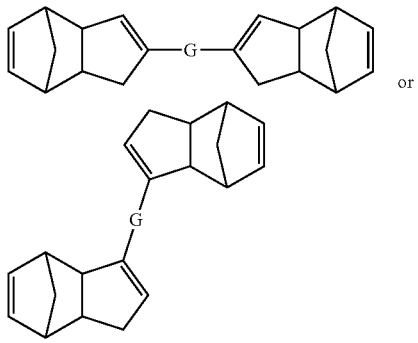

or a combination thereof; wherein G is a linking group or a cleavable linking group.

7. The polymer of claim 6, wherein X is selected from an ester (—CO$_2$R), an acid (—CO$_2$H), an amide (—CONRR'), a ketone (—COR), an aldehyde (—COH), a nitrile (—CN), a nitro group (—NO$_2$), a trifluoromethyl group (—CF$_3$), an alkoxy group (—OR), a phosphine oxide, or a sulfur-containing species; wherein R and R' independently are selected from H, aliphatic, aryl, heteroaliphatic, heteroaryl, or combinations thereof; —(CH$_2$)$_y$OH; —(CH$_2$)$_y$SH; or —(CH$_2$)$_y$NR$^a$R$^b$, where y is an integer between 0 and 10 and R$^a$ and R$^b$ independently are selected from H, aliphatic, aryl, heteroaliphatic, heteroaryl, or combinations thereof.

8. The polymer of claim 6, wherein the linking group is selected from an ester, an amide, an alkyl group, an aromatic group, a heteroaromatic group, an olefin, an alkyne, an ether, a silyl ether, an alkyl silane, a disulfide, a cyclic group, or a combination thereof; and the cleavable linking group is selected from a linking group capable of being cleaved under radical conditions, oxidative conditions, enzymatic conditions, electromagnetic radiation conditions, reductive conditions, acidic conditions, basic conditions, or metal-catalyzed conditions.

9. A polymer, comprising at least one subunit having a structure satisfying one or more of the following formulas:

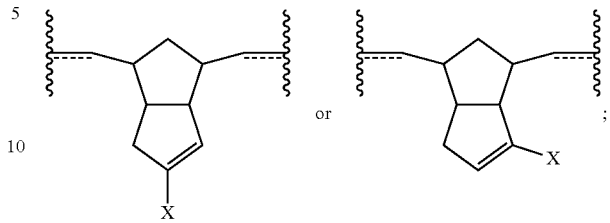

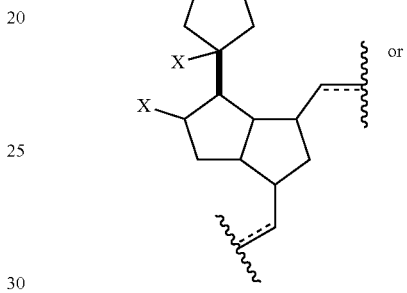

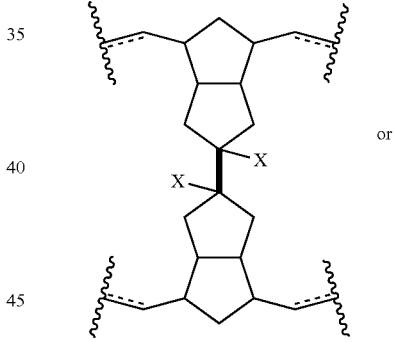

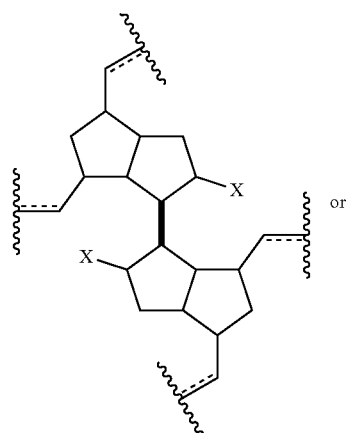

-continued

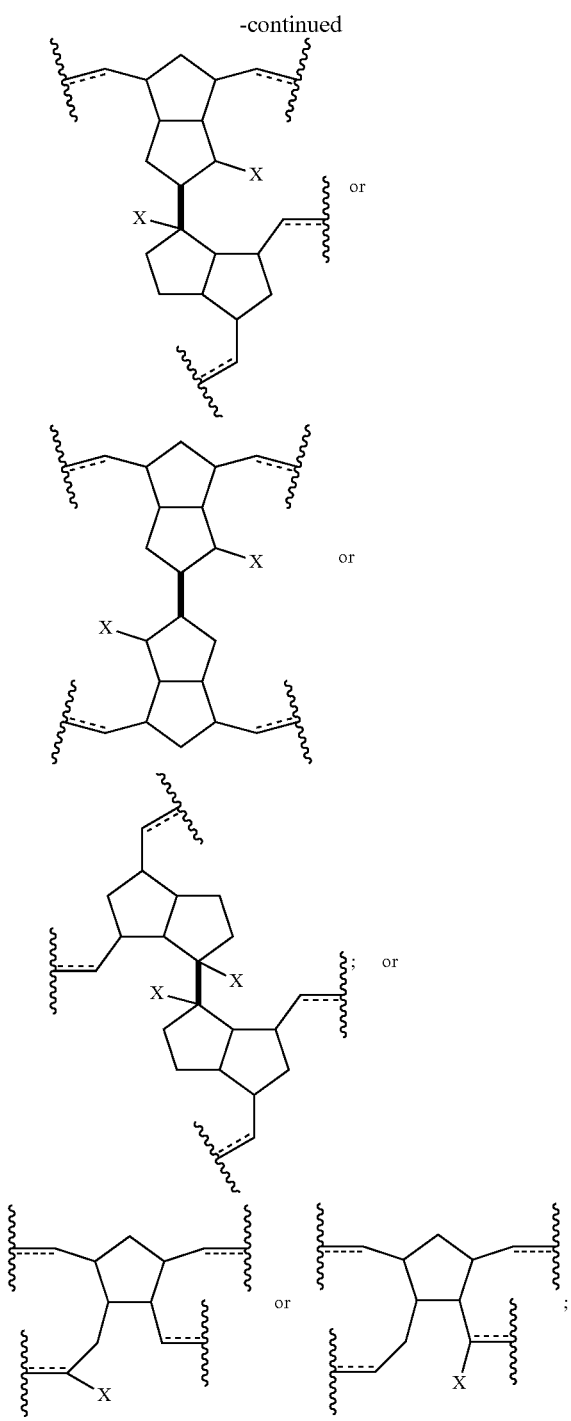

wherein
X is an electron-withdrawing group or radical-stabilizing group; and
a bold line of the crosslinked form comprises a primary molecular crosslink, which can further comprise one or more functional groups or polymer subunits.

10. The polymer of claim 9, wherein X is selected from an ester (—$CO_2R$), an acid (—$CO_2H$), an amide (—CONRR'), a ketone (—COR), an aldehyde (—COH), a nitrile (—CN), a nitro group (—$NO_2$), a trifluoromethyl group (—$CF_3$), an alkoxy group (—OR), a phosphine oxide, or a sulfur-containing species; wherein R and R' independently are selected from H, aliphatic, aryl, heteroaliphatic, heteroaryl, or combinations thereof; —$(CH_2)_yOH$; —$(CH_2)_ySH$; or —$(CH_2)_yNR^aR^b$, where y is an integer between 0 and 10 and $R^a$ and $R^b$ independently are selected from H, aliphatic, aryl, heteroaliphatic, heteroaryl, or combinations thereof.

11. The polymer of claim 9, wherein the polymer is a linear polymer having a structure satisfying a formula

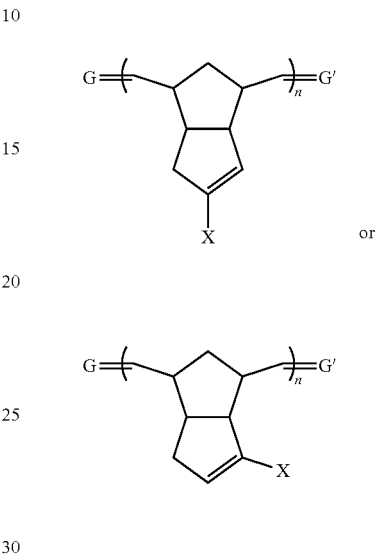

wherein
each of G and G' independently is selected from an end-capping group; and
n is any integer value greater than 10.

12. The polymer of claim 11, wherein the end-capping group is selected from
$CH_2$, —CH(aryl), —CH(aliphatic), —CH(heteroaliphatic), or —CH(heteroaryl).

13. A polymer, comprising one or more molecular cross-links and having a structure satisfying a formula selected from:

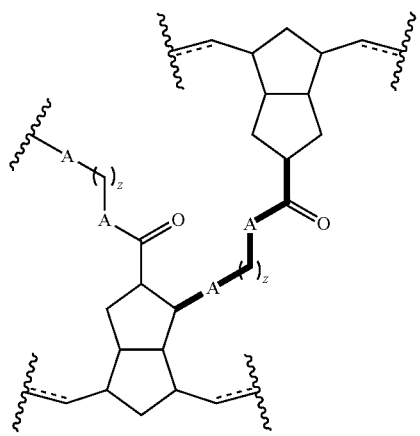

-continued

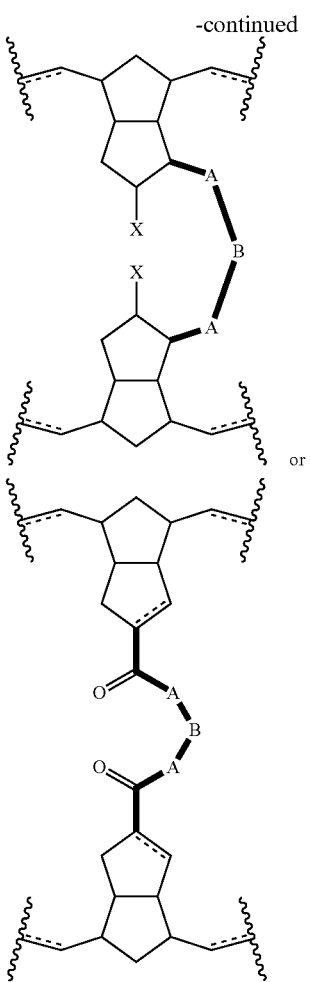

or wherein
one or more bold lines of the formula independently comprises a primary molecular crosslink, which can further comprise one or more functional groups or polymer subunits;

A is a heteroatom or heteroatom-containing group;
B is a linking group;
Z is an integer between 0 and 10; and
X is an electron-withdrawing group or radical-stabilizing group.

14. The polymer of claim 13, wherein the heteroatom is O or S and the heteroatom group is NH or NR, wherein R is alkyl, aromatic, heteroaromatic, or a combination thereof.

15. The polymer of claim 13, wherein the linking group is selected from an alkyl group, aromatic group, a heteroaromatic group, or a combination thereof.

16. A method, comprising:
forming a polymer by combining (i) a photoredox mediator compound or a catalyst comprising ruthenium (Ru), molybdenum (Mo), tungsten (W), titanium (Ti), tantalum (Ta), or a combination thereof; and (ii) a compound having a structure satisfying a formula

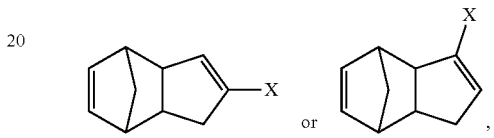

or a combination thereof; wherein X is an electron-withdrawing group or radical-stabilizing group.

17. The method of claim 16, further comprising exposing the polymer to a chemical process or physical process that converts a functional group of the polymer.

18. The method of claim 17, wherein the chemical process is selected from an esterification reaction, a hydrolysis reaction, a condensation reaction, a metal-mediated coupling, a decarboxylation reaction, a photochemical reaction, an addition of a nucleophilic species, or combinations thereof.

19. The method of claim 17, wherein the method is used to control a surface energy of the polymer to improve adhesion or other properties.

20. The method of claim 17, wherein the chemical process is a diimide reduction.

21. The method of claim 16, wherein the polymer is produced in a reaction injection molding process.

* * * * *